United States Patent [19]
DeFrees et al.

[11] Patent Number: 5,604,207
[45] Date of Patent: Feb. 18, 1997

[54] SIALYL LE$^x$ ANALOGUES AS INHIBITORS OF CELLULAR ADHESION

[75] Inventors: Shawn A. DeFrees, San Marcos; Federico C. A. Gaeta, Olivenhain; John J. Gaudino, Westlake Village, all of Calif.; Zhongli Zheng, Lexington, Mass.; Masaji Hayashi, Kobe, Japan

[73] Assignee: Cytel Corporation, San Diego, Calif.

[21] Appl. No.: 345,072

[22] Filed: Nov. 28, 1994

Related U.S. Application Data

[63] Continuation-in-part of Ser. No. 241,645, May 12, 1994, which is a continuation-in-part of Ser. No. 62,120, May 14, 1993, abandoned.

[51] Int. Cl.$^6$ ............... A61K 31/715; A61K 31/73; C07H 3/06
[52] U.S. Cl. .................. 514/25; 514/54; 514/61; 514/62; 536/17.2; 536/63; 536/64; 536/65; 536/55; 536/55.1; 536/55.2
[58] Field of Search ............... 536/17.2, 63, 64, 536/65, 55, 55.1, 55.2; 514/25, 54, 61, 62

[56] References Cited

U.S. PATENT DOCUMENTS

| | | | |
|---|---|---|---|
| 5,143,712 | 9/1992 | Brandley et al. | 424/1.73 |
| 5,211,936 | 5/1993 | Brandley | 424/1.73 |
| 5,211,937 | 5/1993 | Brandley et al. | 424/1.73 |
| 5,324,663 | 6/1994 | Lowe | 435/320.1 |
| 5,352,670 | 10/1994 | Venot et al. | 514/54 |

OTHER PUBLICATIONS

Green et al. *Biochem. Biiophys. Res. Commun.* Oct. 15, 1992, 188(1), 244–251.
Needham et al. *Proc. Nat. Acad. Sci. USA* Feb. 1993, 90, 1359–1363.
DeFrees et al. *J. Am. Chem. Soc.* Aug. 11, 1993, 115(16), 7549–7550.
Tyrell et al. *Proc. Natl. Acad. Sci. USA* 1991, 88, 10372–10376.
Zhou et al. *J. Cell Biol.* 1991, 115(2), 557–563.
Danishefsky et al. *J. Am Chem. Soc.* 1992, 114(21), 8331–8333.
Phillips, et al. (1990) "ELAM–1 mediates cell adhesion by recognition of a carbohydrate ligand, Sialyl–Le$^x$", *Science*, 250: 1130–1131.
Walz, et al. (1990) "Recognition by ELAM–1 of Sialyl–Le$^x$ determinant on myeloid and tumor cells", *Science*, 250:1132–1135.
Munro, et al. (1992) "Expression of Sialyl–Lewis X, an E–selectin ligand, in inflammation, immune processes, and lymphoid tissues", *American Journal of Pathology*, 141(6):1397–1408.
Ball, et al. (1991) "Structural requirements for the carbohydrate ligand of E–selectin", *Proceedings of the National Academy of Sciences*, 88:10372–10376.

Primary Examiner—Gary L. Kunz
Assistant Examiner—Kathleen Kahler Fonda
Attorney, Agent, or Firm—Townsend and Townsend and Crew

[57] ABSTRACT

The inventive compounds are analogues of sialyl Le$^x$ that inhibit cellular adhesion between a selectin and cells that express sialyl Le$^x$ on their surfaces, and their synthetic intermediates. An inventive compound has structure A,

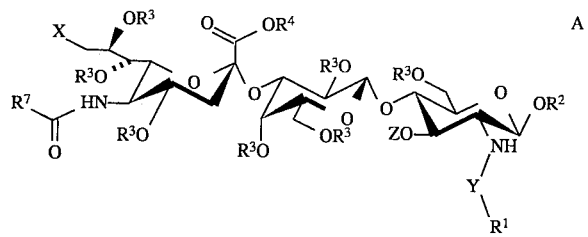

wherein
Z is hydrogen, $C_1$–$C_6$ acyl or

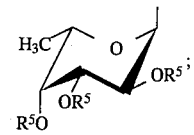

Y is C(O), $SO_2$, HNC(O), OC(O) or SC(O);
$R^1$ is an aryl, a substituted aryl or a phenyl $C_1$–$C_3$ alkylene group, wherein an aryl group has one five- or six-membered aromatic ring, a fused five/six-membered aromatic ring, or two fused six-membered aromatic rings, which rings are hydrocarbyl, monooxahydrocarbyl, monothiahydrocarbyl, monoazahydrocarbyl or diazahydrocarbyl rings, and a substituted aryl group is an aryl group having a halo, trifluoromethyl, nitro, $C_1$–$C_{18}$ alkyl, $C_1$–$C_{18}$ alkoxy, amino, mono-$C_1$–$C_{18}$ alkylamino, di-$C_1$–$C_{18}$ alkylamino, benzylamino, $C_1$–$C_{18}$ alkylbenzylamino, $C_1$–$C_{18}$ thioalkyl or $C_1$–$C_{18}$ alkyl carboxamido substituent, or
$R^1$ Y is allyloxycarbonyl or chloroacetyl;
$R^2$ is hydrogen, $C_1$–$C_{18}$ straight chain, branched chain or cyclic hydrocarbyl, $C_1$–$C_6$ alkyl $C_1$–$C_5$ alkylene ω-carboxylate, ω-tri($C_1$–$C_4$ alkyl/phenyl)silyl $C_2$–$C_4$ alkylene, monosaccharide or disaccharide,
or $OR^2$ together form a $C_1$–$C_{18}$ straight chain, branched chain or cyclic hydrocarbyl carbamate;
$R^3$ is hydrogen or $C_1$–$C_6$ acyl;
$R^4$ is hydrogen, $C_1$–$C_6$ alkyl or benzyl;
$R^5$ is hydrogen, benzyl, methoxybenzyl, dimethoxybenzyl or $C_1$–$C_6$ acyl;
$R^7$ is methyl or hydroxymethyl; and
X is $C_1$–$C_6$ acyloxy, $C_2$–$C_6$ hydroxylacyloxy, hydroxy, halo or azido.

44 Claims, No Drawings

500
SIALYL LE$^x$ ANALOGUES AS INHIBITORS OF CELLULAR ADHESION

CROSS-REFERENCE TO RELATED APPLICATIONS

This is a continuation-in-part of application Ser. No. 08/241,645, filed May 12, 1994, that is a continuation-in-part of application Ser. No. 08/062,120 filed May 14, 1993, now abandoned, whose disclosures are incorporated by reference.

DESCRIPTION

1. Technical Field

The present invention relates to compounds that inhibit cellular adhesion, and more particularly relates to analogue compounds of sialyl Lewis$^x$ (sialyl Le$^x$ or SLe$^x$) that inhibit selectin-mediated cellular adhesion, compositions containing and processes for using the same, and processes for preparing those analogues.

2. Background Art

Vascular endothelial cells and blood platelets play key roles in a number of biological responses by selectively binding certain cells, for instance phagocytic leukocytes, in the bloodstream. For example, endothelial cells preferentially bind monocytes and granulocytes prior to their migration through the blood vessel wall and into surrounding tissue in an inflammatory response.

Certain inflammation-triggering compounds are known to act directly on the vascular endothelium to promote the adhesion of leukocytes to vessel walls. Cells then move through the walls and into areas of injury or infection.

Cellular adhesion to vascular endothelium is also thought to be involved in tumor metastasis. Circulating cancer cells apparently take advantage of the body's normal inflammatory mechanisms and bind to areas of blood vessel walls where the endothelium is activated.

Blood platelets are also involved in similar responses. Platelets are known to become activated during the initiation of hemostasis and undergo major morphological, biochemical, and functional changes (e.g., rapid granule exocytosis, or degranulation), in which the platelet alpha granule membrane fuses with the external plasma membrane. As a result, new cell surface proteins become expressed that confer on the activated platelet new functions, such as the ability to bind both other activated platelets and other cells. Activated platelets are recruited into growing thrombi, or are cleared rapidly from the blood circulation. Activated platelets are known to bind to phagocytic leukocytes, including monocytes and neutrophils. Examples of pathological and other biological processes that are thought to be mediated by this process include atherosclerosis, blood clotting and inflammation.

Recent work has revealed that specialized cell surface receptors on endothelial cells and platelets, designated E-selectin (endothelial leukocyte adhesion molecule-1; ELAM-1) and P-selectin (granule membrane protein-140; GMP-140), respectively, are involved in the recognition of various circulating cells by the endothelium and platelets. For example, E-selectin has been shown to mediate endothelial leukocyte adhesion, which is the first step in many inflammatory responses. Specifically, E-selectin binds human neutrophils, monocytes, eosinophils, certain T-lymphocytes [Graber et al., J. Immunol., 145:819 (1990)], NK cells, and the promyelocytic cell line HL-60.

E-selectin is inducibly expressed on vascular endothelial cells [Bevilacqua et al., Science, 243:1160–1165 (1989) and Hession et al., Proc. Natl. Acad. Sci., 87:1673–1677 (1990)]. This receptor has been demonstrated to be induced by inflammatory cytokines such as interleukin 1β (IL-1β) and tumor necrosis factor α (TNFα), as well as bacterial endotoxin (lipopolysaccharide) [Bevilacqua et al., Proc. Natl. Acad. Sci., 84:9238–9242 (1987)]. These compounds augment polymorphonuclear leukocyte (neutrophil), and monocyte adhesion [Bevilacqua et al., Proc. Natl. Acad. Sci., 84:9238–9242 (1987)].

P-selectin (also known as GMP-140 and PADGEM) is present on the surface of platelets and endothelial cells, where it mediates platelet-leukocyte and endothelium-leukocyte interactions, [Geng et al., Nature, 343:757–760 (1990)]. Thus, for example, activated platelets that express P-selectin on their surface are known to bind to monocytes and neutrophils [Jungi et al., Blood, 67:629–636 (1986)], and also to bind monocyte-like cell lines, e.g., HL-60 and U937 [Jungi et al., Blood, 67:629–636 (1986); Silverstein et al., J. Clin. Invest., 79:867–874 (1987)].

P-selectin is an alpha granule membrane protein of molecular mass 140,000 that is expressed on the surface of activated platelets upon platelet stimulation and granule secretion [Hsu-Lin et al., J. Clin. Chem., 259:9121–9126 (1984); Stenberg et al., J. Cell Biol., 101:880–886 (1985); Berman et al., J. Clin. Invest., 78:130–137 (1986)]. It is also found in megakaryocytes [Beckstead et al., Blood, 6.7:285–293 (1986)], and in endothelial cells [McEver et al., Blood, 70:335a (1987)] within the Weibel-Palade bodies [Bonfanti et al., Blood, 73:1109–1112 (1989)]. Furie et al., U.S. Pat. No. 4,783,330, describe monoclonal antibodies reactive with P-selectin.

A third receptor is the lymphocyte homing receptor, MEL-14 antigen or its human counterpart LAM-1 (L-selectin) [Gallatin et al., Nature, 304:30–34 (1983); Siegellman et al., Science, 243:1165–1172 (1989); Rosen, Cell Biology, 1:913–919 (1989); and Lasky et al., Cell, 56:1045–1055 (1989)]. In addition to lymphocyte homing, MEL-14 antigen/LAM-1 is believed to function early in neutrophil binding to the endothelium.

The term "selectin" has been suggested for a general class of receptors, which includes E-selectin (ELAM-1), P-selectin (GMP-140) and L-selectin (MEL-14), because of their lectin-like domain and the selective nature of their adhesive functions. The structure and function of selectin receptors has been elucidated by cloning and expression of full length cDNA encoding each of the above receptors [Bevilacqua et al., Science, 243:1160–1165 (1989), (ELAM-1); Geng et al., Nature, 343:757–760 (1990), (GMP-140); and Lasky et al., Cell, 56:1045–1055 (1989), (MEL-14 antigen)].

The extracellular portion of selectins can be divided into three segments based on homologies to previously described proteins. The N-terminal region (about 120 amino acids) is related to the C-type mammalian lectin protein family as described by Drickamer, J. Biol. Chem., 263:9557–9560 (1988) that induces low affinity IgE receptor CD23. A polypeptide segment follows, which has a sequence that is related to proteins containing the epidermal growth factor (EGF) motif. Lastly, after the EGF domain are one or more tandem repetitive motifs of about 60 amino acids each, related to those found in a family of complement regulatory proteins.

U.S. Pat. No. 5,079,353 and its divisional U.S. Pat. No. 5,296,594 teach the synthesis and use of the sialyl Le$^x$ and sialyl Le$^a$ antigens that are present in cancerous tissues, and are ligands for the before-described selectin receptors. U.S. Pat. No. 5,143,712 teaches the binding iterations between various receptors such as ELAM-1 (E-selectin) and ligands such as sialyl Le[x] as well as ligands containing a plurality of N-acetyllactosamine (LacNAc) units along with a terminal sialyl group and one or more fucosyl groups that are bonded to the GlcNAc portion of a LacNAc unit.

Published International application WO 91/19501 and WO 91/19502 disclose that oligosaccharides containing the pentameric and hexameric structures shown below inhibited selective cellular binding between cells containing the ligand (below) and those containing a selectin receptor, and that the penta- and hexasaccharides assayed provided better inhibition than did SLe[x].

NeuAcα2→3Galβ1→4(Fucα1→3)GlcNAcβ1,3Galβ-;

NeuAcα2→3Galβ1→4(Fucα1→3)GlcNAcβ1,3Galβ1, 4Glc-; and

NeuAcα2→3Galβ1→4(Fucα1→3)GlcNAc=SLe[x].

BRIEF SUMMARY OF THE INVENTION

The present invention contemplates a sialyl Le[x] (SLe[x]) analogue compound that inhibits the adhesion of cells that express SLe[x] on their surfaces to a selectin receptor, an intermediate compound in the synthesis of an inhibitor, as well as a process for preparing an intermediate and a composition containing an inhibitor.

A contemplated compound corresponds to the formula

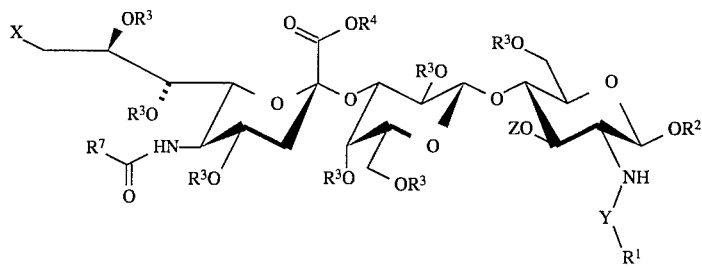

wherein

Z is hydrogen, $C_1$–$C_6$ acyl or

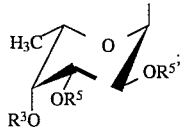

Y is selected from the group consisting of C(O), $SO_2$, HNC(O), OC(O) and SC(O);

$R^1$ is selected from the group consisting of an aryl, a substituted aryl and a phenyl $C_1$–$C_3$ alkylene group, wherein an aryl group has one five- or six-membered aromatic ring, fused five/six-membered aromatic rings, or two fused six-membered aromatic rings, which rings are selected from the group consisting of hydrocarbyl, monooxahydrocarbyl, monothiahydrocarbyl, monoazahydrocarbyl and diazahydrocarbyl rings, and a substituted aryl group is a before-mentioned aryl group having a substituent selected from the group consisting of a halo, trifluoromethyl, nitro, $C_1$–$C_{18}$ alkyl, $C_1$–$C_{18}$ alkoxy, amino, mono-$C_1$–$C_{18}$ alkylamino, di-$C_1$–$C_{18}$ alkylamino, benzylamino, $C_1$–$C_{18}$ alkylbenzylamino, $C_1$–$C_{18}$ thioalkyl and $C_1$–$C_{18}$ alkyl carboxamido groups, or $R^1Y$ is allyloxycarbonyl or chloroacetyl;

$R^2$ is selected from the group consisting of hydrogen, $C_1$–$C_{18}$ straight chain, branched chain or cyclic hydrocarbyl, $C_1$–$C_6$ alkyl $C_1$–$C_5$ alkylene ω-carboxylate, ω-tri($C_1$–$C_4$ alkyl/phenyl)silyl $C_2$–$C_4$ alkylene, monosaccharide and disaccharide, or $OR^2$ together form a $C_1$–$C_{18}$ straight chain, branched chain or cyclic hydrocarbyl carbamate;

$R^3$ is hydrogen or $C_1$–$C_6$ acyl;

$R^4$ is hydrogen, $C_1$–$C_6$ alkyl or benzyl;

$R^5$ is selected from the group consisting of hydrogen, benzyl, methoxybenzyl, dimethoxybenzyl and $C_1$–$C_6$ acyl;

$R^7$ is methyl ($CH_3$) or hydroxymethyl ($CH_2OH$); and

X is selected from the group consisting of $C_1$–$C_6$ acyloxy, $C_2$–$C_6$ hydroxylacyloxy, hydroxy, halo and azido.

Y is preferably carbonyl [C(O)].

For one group of inhibitors, $R^2$ is preferably a monosaccharide and more preferably a $C_1$–$C_{18}$ alkyl glycoside of a monosaccharide, $R^7$ is methyl, Z is an unprotected fuco group, X is hydroxyl and $R^1Y$ is other than allyloxycarbonyl or chloroacetyl. An intermediate to an inhibitor can have any of the illustrated "R" groups, with $R^3$, $R^4$ and $R^5$ preferably being other than hydrogen.

A particularly preferred inhibitor corresponds to the formula

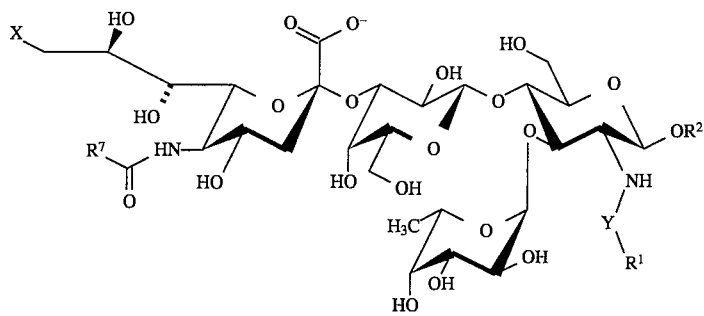

wherein $R^1$ is as above, and $R^1Y$ is other than allyloxycarbonyl or chloroacetyl, X is as above and preferably other than $C_1$–$C_6$ acyloxy and $C_1$–$C_6$ hydroxylacyloxy, and $R^2$ and $R^7$ are as discussed above. In one embodiment, $R^2$ is preferably other than mono- or disaccharide. A benzyl $R^2$ group is particularly preferred here.

Another group of particularly preferred inhibitors corresponds to the formula

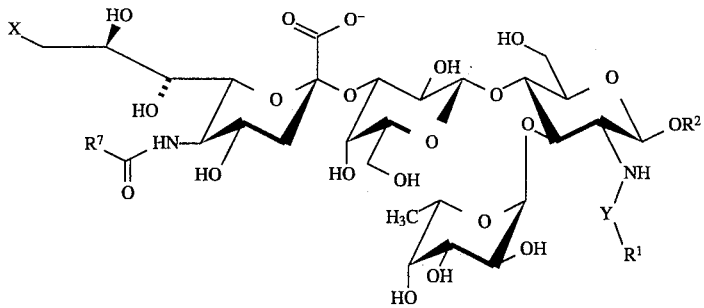

wherein $R^1$ is as above except allyloxycarbonyl and chloroacetyl $R^1Y$ groups are excluded, X is as above and preferably other than $C_1$–$C_6$ acyloxy and $C_1$–$C_6$ hydroxylacyloxy, $R^7$ is as before, and $R^2$ is a mono- or disaccharide.

A pharmaceutical composition is also contemplated. That pharmaceutical composition comprises a pharmaceutically acceptable diluent or carrier having dissolved or dispersed therein a cellular adhesion-inhibiting amount of a compound of the formula

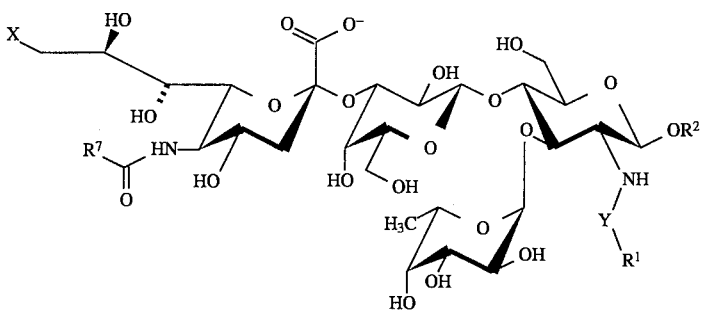

wherein

Y is selected from the group consisting of C(O), $SO_2$, HNC(O), OC(O) and SC(O);

$R^1$ is as defined before, and is preferably selected from the group consisting of an aryl, substituted aryl and a phenyl $C_1$–$C_3$ alkylene group, wherein an aryl group is selected from the group consisting of furyl, thienyl, phenyl, naphthyl, pyridyl, pyrazinyl, benzofuranyl, isobenzofuranyl, benzo [b or c] thienyl, pyrimidinyl, pyridazinyl, quinolinyl, isoquinolinyl, quinoxalinyl, naphthyridinyl, phthalazinyl and quinazolinyl, and a substituted aryl group is a before-mentioned aryl group having a substituent selected from the group consisting of halo, trifluoromethyl, nitro, $C_1$–$C_8$ alkyl, $C_1$–$C_{18}$ alkoxy, amino, mono-$C_1$–$C_{18}$ alkylamino, di-$C_1$–$C_{18}$ alkylamino, benzylamino and $C_1$–$C_{18}$ alkylbenzylamino;

$R^2$ is selected from the group consisting of hydrogen, $C_1$–$C_{18}$ straight chain, branched chain or cyclic hydrocarbyl, $C_1$–$C_6$ alkyl $C_1$–$C_5$ alkylene ω-carboxylate, ω-tri($C_1$–$C_4$ alkyl/phenyl)silyl $C_2$–$C_4$ alkylene, monosaccharide and disaccharide, or $OR^2$ together form a $C_1$–$C_{18}$ straight chain, branched chain or cyclic hydrocarbyl carbamate;

$R^7$ is methyl ($CH_3$) or hydroxymethyl ($CH_2OH$); and

X is selected from the group consisting of $C_1$–$C_6$ acyloxy, $C_2$–$C_6$ hydroxylacyloxy, hydroxy, halo or azido.

The above noted preferences for an inhibitor are maintained for a pharmaceutical composition.

A process of preparing lactosammonium salt is further contemplated. This process comprises the steps of:

(a) admixing lactulose with a primary amine that is a monosubstituted ammonia derivative whose nitrogen atom is bonded to a reductively removable blocking group such as benzylamine to form a reaction mixture. The primary amine serves as both reactant and solvent or primary solvent, and is present in an amount that is about 2 to about 10 times the molar amount of lactulose, preferably in about 4- to about 8-fold molar excess.

(b) The reaction mixture is maintained at a temperature of about 10° C. to about 60° C., and preferably about room temperature to about 50° C., for a time period sufficient for the corresponding lactulose N-glycoside to form. This maintenance time can vary from about 2 to about 7 days where maximal yields are desired.

(c) The formed lactulose N-glycoside is reacted with up to an equivalent amount of a carboxylic acid having a $pK_a$ value of about 2.5 to about 5.0 in a $C_1$–$C_3$ alcohol solvent such as methanol at a temperature of about 10° C. to about 30° C. to rearrange the lactulose N-glycoside into an amine-blocked lactosammonium salt having a reductively removable blocking group bonded to the amine. The lactulose N-glycoside can be present at about 0.1M to about the saturation level; and (d) The blocking group is then reductively removed as by hydrogenolysis from said amine-blocked lactosammonium salt to form the lactosammonium salt. That salt is preferably recovered.

The nomenclature used to describe the oligosaccharide moieties of the present invention follows the conventional nomenclature. Standard abbreviations for individual monosaccharides are used. For instance, 2-N-acetylglucosamine is represented by GlcNAc, 2-N-acetylgalactosamine is GalNAc, fucose is Fuc, fructose is Fru, galactose in Gal, glucose is Glc, and mannose is Man. Unless otherwise indicated, all sugars except fucose (L-isomer) are D-isomers in the cyclic configuration (e.g., pyranose or furanose). The two anomers of the cyclic forms are represented by $\alpha$ and $\beta$.

The monosaccharides are generally linked by glycosidic bonds to form oligo- and polysaccharides. The orientation of the bond with respect to the plane of the rings is indicated by $\alpha$ and $\beta$. The particular carbon atoms that form the bond between the two monosaccharides are also noted. Thus, a $\beta$ glycosidic bond between C-1 of galactose and C-4 of glucose is represented by Gal$\beta$1→4Glc. For the D-sugars (e.g., D-GlcNAc, D-Gal, D-NeuAc and D-Man) the designation $\alpha$ means the hydroxyl attached to C-1 (C-2 in NeuAc) is below the plane of the ring and $\beta$ is above the ring. In the case of L-fucose, the $\alpha$ designation means the hydroxyl is above the ring and $\beta$ means it is below.

DETAILED DESCRIPTION OF THE INVENTION

A. The Compounds

The present invention contemplates a SLe$^x$ analogue compound of structural Formula A, below, which structural formula encompasses a pentasaccharide compound of Formula I that is an analogue of sialyl Le$^x$, as well as its penta- and tetrasaccharide precursors of Formulas II and III, respectively. A compound of structural Formula I inhibits cellular adhesion mediated by a selectin cell surface receptor.

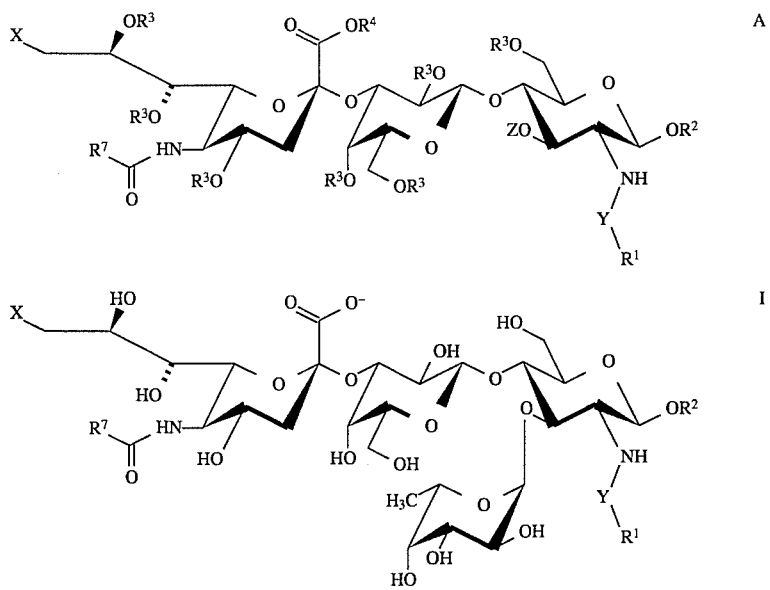

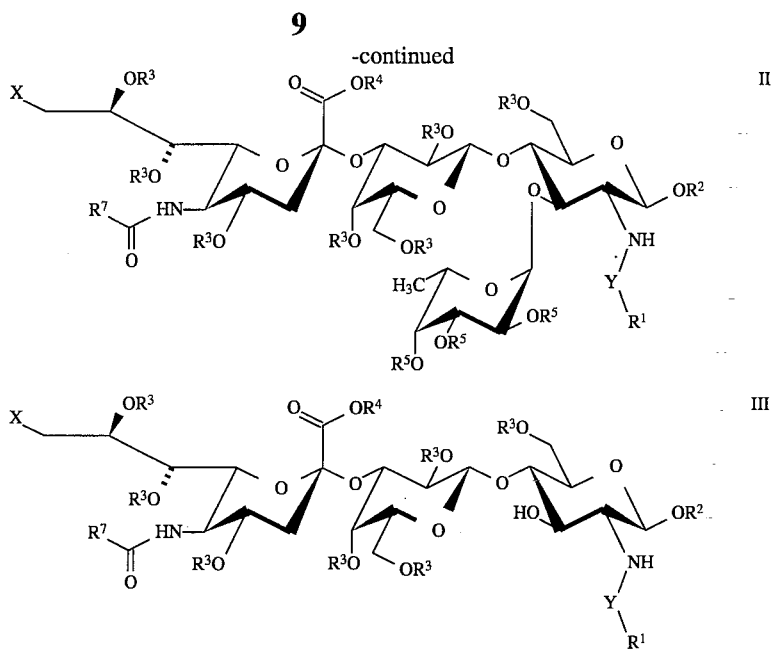

In the above structural formulas,

Z is hydrogen (H) or $C_1$–$C_6$ acyl, in which case a compound of Formula III is defined, or an α-L-fucosyl whose hydroxyl groups are free or blocked with a protecting group (benzyl or $C_1$–$C_6$ acyl) thereby defining a compound of Formula I or II, depending upon the identities of $R^3$, $R^4$ and $R^5$ ($R^{3-5}$) groups;

Y is selected from the group consisting of C(O), $SO_2$, HNC(O), OC(O) and SC(O);

$R^1$ is selected from the group consisting of an aryl, a substituted aryl and a phenyl $C_1$–$C_3$ alkylene group, wherein an aryl group has one five- or six-membered aromatic ring, fused five/six-membered aromatic rings, or two fused six-membered aromatic rings, which rings are selected from the group consisting of hydrocarbyl, monooxahydrocarbyl, monothiahydrocarbyl, monoazahydrocarbyl and diazahydrocarbyl rings, and a substituted aryl group is a before-mentioned aryl group having a substituent selected from the group consisting of a halo, trifluoromethyl, nitro, $C_1$–$C_{18}$ alkyl, $C_1$–$C_{18}$ alkoxy, amino, mono-$C_1$–$C_{18}$ alkylamino, di-$C_1$–$C_{18}$ alkylamino, benzylamino, $C_1$–$C_{18}$ alkylbenzylamino, $C_1$–$C_{18}$ thioalkyl and $C_1$–$C_{18}$ alkyl carboxamido group, or $R^1Y$ is allyloxycarbonyl or chloroacetyl;

$R^2$ is selected from the group consisting of hydrogen, $C_1$–$C_{18}$ straight chain, branched chain or cyclic hydrocarbyl, $C_1$–$C_6$ alkyl $C_1$–$C_5$ alkylene ω-carboxylate, ω-tri($C_1$–$C_4$ alkyl/phenyl)silyl $C_2$–$C_4$ alkylene, monosaccharide and disaccharide, or $OR^2$ together form a $C_1$–$C_{18}$ straight chain, branched chain or cyclic hydrocarbyl carbamate;

$R^3$ is hydrogen or $C_1$–$C_6$ acyl;

$R^4$ is hydrogen, $C_1$–$C_6$ alkyl or benzyl;

$R^5$ is selected from the group consisting of hydrogen, benzyl, methoxybenzyl, dimethoxybenzyl and $C_1$–$C_6$ acyl;

$R^7$ is methyl ($CH_3$) or hydroxymethyl ($CH_2OH$); and

X is selected from the group consisting of $C_1$–$C_6$ acyloxy, $C_2$–$C_6$ hydroxylacyloxy, hydroxy, halo and azido.

As noted above, Y can be one of a number of groups. When Y is C(O), $R^1Y$ is an acyl substituent group so that an amide is formed with the saccharide amine nitrogen atom. When Y is $SO_2$, $R^1Y$ forms a sulfonyl substituent group so that a sulfonamide is formed with the saccharide amine nitrogen atom. When Y is HNC(O), $R^1Y$ forms an aminocarbonyl substituent group so that a urea substituent is formed with that saccharide nitrogen atom. A urethane substituent is formed with the saccharide amine nitrogen where Y is oxycarbonyl, OC(O), whereas a thiourethane is formed where Y is thiocarbonyl, SC(O). A Y group is preferably a carbonyl group [C(O)].

An $R^1Y$ group can also be an allyloxycarbonyl or a chloroacetyl group. An allyloxycarbonyl $R^1Y$ group is particularly preferred for a compound of Formula III as it provides a readily replaceable $R^1$ group. An $R^1Y$ allyloxycarbonyl or chloroacetyl group is present only in a compound of Formula III, and is not present in a compound of any of Formulas I, II, A, B or C (Formulas B and C are shown hereinafter).

As discussed before, an $R^1$ group can be an aryl or substituted aryl group. Contemplated aryl groups are those that contain one aromatic five- or six-membered ring, fused five- and six- (five/six-) membered rings or two fused aromatic six-membered rings and include hydrocarbyl groups such as phenyl and naphthyl, as well as hydrocarbyl groups bearing an oxygen, a sulfur, or one or two nitrogen atoms that replace ring carbon atoms (mono- or diazahydrocarbyl). Exemplary aryl groups include furyl, thienyl, pyridyl, pyrazinyl, benzofuranyl (benzo[b]furyl), isobenzofuranyl (benzo[c]furyl), benzothienyl (benzo[b]thienyl), isobenzothienyl (benzo[c]thienyl), pyrimidinyl, pyridazinyl, quinolinyl, isoquinoyl, quinoxalinyl, naphthyridinyl, phthalazinyl and quinazolinyl. Each of those aryl groups can be unsubstituted, or each can have a substituent selected from the group consisting of halo, trifluoromethyl, nitro, $C_1$–$C_{18}$ alkyl, $C_1$–$C_{18}$ alkoxy, amino, mono-$C_1$–$C_{18}$ alkylamino, di-$C_1$–$C_{18}$ alkylamino, $C_1$–$C_{18}$ alkylbenzylamino and $C_1$–$C_{18}$ alkyl carboxamido.

The above unsubstituted and substituted aryl $R^1$ groups are well known in the art, and each can be bonded to the saccharide nitrogen atom using well known chemistry. The following discussion will therefore center upon aryl hydrocarbyl groups, phenyl and naphthyl, as being exemplary of the group, with the understanding that the other enumerated aryl and substituted aryl $R^1$ groups can be utilized with substantially similar chemistry.

Where $R^1$ is phenyl, benzoyl chloride or benzoic anhydride can be used to form a preferred amide bond. A benzenesulfonyl halide such as benzenesulfonyl chloride can similarly be used where Y is $SO_2$. Phenyl isocyanate is used where Y is HNC(O). A phenyl chloroformate is used where Y is OC(O), whereas a phenyl chlorothioformate is used where Y is SC(O).

Specifically contemplated substituted phenyl $R^1$ groups include those in which the substituent can be substituted at any position of the ring, with the meta and para positions being preferred. Mono-substituted $R^1$ phenyl groups are preferred over di-substituted groups.

Contemplated halo substituents include fluoro, chloro, bromo and iodo groups, with p-fluorophenyl, m-chlorophenyl, m-iodophenyl, p-bromophenyl and o-fluorophenyl being exemplary. Dihalo-substituted phenyl $R^1$ groups are also contemplated such as 3,4-dichlorophenyl, 3,5-dichlorophenyl, 2-chloro-4-fluorophenyl and 3-bromo-4-fluorophenyl.

Exemplary $C_1$–$C_{18}$ alkyl groups present as substituent groups on a phenyl of $R^1$ include straight and branched chain alkyl groups such as methyl, ethyl, propyl, iso-propyl, butyl, isobutyl, t-butyl, pentyl, hexyl, octyl, nonyl, decyl, dodecyl, tetradecyl, hexadecyl and octadecyl. $C_1$–$C_{12}$ Alkyl groups are preferred, whereas $C_1$–$C_6$ alkyl groups are particularly preferred, with methyl being most preferred. Exemplary, preferred $R^1$ groups include o-, m- and p-tolyl (methylphenyl) and p-t-butylphenyl groups as well as 3,4-dimethylphenyl and 3,5-dimethylphenyl groups.

Exemplary $C_1$–$C_{18}$ alkoxy groups are ethers containing a $C_1$–$C_{18}$ alkyl group, or a particularly preferred $C_1$—$C_6$ alkyl group. Methoxy is preferred here. Exemplary, preferred $R^1$ groups include o, m- and p- anisyl (methoxyphenyl), as well as 3,4-dimethoxyphenyl and 3,5-dimethoxyphenyl.

A nitrophenyl $R^1$ group is readily prepared by acylation using 3- or 4-nitrobenzoyl chloride. Acylation with 3,4- and 3,5-dinitrobenzoyl chloride provides the corresponding 3,4- and 3,5-dinitrophenyl $R^1$ groups. Amide formation using 3- or 4-trifluoromethylbenzoyl chloride similarly provides 3- or 4-trifluoromethylphenyl $R^1$ groups.

A substituted phenyl $R^1$ group can also contain an amino, mono-$C_1$–$C_{18}$ alkylamino, di-$C_1$–$C_{18}$ alkylamino, benzylamino, $C_1$–$C_{18}$ alkylbenzylamino or $C_1$–$C_{18}$ alkyl carboxamido substituent, wherein $C_1$–$C_{18}$ alkyl substituents are as discussed before.

Aminophenyl $R^1$ groups are most readily prepared from corresponding nitrophenyl $R^1$ groups discussed before by catalytic reduction of the nitro group after formation of the amide bond, as discussed before. Thus, for example, use of 3- or 4-nitrobenzoyl chloride to form the amide bond, upon reduction with palladium on carbon forms the corresponding 3- or 4-aminophenyl $R^1$ group. A similar use of 3,4- or 3,5-dinitrobenzoyl chloride provides the corresponding 3,4- or 3,5-diaminophenyl $R^1$ group after reduction.

Several di-$C_1$–$C_6$ alkylaminobenzoic acids such as 4-diethylaminobenzoic acid and 3- and 4-dimethylaminobenzoic acids can be purchased commercially and used to form an appropriate benzoyl halide or anhydride for forming an $R^1$-containing amide. The remaining di-$C_1$–$C_{18}$ alkylaminobenzoic acids and those compounds having two dialkylamino groups can be prepared using well known alkylation techniques from corresponding aminobenzoic acids or diaminobenzoic acids that are also commercially available.

A mono-$C_1$–$C_{18}$ alkylaminophenyl $R^1$ group can be prepared from the corresponding mono-$C_1$–$C_{18}$ alkylaminobenzoic halide, whose remaining nitrogen valence is blocked by a readily removable blocking group such as t-Boc that can be removed with acid or a benzyl group that can be removed by hydrogenation, if desired, using palladium on carbon. Thus, acylation can take place using N-benzyl-N-propylaminobenzoyl chloride, with the N-benzyl group being removed by catalytic hydrogenation to provide the mono-$C_1$–$C_{18}$ alkylaminophenyl $R^1$ group. Of course, the benzyl group need not be removed, thereby providing a $C_1$–$C_{18}$ alkylbenzylamino group.

Each of the above-discussed phenyl or substituted phenyl substituents can be prepared by a well known amide-forming reaction. An exemplary reaction reacts an appropriate benzoyl halide or anhydride such as p-fluorobenzoyl chloride or benzoic anhydride with the unprotected amine group of an otherwise protected saccharide as is illustrated in detail hereinafter.

Both 1- and 2-naphthyl $R^1$ groups are contemplated, with 2-naphthyl being particularly preferred. These compounds can also be prepared using standard amide-forming technology as above, such as by reacting 2-naphthoyl chloride with an amine of an appropriate saccharide as discussed above.

It is to be understood that similar substituents are present on the oxa-, thia-, aza- and diazahydrocarbyl aryl groups. For example, one can utilize any of the two furoic acid chlorides, the two thiophenecarboxyl chlorides, three pyridinecarboxyl chlorides, quinaldic acid chloride, 3-quinolinecarboxylic acid chloride, 2-quinoxaloyl acid chloride and the like to carry out an acylation reaction.

Similarly, where Y is $SO_2$, a corresponding sulfonyl halide is used. For example, one may utilize benzenesulfonyl chloride, toluenesulfonyl chloride, 8-quinolinesulfonyl chloride, 1- or 2-naphthalenesulfonyl chloride, and the like to form the sulfonamide.

Where Y is HNC(O), the isocyanate corresponding to a before-described carboxylic acid is a convenient reactant. Such derivatives can be readily prepared from the acid halide by reaction with azide, to form the acyl azide, which undergoes the Curtius rearrangement to form the isocyanate upon heating.

Where Y is OC(O) or SC(O), a hydroxyl or mercapto substituted aryl $R^1$ group is reacted with phosgene to form the chloroformate or chlorothioformate that can be reacted with the saccharide amine to form the urethane or thiourethane linkage to an $R^1$.

A phenyl $C_1$–$C_3$ alkylene $R^1$ group is a $C_1$–$C_3$ alkylene group that is itself substituted with a phenyl group, preferably at the terminal hydrocarbyl group carbon. This $R^1C(O)$ group thus contains a phenyl ring linked to a chain of 2–4 carbon atoms. Exemplary $C(O)R^1$ alkylene groups include 2-phenylacetoyl, 3-phenylpropionyl and 4-phenylbutanoyl [$\phi CH_2C(O)$, $\phi CH_2CH_2C(O)$ and $\phi(CH_2)_3C(O)$, respectively, where $\phi$=phenyl]. These compounds can be prepared by reaction of an appropriate acid halide or anhydride with a saccharidal amine as above. Catalytic reduction using hydrogen and a palladium on carbon catalyst can be used to form saturated alkylene groups from the unsaturated hydrocarbyl chains; saturated hydrocarbyl chains being preferred.

An $R^2$ group forms a β-glycoside with the saccharide ring system. That glycoside bond can be formed from a simple $C_1$–$C_{18}$ hydrocarbyl alcohol, from an ω-hydroxycarboxylic acid ester, from an ω-hydroxylated silylated alkyl group, or from a mono- or a disaccharide, or $OR^2$ together form a $C_1$–$C_{18}$ straight chain, branched chain or cyclic hydrocarbyl carbamate. A $C_1$–$C_6$ hydrocarbyl group such as ethyl, a benzyl group or a monosaccharide such as 3-galactosyl is particularly preferred. $R^2$ can also be hydrogen.

Exemplary $R^2$ groups formed from simple precursor alcohol groups include $C_1$–$C_{18}$ straight chain, branched chain or cyclic hydrocarbyl groups. Illustrative of such groups are the before-described $C_1$–$C_6$ alkyl groups, which are preferred, as well as their unsaturated counterparts, such as allyl, 3-butenyl, 2-but-3-enyl, and but-3-ynyl, as well as longer hydrocarbyl groups such as benzyl, 4-methylcyclohexyl, decahydronaphthyl, nonyl, decyl (capryl), dodecyl (lauryl), dodec-7-enyl, myristyl, palmityl, stearyl, oleyl, linoleyl, linolenyl and ricinoleyl.

Exemplary mono- and disaccharides include 3- and 4-glucosyl (3/4Glc), 3- and 4-galactosyl (3/4Gal), a 3-galactosyl group being particularly preferred, 3- and 4-N-acetylglucosyl (3/4GlcNAc), 2, 3-, 4- and 6-mannosyl (2/3/4/6Man), and 3- and 6-N-acetylgalactosyl (3/6 GalNAc) and Gal$\beta$1$\rightarrow$4GlcNAc. A monosaccharide can itself form a glycoside linkage with a group, $R^6$, that includes all but a saccharide of an $R^2$ group. Thus, $R^6$ is $R^2$ other than mono- or disaccharide.

A structural formula for a particularly preferred compound of Formula A having a reducing terminal 3Gal$\beta$OR$^6$ group is shown below in structural Formula B wherein X, Y, Z and $R^{1-4}$, $R^6$ and $R^7$ are as defined before.

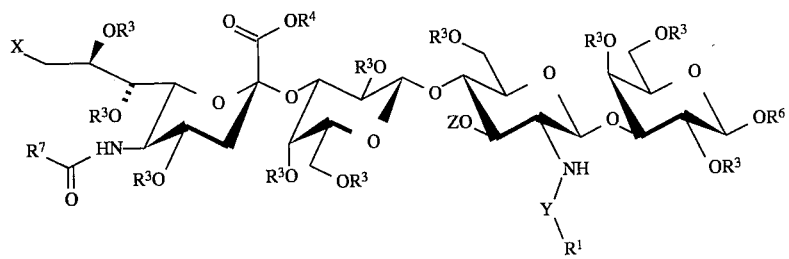

B

A $C_1$–$C_{18}$ hydrocarbyl carbamate is prepared by reaction of an isocyanate corresponding to a before discussed $C_1$–$C_{18}$ hydrocarbyl group with the hydroxyl group of the reducing end sugar. For example, the 1-hydroxyl group of a terminal glucosyl unit can be reacted with ethylisocyanate to form the corresponding ethyl carbamate (urethane). The carbonyl group of the carbamate is not included in the number of hydrocarbyl carbon atoms.

A $C_1$–$C_6$ alkyl $C_1$–$C_5$-alkylene $\omega$-carboxylate $R^2$ group is a $C_1$–$C_6$ alkyl ester of a $C_2$–$C_6$ $\omega$-carboxylic acid. Such esters are prepared from precursor $\omega$-hydroxycarboxylic A particularly preferred compound of Formula B is an inhibitor of cellular adhesion having a structure of Formula C, below, wherein X, Y, $R^1$, $R^6$ and $R^7$ are as before disclosed.

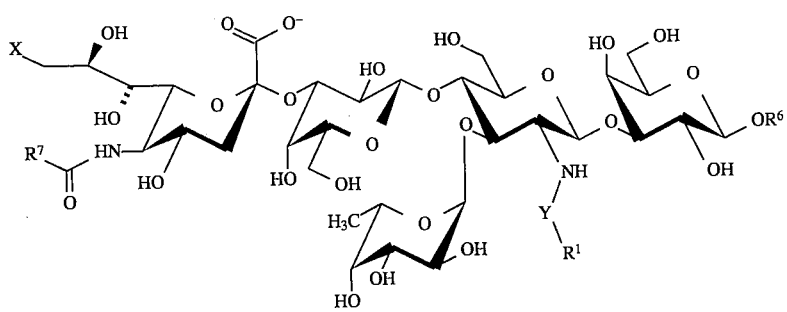

C acid esters whose hydroxyl groups are used to form the glycosidic bond. Exemplary $\omega$-hydroxycarboxylate esters include methyl 2-hydroxyacetate, ethyl 3-hydroxypropionate, t-butyl 4-hydroxybutyrate, hexyl 5-hydroxypentanoate and methyl 6-hydroxyhexanoate. Thus, the hydroxyl and carboxyl groups are at the termini of the chain and are separated by 1–5 methylene groups. Methyl 6-hydroxyhexanoate acid is preferred.

An $\omega$-tri($C_1$–$C_4$ alkyl/phenyl)silyl $C_2$–$C_4$ alkyl $R^2$ group is formed from a corresponding precursor alcohol whose substituted silyl group is at the terminus ($\omega$-position) of the chain opposite the hydroxyl group. As is well known in the art, substituted silyl groups can include many combinations of $C_1$–$C_4$ alkyl and phenyl groups such as tri-$C_1$–$C_6$ alkyl, di-$C_1$–$C_4$ alkylphenyl, $C_1$–$C_4$ alkyldiphenyl and triphenyl. Exemplary substituted silyl groups include trimethylsilyl, triphenylsilyl, di-t-butylmethylsilyl, dimethylphenylsilyl, t-butyldiphenylsilyl and the like.

The $\beta$-glycosyl bond formed with an $R^2$ or $R^6$ group can be prepared by well known organic chemical reactions with both the saccharides and other $R^2$ ($R^6$) group precursors, as by reaction of a 1-halo saccharide with a hydroxyl of a desired $R^2$ ($R^6$) group precursor alcohol in the presence of silver carbonate (Ag$_2$CO$_3$) or silver triflate, as well as by enzymatic means as with a glycosyl transferase for the saccharides.

A contemplated $R^3$ group can be hydrogen or $C_1$–$C_6$ acyl, which is the acid portion of a $C_1$–$C_6$ acyl carboxylic acid ester. A $C_1$–$C_6$ acyl group is preferred for a compound of Formula II. Exemplary $C_1$–$C_6$ acyl groups include formyl, acetyl, propionyl, butanoyl, isobutanoyl, pentanoyl and hexanoyl. An acetyl group is preferred. Acylation of saccharide hydroxyl groups is well known and can be carried out using an appropriate acid halide or anhydride.

A contemplated $R^4$ group of Formula A can be hydrogen, a $C_1$–$C_6$ alkyl, as was discussed before for such alkyl groups, or a benzyl group. An $R^4$ group along with its bonded oxygen atom forms the alcohol portion of an ester. A methyl group is preferred. The $R^4$ ester can be formed by standard means prior to the addition of the sialic acid group, after formation of the sialylated saccharide using a reagent such as diazomethane, or by reaction of a lactone with an appropriate alcohol as discussed in regard to Scheme 2, hereinafter.

The $R^4$ group of a compound of Formula III can be either a proton, $C_1$-$C_6$ alkyl or benzyl groups with $C_1$-$C_6$ alkyl being preferred. When $R^4$ is present as a proton, it is to be understood that proton can be replaced by a pharmaceutically acceptable cation (M) such as ammonium, sodium, potassium, calcium, magnesium and the like. The $R^4$ proton or other cation is typically not shown in the structures herein such as Formulas I and C because the sialyl carboxylic acid is usually ionized at physiological pH values of about 7.2–7.4 at which an inhibitor of Formulas I or C is utilized. Thus, the sialyl carboxyl group is often shown herein as a carboxylate.

An $R^5$ group is a hydrogen, a benzyl, methoxybenzyl (3- or 4-methoxybenzyl being preferred), a dimethoxybenzyl such as 3,4- or 3,5-dimethoxybenzyl, or a $C_1$-$C_6$ acyl group as discussed previously. A benzyl group is usually used where the fucosyl group is added by organic chemical synthesis.

$R^3$, $R^4$ and $R^5$ groups other than hydrogen are protecting groups used during synthesis of intermediates such as a compound of Formulas B, II and III, above. When $R^3$=$R^4$=$R^5$=H (hydrogen) a compound of Formula II becomes a compound of Formula I, whereas a compound of Formula B becomes a compound of Formula C, when Z is fuco.

Similarly, when Z is fuco and $R^3$=$R^4$=$R^5$=hydrogen, a compound of Formula A becomes a compound of Formula I.

An X substituent group can be a $C_1$-$C_6$ acyloxy group; i.e., a $C_1$-$C_6$ acyl ester of a precursor hydroxyl group at that position, a $C_2$-$C_6$ hydroxylacyloxy group, a hydroxyl group, a halo group, as discussed previously, or an azido group. Exemplary $C_1$-$C_6$ acyl groups have already been discussed, and a $C_1$-$C_6$ acyloxy group is a $C_1$-$C_6$ acyl group that further includes an additional oxygen atom bonded to the carbonyl carbon atom of an acyl group. A $C_2$-$C_6$ hydroxylacyloxy group is an above-discussed $C_1$-$C_6$ acyloxy group that further includes a substituent hydroxyl group. Exemplary $C_2$-$C_6$ hydroxylacyloxy groups include hydroxyacetate, lactate, 3-hydroxybutyrate, 2-hydroxyisovalerate and 2-hydroxycaproate. An X substituent is usually other than $C_1$-$C_6$ acyloxy or $C_2$-$C_6$ hydroxylacyloxy unless both sialylation and fucosylation are carried out enzymatically, as is discussed hereinafter.

Syntheses of sialic acid derivatives containing an X substituent are disclosed in published international application WO 92/16640 that was published on Oct.1, 1992. The use of those compounds for sialylating saccharides is also disclosed in that publication.

An $R^7$ group is methyl or hydroxymethyl, so that along with the depicted carbonyl group [C(O)] $R^7$ forms an N-acetyl or N-hydroxyacetyl group. Sialic acid derivatives containing either $R^7$ group can be used in an enzymatic sialylation as described herein.

Particularly preferred inhibitor compounds of structural Formulas I and C are illustrated below, along with their compound numbers; i.e., Compounds 17, 30–38, and 43–51.

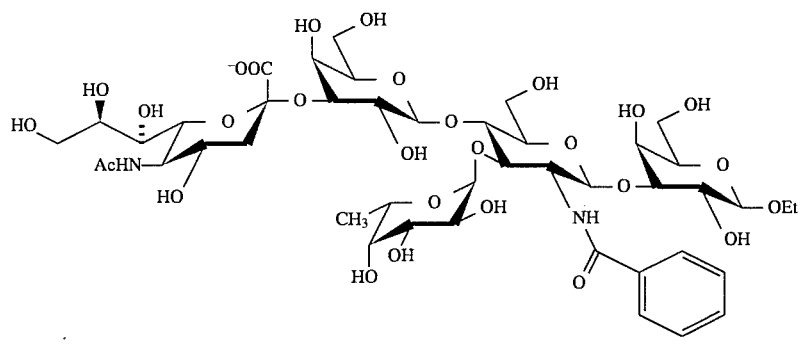

17

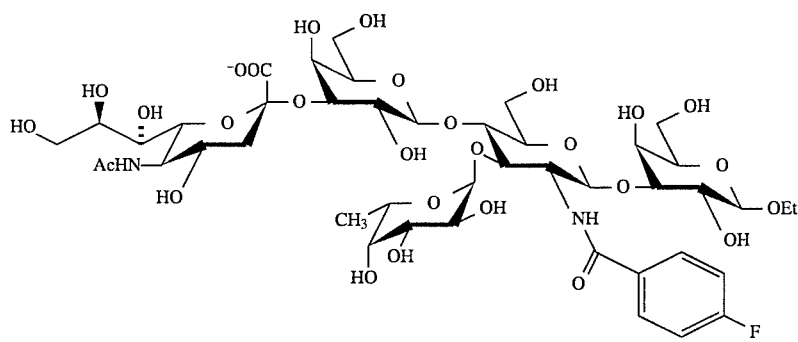

30

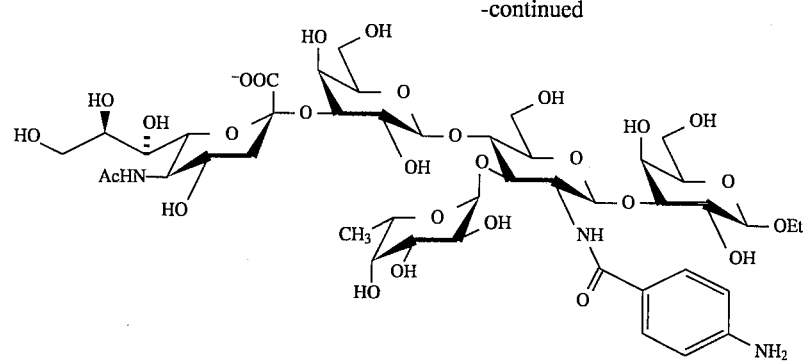
31
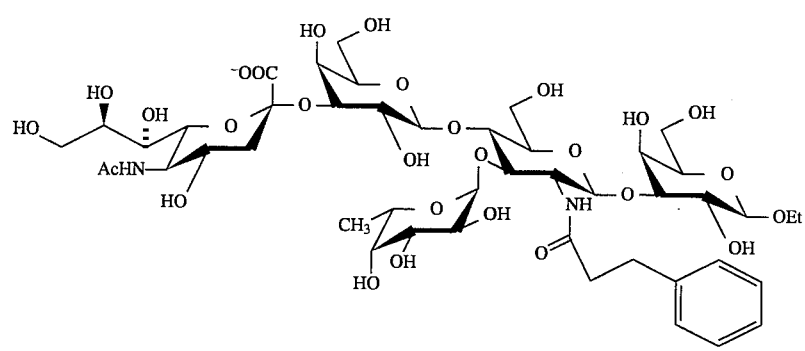
32
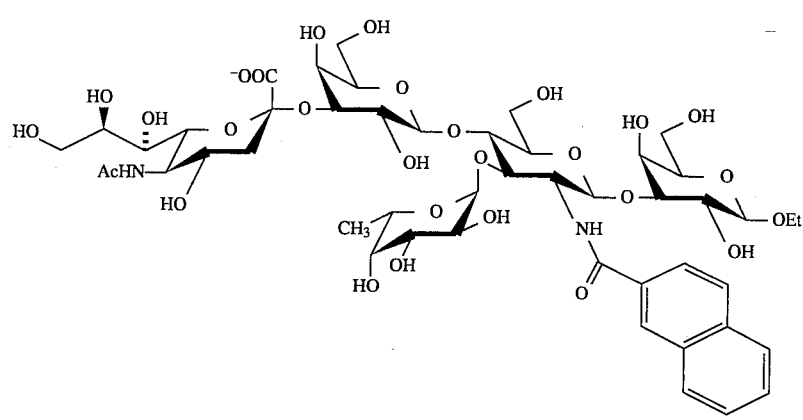
33
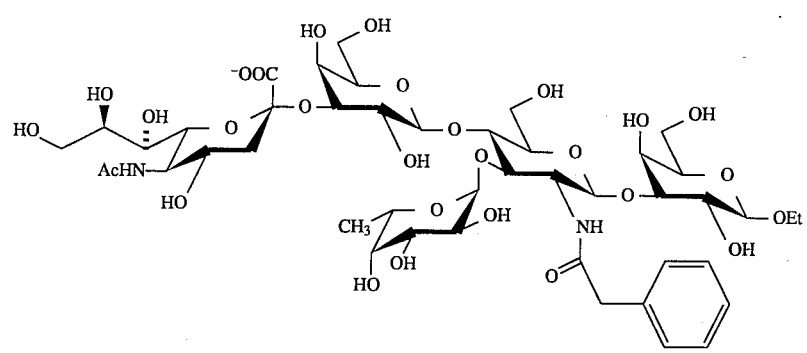
34

-continued
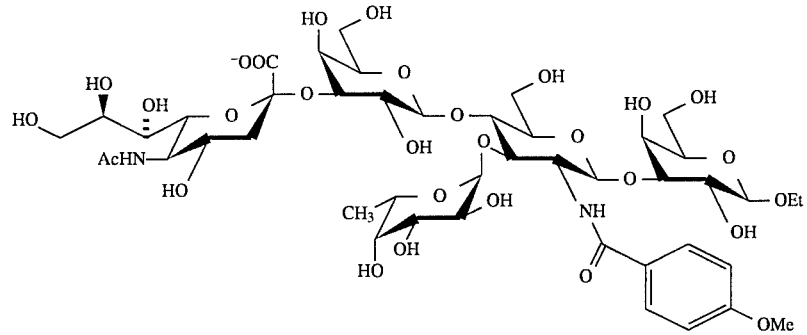
35
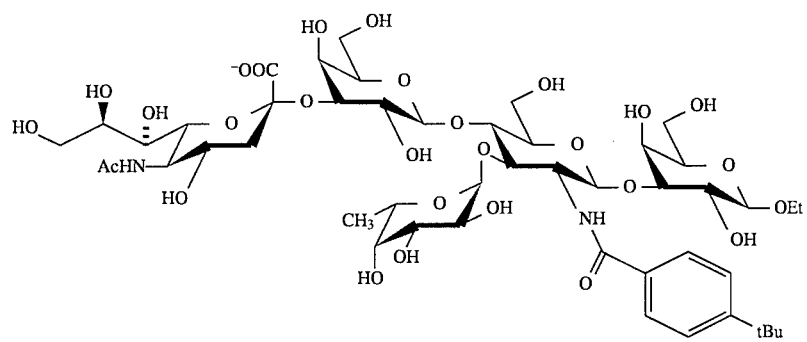
36
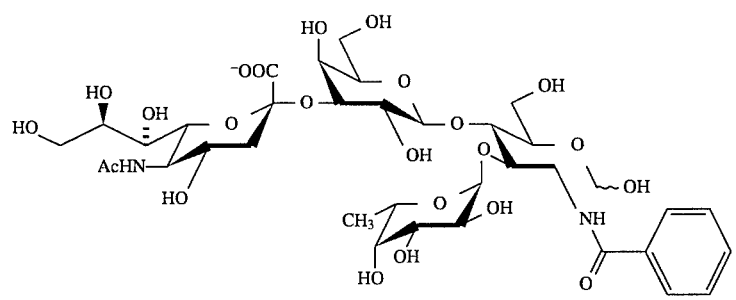
37
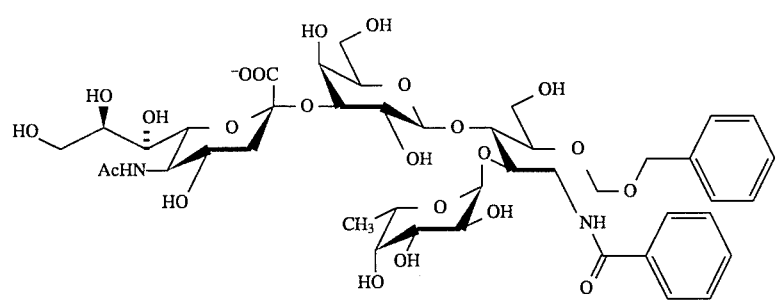
38
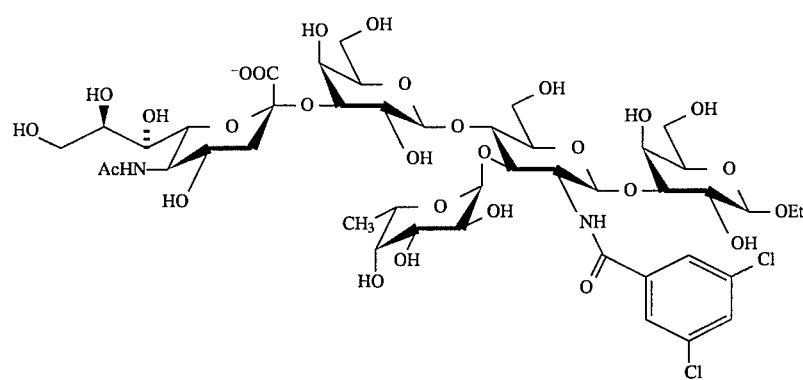
43

44
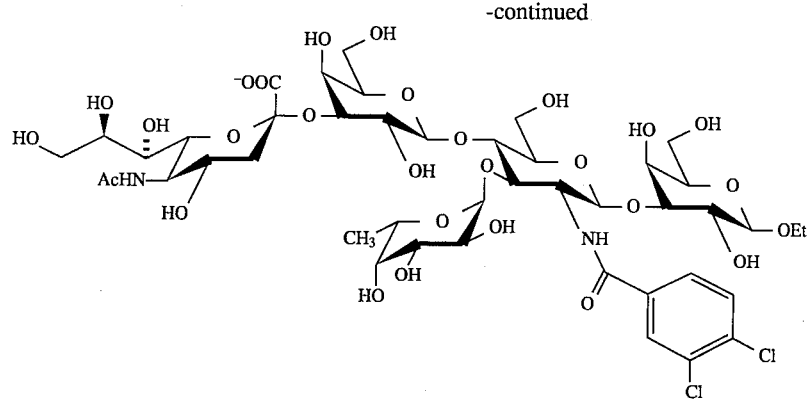
45
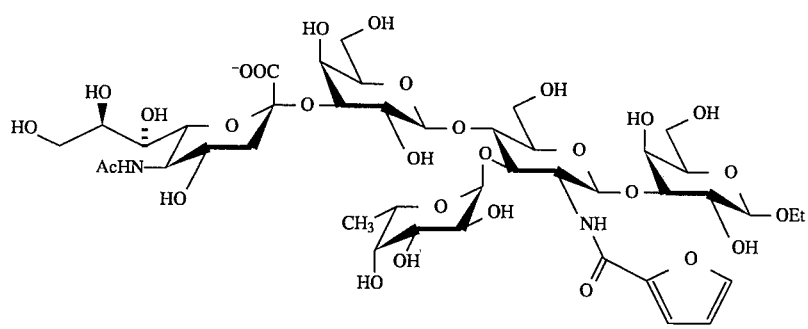
46
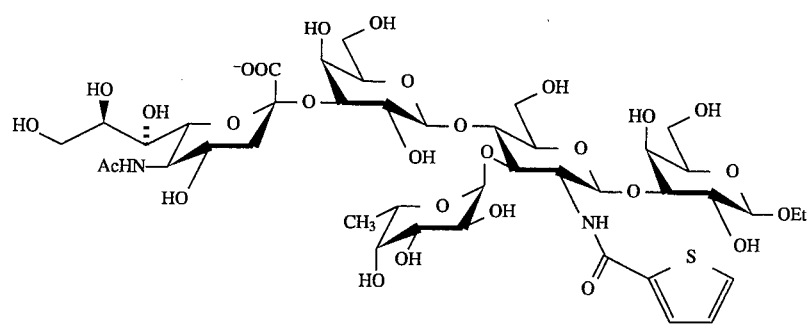
47
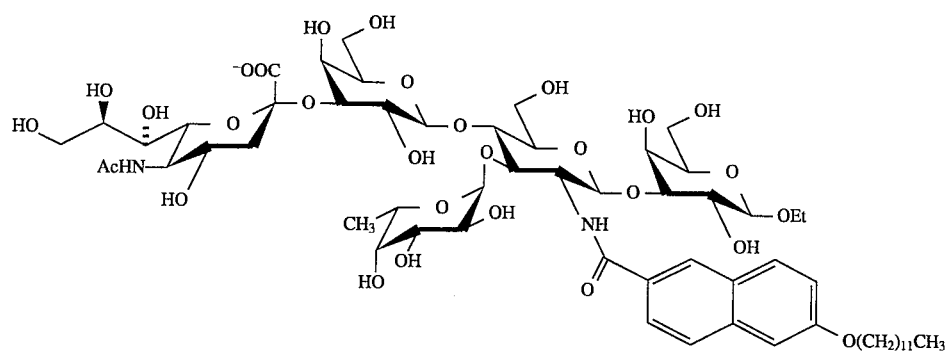

-continued

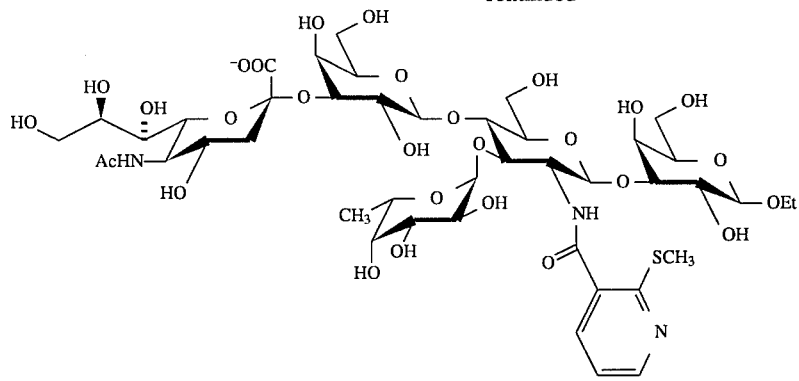
48

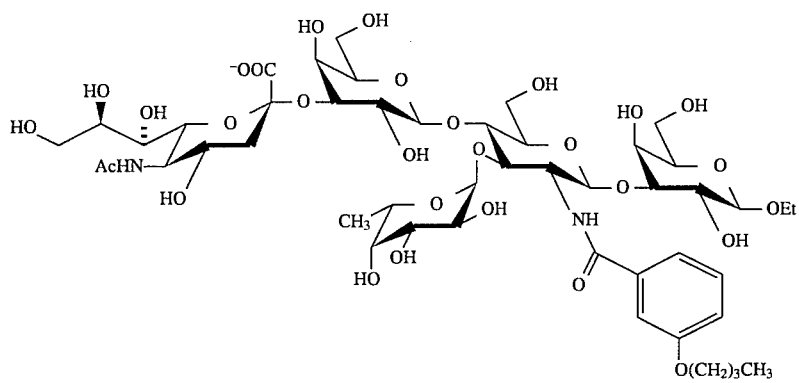
49

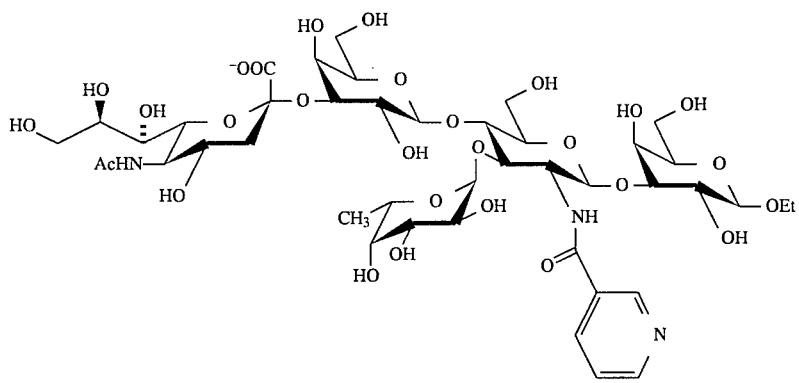
50

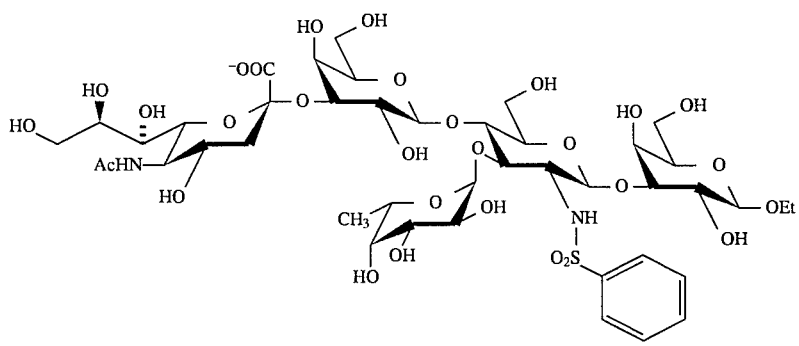
51

B. Compound Syntheses

A before-described SLe$^x$ analogue compound can be prepared in numerous ways. Thus, completely enzymatic syntheses can be carried out, syntheses using only the techniques of organic chemistry can be used, and mixtures of both organic and enzymatic syntheses can be utilized, as is exemplified here.

One way to distinguish between organic and enzymatic syntheses is by the presence of one or more enzymes in a water-based reaction medium (enzymatic synthesis), versus the absence of any enzymes coupled with a reaction medium that is substantially free of water and utilizes an organic solvent such as acetonitrile, methanol, ethanol, dimethyl formamide (DMF), dimethyl sulfoxide (DMSO), benzene, acetone, dichloromethane, tetrahydrofuran (THF) and the like (organic synthesis).

Regardless of which of those methods is utilized, the saccharides comprising lactosamine, galactose and glucosamine, must be joined together at some point in the syntheses. Somewhat surprisingly, the Galβ1→4GlcN bond of lactosamine is also one of the more difficult bonds to form in the synthesis of a contemplated compound.

Lactosamine is a compound reported in the literature, but is not readily available. Nevertheless, lactosamine or a derivative of lactosamine provides a good starting material for synthesis of a contemplated compound.

Although lactosamine is not readily available, lactulose, a ketose that possesses no amine group but contains a Galβ1→4Fru bond that is related to lactose and lactosamine, is commercially available. Lactulose, with its Galβ1→4 bond already formed, provides a starting material for one contemplated synthesis of lactosamine. A synthesis of lactosamine (Compound 3) as an acid addition salt is illustrated generally and specifically below in Schemes 1 and 1A, respectively, as are the syntheses of peracetyl N-phthalimidolactosamine (Compound 5) and peracetyl N-phthalimidolactosamine β chloride Compound 6). Numbered compounds in both schemes are the same compounds.

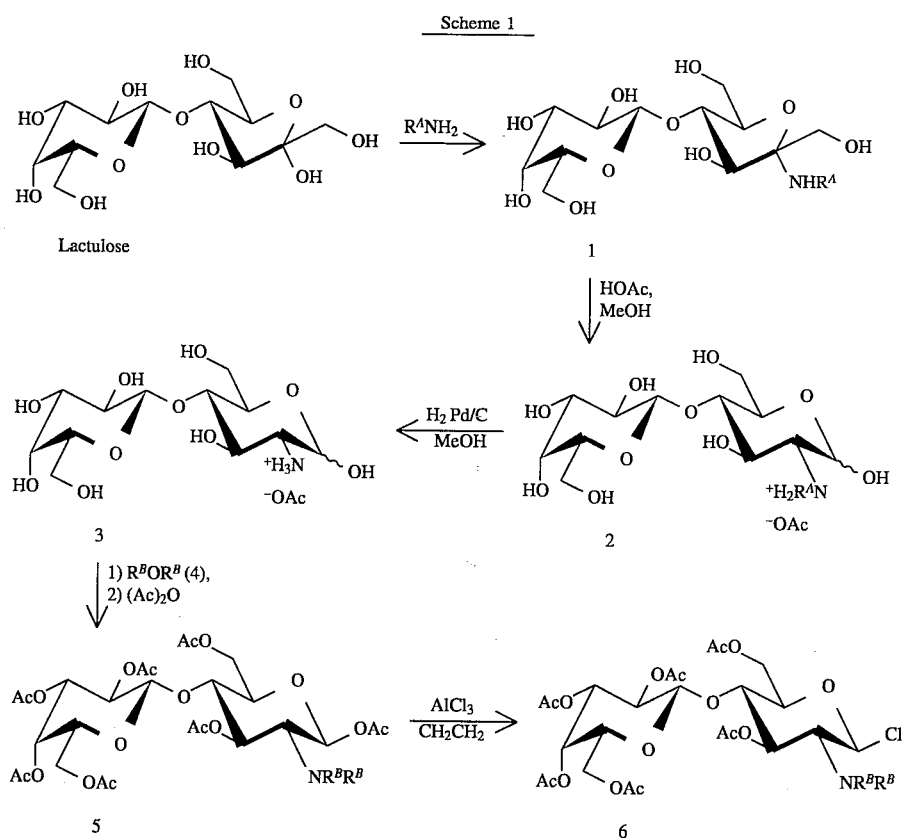

Scheme 1

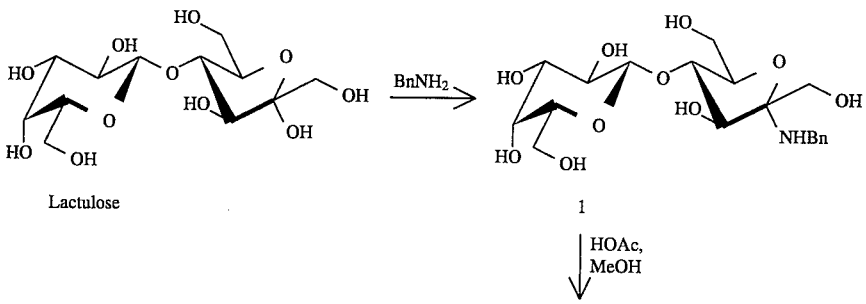

Scheme 1A

-continued
Scheme 1A

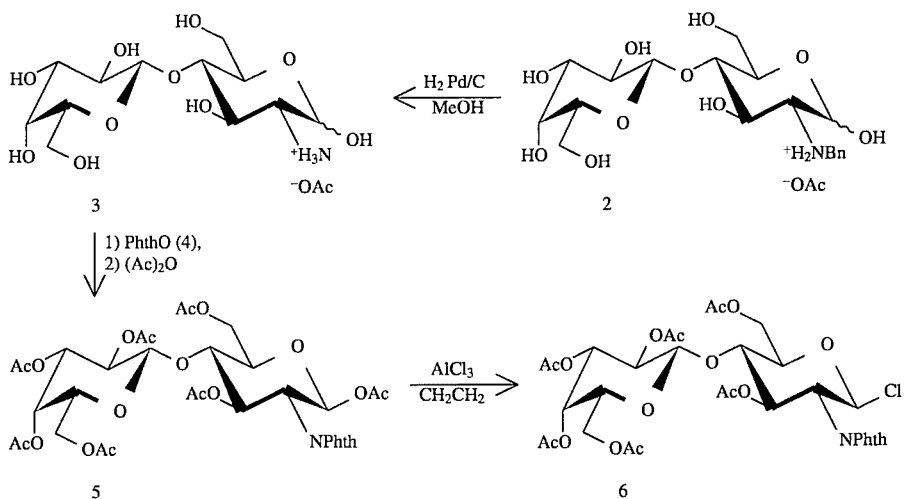

Thus, lactulose was reacted neat with a primary amine that is an ammonia derivative whose nitrogen atom is bonded to a reductively removable blocking group (benzylamine) as both reactant and solvent to form the corresponding N-glycoside, lactulose N-benzyl glycoside, (Bn=benzyl; Compound 1). Reaction of Compound 1 in methanol with about a stoichiometric amount of an organic carboxylic acid having a $pK_a$ value of about 2.5 to about 5.0 (glacial acetic acid) provided N-benzyl lactosammonium acetate (Compound 2) in 50–55 percent yield. Lactosammonium acetate (Compound 3) was prepared by hydrogenolysis of the above methanolic solution using palladium on carbon (Pd/C).

It is noted that other reductively removable blocked amines can be used in place of benzylamine. For example, mono- and dimethoxybenzylamines can be viewed as reductively removable blocked ammonia derivatives in that after reaction with the saccharide, the mono- and dimethoxybenzyl groups can also be removed by hydrogenolysis. Allylamine can similarly be used, with the allyl blocking group being removed by reaction with polymethylhydrosiloxane (PMSH) and palladiumtetrakistriphenylphosphine [Pd-(PPh$_3$)$_4$] in THF as solvent.

Thus, although a benzyl group (Scheme 1A) is used as $R^A$ in Scheme 1, it is to be understood that a monomethoxybenzyl, dimethoxybenzyl or allyl group can be used as $R^A$.

The discussion above and reactions illustrated in Schemes 1 and 1A illustrate a process for preparing lactosamine or a lactosammonium salt from lactulose. In accordance with this process, lactulose is admixed with a primary amine that is a monosubstituted ammonia derivative whose nitrogen atom is bonded to a reductively removable blocking group to form a reaction mixture. The blocked ammonia derivative serves both as the reaction and solvent in this process.

The blocked ammonia derivative (or primary amine) is present in a 2- to about 10-fold molar excess over the moles of lactulose utilized. The primary amine is preferably present in about a 4- to about 8-fold molar excess.

As noted before, primary amines containing other reductively removable blocking groups are contemplated. Thus, allylamine and p-methoxybenzylamine have been successfully used to form the lactulose N-glycoside, and rearranged to the corresponding N-substituted lactosamine.

The reaction mixture so formed is maintained at a temperature of about 10° C. to about 60° C. for a time period sufficient for the corresponding lactulose N-glycoside to form; i.e., for the primary amine to replace the lactulose 2-hydroxyl group. Temperatures from ambient room temperature (about 20° C.) to about 50° C. are preferred.

The maintenance time is a function of several variables such as the molar excess of primary amine, maintenance temperature, and the amount of lactulose N-glycoside desired, and can range from about 8 hours, where little of the product is desired, to as much as two weeks, using low temperatures and amounts of primary amine. For example, when 4–7.5 molar excesses of primary amine (here, benzylamine) were used, the reaction was complete after a maintenance time of seven days at room temperature, but less than 50 percent complete over the same time when a 2-fold excess of benzylamine was used under the same conditions. When the maintenance temperature was raised to 50° C., the reaction using a 4-fold excess of amine was complete after two days (48 hours), whereas a 70° C. reaction temperature caused decomposition.

The presence of a Lewis acid catalyst such as zinc chloride, zinc trifluoromethanesulfonate or magnesium trifluoromethanesulfonate in the reaction medium increased the reaction rate so that reactions using a 7.5-fold excess of benzylamine that were complete after seven days at room temperature without catalyst were completed in two days (48 hours). A similar result was obtained using trifluoroacetic acid as catalyst, which is preferred.

Lactulose is insoluble in alcohol solvents, including methanol. Lactulose can be dissolved in hot DMF and remain in solution after cooling. Both methanol and DMF can be used as cosolvents with the primary amine when an above-discussed catalyst is also present. For example, when methanol was used as a cosolvent, no reaction was had at either room temperature or 50° C. However, when a zinc chloride catalyst was used with a 4-fold excess of benzylamine and methanol as cosolvent, the reaction was complete after 48 hours at room temperature.

The lactulose N-glycoside prepared as discussed above is hygroscopic, and is therefore used quickly after its preparation. That N-glycoside is reacted with about 0.1 equivalents up to an equivalent amount (for best yield) of a carboxylic acid having a $pK_a$ value of about 2.5 to about 5.0 in a $C_1$–$C_4$ alcohol solvent at a temperature of about 10° C. to about 30° C. to rearrange the lactulose N-glycoside into a lactosammonium salt whose amine group is blocked with an above reductively removable blocking group; i.e., an amine-blocked lactosammonium salt having a reductively removable blocking group bonded to the amine nitrogen atom.

The carboxylic acid utilized can be any of a number of such acids as are well known in the art such as acetic ($pK_a$=4.76), propionic ($pK_a$=4.88), butyric ($pK_1$=4.82), chloroacetic ($pK_a$=2.80), methoxyacetic ($pK_1$=3.52), and the like. Glacial acetic acid is preferred. Exemplary $C_1$-$C_3$ alcohols include methanol, which is preferred, ethanol, propanol and iso-propanol. A reaction temperature of ambient room temperature is preferred.

The concentration of lactulose N-glycoside can range from about 0.1M to substantial saturation. Typically utilized concentrations are about 0.5 to about 1.5M in the solvent.

The reductively removable blocking group is then removed. Hydrogenolysis using a palladium catalyst is a preferred process for that removal, particularly where benzylamine or a methoxybenzylamine is used. PMHS and Pd(PPh$_3$)$_4$ are used where allylamine is the primary amine.

The above reduction can take place in any appropriate solvent for the lactosammonium derivative. For example, hydrogenolysis can be carried out in acidic water or $C_1$-$C_3$ alcohol as above. PMHS and Pd(PPh$_3$)$_4$ are typically utilized in THF or a similar solvent.

A thus produced lactosammonium salt is generally recovered after preparation, although, depending upon the solvent used and the use to be put to the compound, recovery is not necessary. Where it is desired to recover the lactosammonium salt, whose anion is the anion form of the acid used in the reduction, can be obtained by well known methods such as chromatography or precipitation. Free lactosamine can be prepared from the salt by ion exchange chromatography or by neutralization, followed by extraction of the free base into an appropriate organic solvent.

The Compound 3-containing methanolic solution resulting from the hydrogenolysis reaction, or another appropriate solution, was then reacted with phthalic anhydride (PhthO) in the presence of a basic catalyst such as Na$_2$CO$_3$ to form the N-phthalamide half-acid, Compound 4. After a suitable amide half-acid, e.g. Compound 4, was formed, any reactive solvent such as methanol was removed. The hydroxyls of the disaccharide were then peracetylated and the phthalimide ring closed to provide peracetylated (Ac) phthalimido Compound 5 in over 10 percent yield from starting material.

An additional synthesis of a lactosammonium salt from lactulose is also contemplated.

Here, lactulose is reacted in a stainless steel autoclave with an equimolar amount of ammonium acetate and liquid ammonia as solvent, the liquid ammonia being added to the autoclave cooled to −78° C. The resulting reaction mixture is warmed to a temperature from zero degrees C. to about 80° C., and maintained for a period of about five hours to about five days, depending upon the temperature used and desired conversion. This reaction forms lactulose aminoglycoside.

After removing the ammonia and ammonium acetate, the latter being typically removed under vacuum, the resulting ammonia-free material is treated with a carboxylic acid as before to form the lactosammonium salt, e.g. Compound 3. The lactosammonium salt is also treated as discussed before to form Compound 5. The β-anomer of Compound 5 was recovered in 3.8 percent overall yield in the first crystallization, where a reaction temperature of 35° C. and reaction time of 24 hours was utilized in the first reaction step.

Although the yield of Compound 5 was less using this procedure than the previously discussed process, this process obviates the need for reductive removal of the amine blocking group used in that process. The palladium-containing catalyst used in that reduction is the most expensive reagent utilized in these syntheses. It is also noted that methanolic ammonia can be used as solvent rather than liquid ammonia, thereby obviating the need for use of an autoclave.

The amine of Compound 5 in Scheme 1 is shown bonded to $R^B$ and $R^B$ groups that together with the depicted nitrogen atom form a $C_4$-$C_8$ cyclic imide such as an exemplary phthalimide (Phth) in Compound 5. It is noted that succinic anhydride, maleic anhydride, mono and dimethylsuccinic anhydrides and citraconic anhydride can also be used to form similar imides, so that $R^B$ and $R^B$ together with the nitrogen atom form a corresponding imide. A cyclic imide formed by the —NR$^B$R$^B$ group provides an amine protecting group that is stable under conditions in which O-acyl groups such as acetate are removed, but can be readily removed with hydrazine. It is also noted that an anhydride need not be used, but can be replaced by a $C_1$-$C_6$ alkyl half ester halide such as methyl phthaloyl chloride.

Compound 5 is shown as the β-anomer. The α-acetate is also formed and the yield of the desired β-acetate can be almost doubled by concentrating the mother liquor from which Compound 5 was obtained to a foam followed by redissolution in DMF and then reaction with hydrazinium acetate, which cleaved the acetate group and caused formation of the β-OH anomer. After isolation of the reaction product by usual extraction techniques and drying, dissolution of the dried material in pyridine, treatment of the pyridine solution with excess acetic anhydride, reaction, and a further extraction, an additional 8.3 percent overall percent yield of Compound 5 was obtained. The final yield of Compound 5 of 18.7 percent was obtained, based on starting materials.

Reaction of Compound 5 with AlCl$_3$ in dichloromethane at room temperature provided a substantially quantitative yield of Compound 6.

Scheme 2, hereinafter, illustrates the transformation of Compound 6, peracetyl N-phthalimidolactosamine β-chloride, into the fully protected sialylated tetrasaccharide, Compound 13. Thus, Compound 6 was reacted at ambient temperature for two hours in step a with Compound 9, whose synthesis is discussed in the examples, in the presence of molecular sieves, collidine and silver trifluoromethanesulfonate (triflate) using dichloromethane as solvent to prepare the corresponding trisaccharide. That fully protected trisaccharide was first treated in step b with 80 percent aqueous acetic acid for two hours at 80° C. to remove the benzylidene protecting group at the 4- and 6-positions of the terminal Gal unit. Hydrazine hydrate was then reacted at reflux for 17 hours with the recovered, partially deprotected trisaccharide in step c to remove the phthalimido and acetyl groups, and form the completely deprotected trisaccharide. Reaction of the deprotected trisaccharide in methanol:water (5:1) with diallylpyrocarbonate in step d provided Compound 10, where AL is allylcarbamoyl.

Where $R^2$ is not a glycoside as described in the syntheses of Scheme 2, and is rather a preferred $C_1$-$C_{18}$ hydrocarbyl group such as benzyl, the glycosylation steps a and b are omitted, providing a tetrasaccharide of Formulas A, I or II, where $R^2$ is other than mono- or disaccharide.

Compound 10 was then sialylated enzymatically in step e in an aqueous buffer using α-(2,3)-sialyltransferase (EC 2.4.99.6) and a number of other enzymes. The reaction was followed by TLC for 10–12 days at ambient temperature, at which time more than 95 percent of Compound 10 had been consumed, and Compound 11 was prepared.

Compound 11 was recovered as a thick syrup that was coevaporated twice with pyridine and then kept under vacuum for 20 hours. The thus dewatered material was redissolved in pyridine to which a catalytic amount of 4-dimethylaminopyridine (DMAP) was added as was acetic anhydride. Two more additions of acetic anhydride over the ensuing 44 hours completed the acetylation reaction and formation of a lactone with the sialyl carboxyl and a saccharide hydroxyl in step f. Methanol was thereafter added to the recovered material to form the sialyl methyl ester and thereafter, another addition of acetic anhydride was made to acetylate the freed hydroxyl to form completely protected Compound 12 in step g.

It should be apparent that Compounds 11 and 12 are compounds of structural Formulas A and III. Using Compound 12 as exemplary, Z is $C_1$–$C_6$ acyl (acetyl), X is $C_1$–$C_6$ acyloxy (acetoxy), $R^2$ is 3Galβ-O-ethyl, $R^3$ is acetyl, $R^4$ is methyl and $R^1$ is allyloxy. It should be equally apparent that the before-mentioned other X groups for a compound of any of the structural formulas are conveniently introduced at the sialylation step. If it is desired that sialyl unit X substituents that are $C_1$–$C_6$ acyloxy or $C_1$–$C_6$ hydroxylacyloxy be present in an inhibitor of structural Formulas I or C, it is preferred that Compound 10 (or a disaccharide without the 3GalβO$R^2$ group) be peracetylated, the allyloxy carbamoyl group (AL) of Compound 10 be removed as in step h, and replaced by one of the phenyl ring-containing $R^1$ acyl groups as in step c of Scheme 3. The molecule is then deprotected and enzymatically sialylated and fucosylated as is discussed hereinafter. For other of the $R^{1-4}$ groups or a similar compound of structural Formulas A, B or III, one can substitute the 3Galβ glycoside $R^2$ of Compound 9, the acylating agent of steps f and g, and the esterifying alcohol of step f.

Treatment of recovered, dried Compound 12 with polymethylhydrosiloxane (PMHS) in anhydrous THF at room temperature followed by palladium tetrakistriphenylphosphine [Pd(PPh$_3$)$_4$] for 18 hours provided Compound 13 in 87 percent yield in step h.

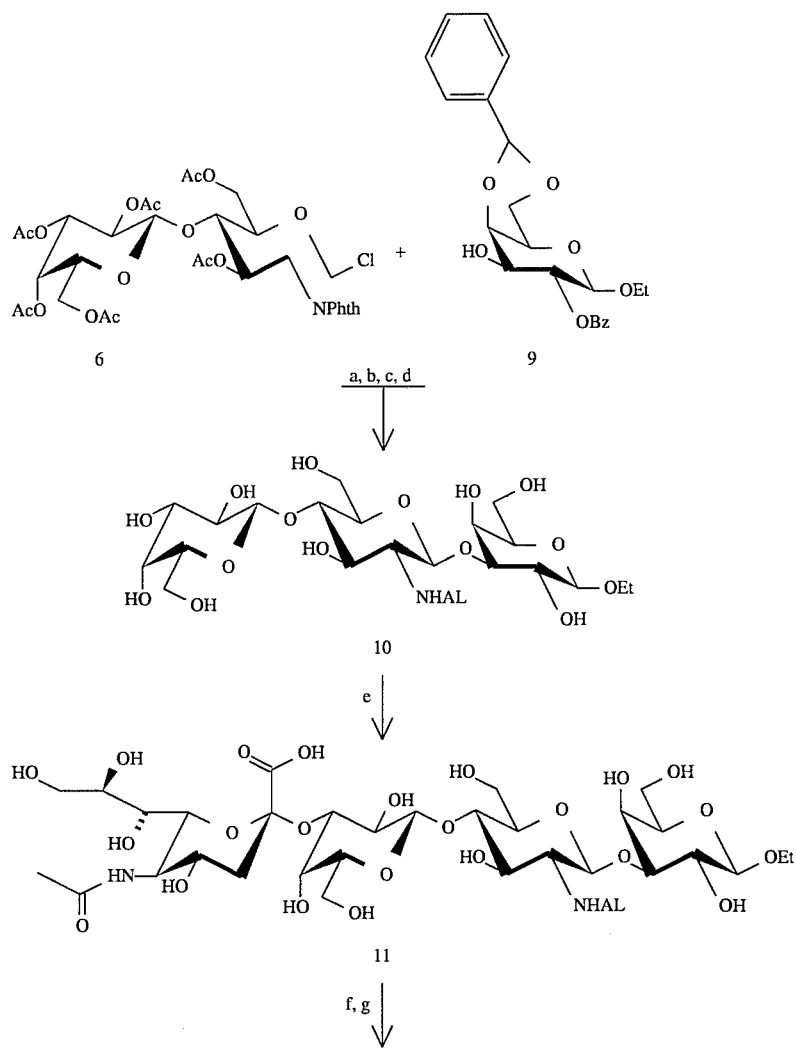

-continued
Scheme 2

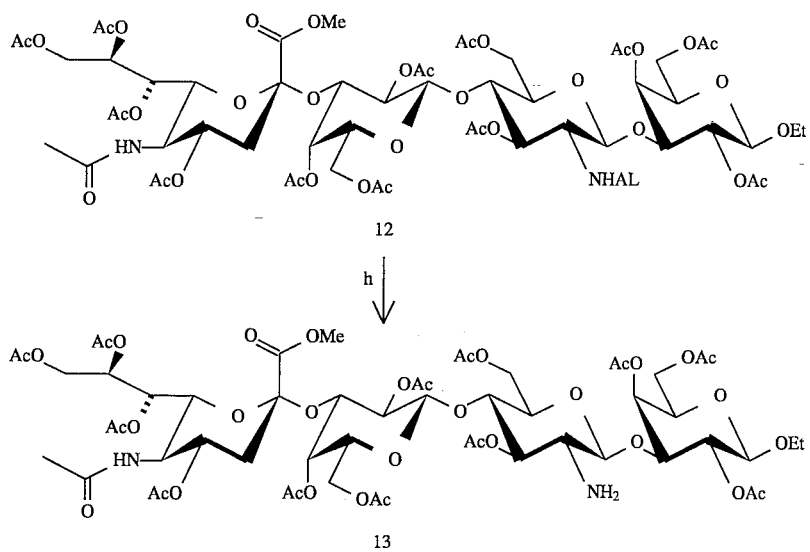

Scheme 3, hereinafter, outlines one remaining synthesis to illustrative inhibitor Compound 17 of Formulas I and C. Thus, reaction of Compound 13 with one equivalent of glacial acetic acid in aqueous methanol for 48 hours at 50° C. provided selective deacylation of the Glc 3-hydroxyl and gave Compound 14 in 65 percent yield in step a.

Compound 14 was then selectively benzoylated in step b in 83 percent yield by reaction with benzoyl chloride in dichloromethane with solid sodium bicarbonate at room temperature for 24 hours to form Compound 15. The alterative $R^1$ groups of a compound of structural Formulas A, I, II and III are added at this step or at an analogous step where $R^2$ is not a saccharide unit.

An organic chemical fucosylation was carried out in step c of Scheme 3 by mixing Compound 15 with tri-O-benzyl fucosyl fluoride, molecular sieves and tetramethylurea in dichloroethane, followed by cooling to −20° C. and addition of stannous chloride and silver perchlorate. After warming slowly to room temperature and stirring for 24 hours, Compound 16 was prepared in 77 percent yield.

Compound 16 is thus a compound of structural Formulas A and B, where Z is a blocked fucosyl group, as well as a compound of Formula II. Use of alternative $R^5$ groups provide the remaining compounds of those structural formulas when combined with the before-discussed X and $R^{1-4}$ groups.

The O-benzyl blocking groups, $R^5$, of the fucosyl saccharide unit were removed in step d by hydrogenation using palladium hydroxide on carbon [Pd(OH)$_2$/C] in methanol as solvent. Reaction for one hour at room temperature provided complete removal of the O-benzyl groups. Filtration and concentration of the debenzylated compound provided an oil that was redissolved in methanol:water (4:1) to which was added sodium methoxide powder in step e. After 16 hours of reaction at room temperature, a 72 percent yield of inhibitor Compound 17 was obtained.

Where $R^5$ is a $C_1$–$C_6$ acyl group, the hydrogenation step is not used and the $R^5$ $C_1$–$C_6$ acyl group is removed along with the $R^3$ and $R^4$ groups. Use of an $R^5$ $C_1$–$C_6$ acyl group and the avoidance of a hydrogenation step, also provides a route for synthesis of nitro group-containing $R^1$ groups.

Scheme 3
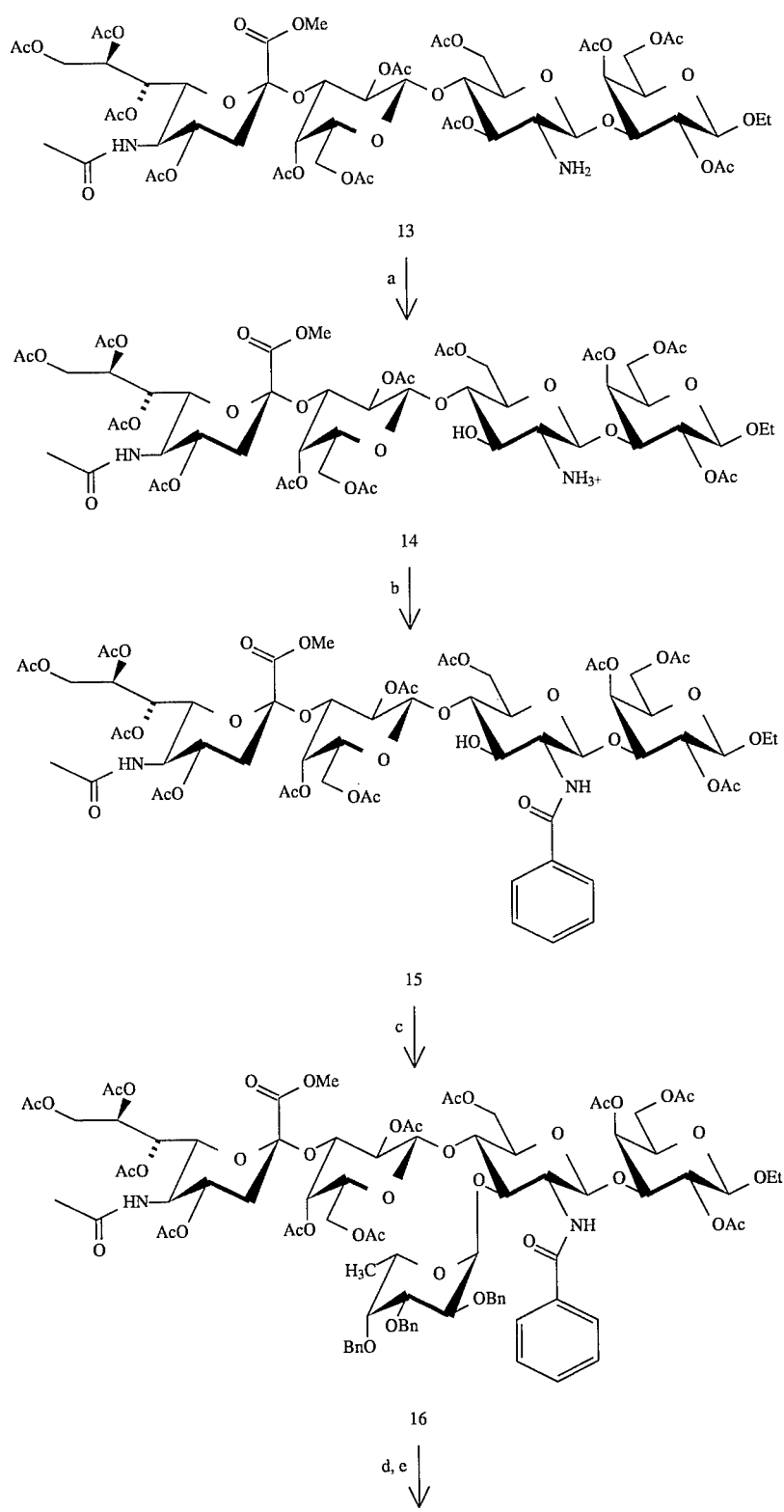

-continued
Scheme 3

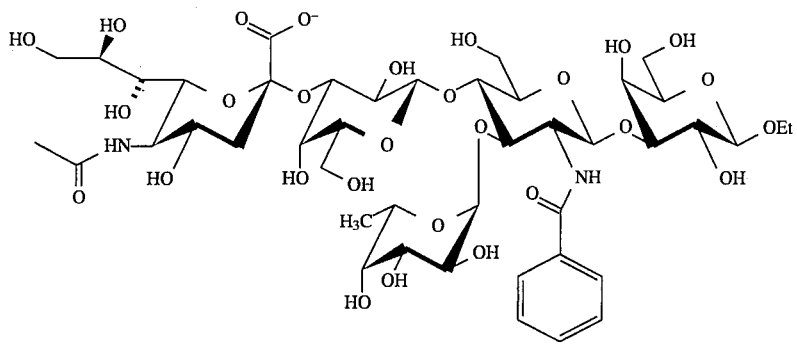

17 where the $R^2$ group is a mono- or disaccharide, an appropriately blocked mono- or disaccharide is used such as Compound 9 of Scheme 2. For example, lactose, a lactose $C_1-C_{18}$ glycoside or melibiose can be made into protected (blocked) benzylidine derivatives similar to that of Compound 9 and then used in the coupling step a of Scheme 2, and the resulting product used in subsequent steps of Schemes 2 and 3.

It is to be understood that lactosamine and its derivatives can be prepared by other methods well known to skilled workers. It is to be further understood that the trisaccharide Compound 10 can be prepared enzymatically by reaction of ethyl 3-O-(2-N-allyloxycarbonyl-2-amino-2-deoxy-β-D-glucopyranosyl)-β-D-galactoside using uridine-5'-diphosphate-galactosyl transferase with UDP-Gal, and other appropriate enzymes following known procedures. Similarly, Compound 11 can be fucosylated enzymatically using a fucosyl transferase (FT), such as fucosyl transferase V, as well as the nucleotide sugar donor GDP-fucose, and other enzymes useful in the regeneration of GDP-fucose, using known procedures. Of course, slight changes in the reaction schemes shown are necessitated by those synthetic changes, but those changes are well within the skill of an ordinary worker.

Still another useful synthetic procedure is shown in Scheme 4, below. Here, the starting material is the free base, Compound 14a, of Compound 14 of Scheme 3.

Scheme 4

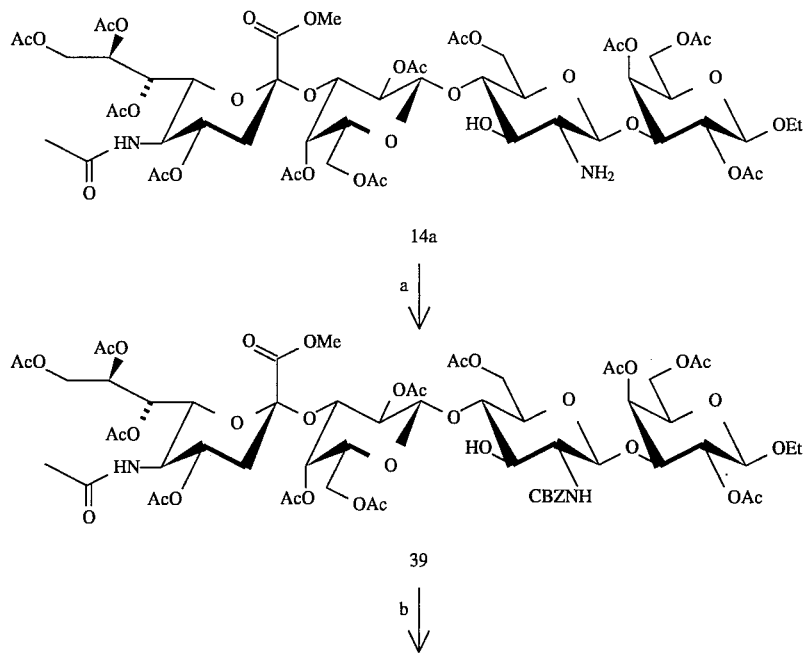

-continued
Scheme 4
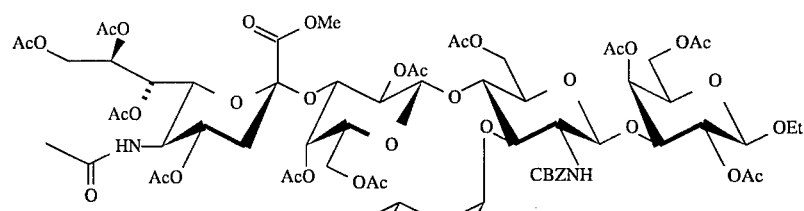
40
c ↓
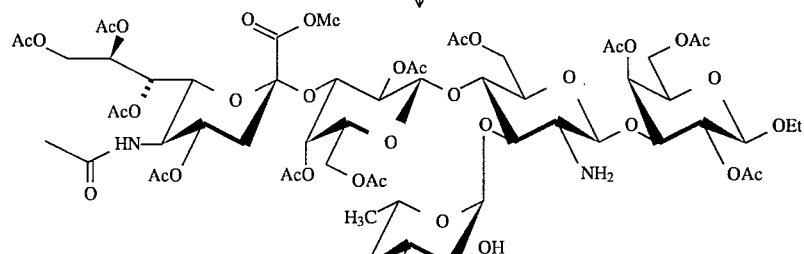
41
d ↓
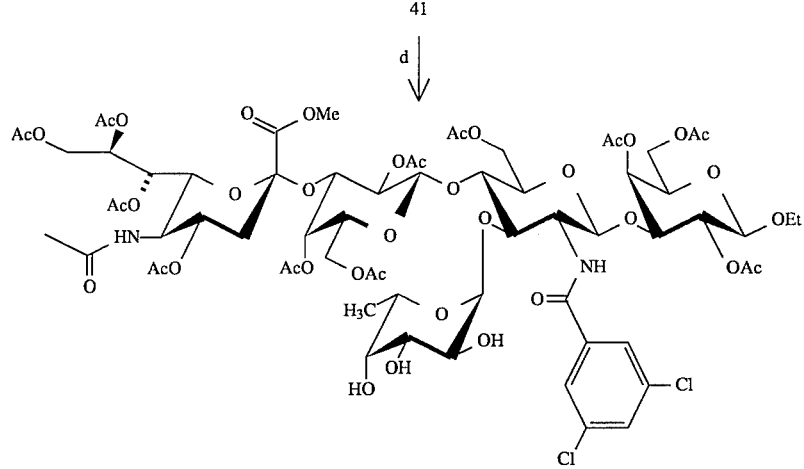
42
e ↓

-continued
Scheme 4

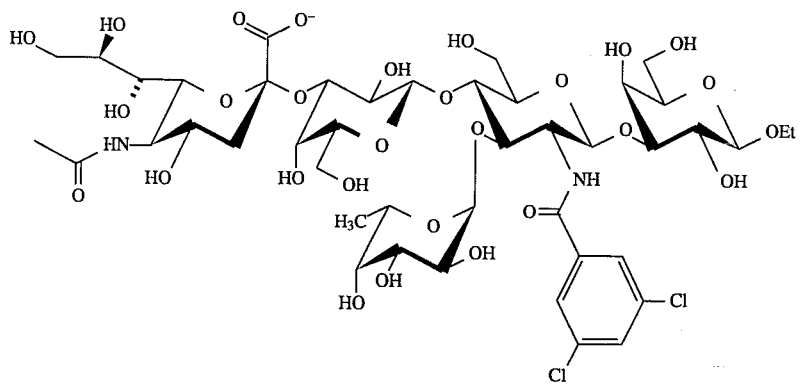

43

Thus, Compound 14a was reacted in step a with a slight excess of carbobenzoxy chloride (CBZ-C$_l$) in dichloromethane, in the presence of sodium bicarbonate followed by another equal amount of CBZ-C$_l$ about eighteen hours later to form the amine-protected Compound 39 in 65 percent yield. Step b of Scheme 4 is substantially the same glycosylation step shown as step c of Scheme 3, with Compound 40 being formed in 73 percent yield, plus recovery of 17 percent starting Compound 39.

The fucosylated free amine, Compound 41, was thereafter formed in 96 percent yield in step c by reaction with ten percent Pd-C in ammonium formate in ethanol at reflux. The free amine of Compound 41 was thereafter reacted in step d with an acyl (YR$^1$) chloride in dichloromethane in the presence of sodium bicarbonate to provide the corresponding hydroxy-blocked N-acylated compound, here, the 3,5-dichlorbenzamide derivative, Compound 42, in high yield. The hydroxyl groups were de-blocked by reaction in 28 percent sodium methoxide-methanol in substantially quantitative yield.

The structures of several particularly preferred inhibitors, Compounds 17, 30–38 and 43–51 have already been shown. Compounds 30–33 were prepared from their respective precursor Compounds 26–29 as described for conversion of Compound 16 into Compound 17 in Scheme 3. Compounds 34–38 and 51 were prepared in manners analogous to those of Scheme 3. Compounds 43–49 were prepared similarly, using the general approach shown in Scheme 4. Compound 50 was prepared following Scheme 3, using the reduction of Scheme 4, step c. These are compounds of structural Formula I, as well as Formula A.

C. Cell Adhesion Inhibition Assay Methods

Numerous direct and indirect methods for in vitro screening of inhibitors of ligand-receptor interactions are available and known to those skilled in the art. For instance, the ability to inhibit adhesion of SLe$^x$-bearing cells to cells expressing a particular selectin can be determined.

As discussed before, several selectin receptor genes have been cloned, and thus, the genes can be inserted and expressed in a wide variety of cells, such as COS cells, CHO cells, adenovirus-transformed human kidney cells as used herein, and the like so that a recombinant selectin receptor such as rELAM (recombinant ELAM-1) can be used in assays, as is described hereinafter. In addition, cells that do not normally express SLe$^x$ are capable of being transformed with one or more glycosyltransferase genes that confer on the transformed cells the ability to synthesize the ligand. [See, e.g., Lowe et al., Cell, 63:475–484 (1990)]. In some assays, the inhibitor compound or agent is incubated with labeled SLe$^x$-bearing cells and activated cells expressing cell surface selectins or recombinant selectin immobilized on a solid surface. Inhibition of cellular adhesion can then be determined by detecting label bound to the surface after appropriate washes.

Typically, the in vitro assays of a contemplated SLe$^x$ analogue compound are competition assays that detect the ability of a contemplated compound to competitively inhibit binding of selectin to cells containing SLe$^x$. Selectin-containing cells are typically activated platelets or activated endothelial cells with a recombinant selectin being as useful, whereas the SLe$^x$-bearing cells are usually neutrophils or HL-60 cells.

Other assay formats involve detection of the presence or absence of various physiological changes in either SLe$^x$ ligand-bearing or selectin-bearing cells that result from the interaction. Examples of suitable assays include the measurement of changes in transcription activity induced by binding (see, e.g., PCT publication No. 3712820), the detection of various cell mediated extra-cellular effects (see, e.g., PCT Publication No. 90/00503), and the detection of changes in the membrane potential of individual cells (see, e.g., U.S. Pat No. 4,343,782), all of which are incorporated herein by reference. Alternatively, conformational changes in isolated receptors or ligands can be detected; see, e.g., U.S. Pat. No. 4,859,609, which is incorporated herein by reference. Still further, one can bind SLe$^x$-expressing cells to solid support-bound selectin, lyse the bound cells and assay for a protein that could only have been present in the bound cells.

Any component of the assay, including the ligand, the selectin receptor, or the SLe$^x$ compound, can be bound to a solid surface. Many methods for immobilizing biomolecules on solid surfaces are known in the art. For instance, the solid surface can be a membrane (e.g., nitrocellulose), a microtiter dish (e.g., PVC or polystyrene) or a bead. The desired component can be covalently bound or non-covalently attached through unspecific bonding.

A wide variety of organic and inorganic polymers, both natural and synthetic can be employed as the material for the solid surface. Illustrative polymers include polyethylene, polypropylene, poly (4-methylbutene), polystyrene, polymethacrylate, poly(ethylene terephthalate), rayon, nylon, poly(vinyl butyrate), silicones, polyformaldehyde, cellulose, cellulose acetate, nitrocellulose, etc. Other materials that can be employed include paper, glasses, ceramics, metals, metalloids, semiconductive materials, cermets or the like. In addition are included substances that form gels, such as proteins, e.g., gelatins, lipopolysaccharides, silicates, agarose and polyacrylamides or polymers which form several aqueous phases, such as dextrans, polyalkylene glycols (alkylene of 2 to 3 carbon atoms) or surfactants, e.g., amphiphilic compounds, such as phospholipids, long chain (12–24 carbon atoms) alkyl ammonium salts and the like. Where the solid surface is porous, various pore sizes may be employed depending upon the nature of the system.

In preparing the surface, a plurality of different materials can be employed, particularly as laminates, to obtain various properties. For example, protein coatings, such as gelatin can be employed to avoid non-specific binding, simplify covalent conjugation, enhance signal detection or the like.

If covalent bonding between a compound and the surface is desired, the surface is usually polyfunctional or capable of being polyfunctionalized. Functional groups that can be present on the surface and used for linking can include carboxylic acids, aldehydes, amino groups, cyano groups, ethyleneic groups, hydroxyl groups, mercapto groups and the like. The manner of linking a wide variety of compounds to various surfaces is well known and is amply illustrated in the literature. See for example Immobilized Enzymes, Inchiro Chibata, Halsted Press, New York (1978), and Cuatrecasas, *J. Biol. Chem.,* 245;3059 1970) which is incorporated herein by reference.

In addition to covalent bonding, various methods for noncovalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as concanavalin A binds a carbohydrate containing compound but not a labelled protein that lacks glycosylation. Various solid surfaces for use in noncovalent attachment of assay components are reviewed in U.S. Pat. Nos. 4,447,576 and 4,254,082, which are incorporated herein by reference.

The label mentioned before can be coupled directly or indirectly to the desired component of the assay according to methods well known in the art, or can be a protein endogenous to the bound cells. A wide variety of labels can be used. The component can be labeled by any one of several methods. The most common method of detection is the use of autoradiography with $^3H$, $^{125}I$, $^{35}S$, $^{14}C$, or $^{32}P$ labeled compounds or the like. The choice of radioactive isotope depends on research preferences due to ease of synthesis, varying stability, and half lives of the selected isotopes. Other non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation.

Non-radioactive labels are often attached by indirect means. Generally, a ligand molecule (e.g., biotin) is covalently bound to the molecule. The ligand then binds to an anti-ligand (e.g., streptavidin) molecule that is either inherently detectable or covalently bound to a signal system, such as a detectable enzyme, a fluorescent compound, or a chemiluminescent compound. Ligands and antiligands can be varied widely. Where a ligand has a natural antiligand, for example, biotin, thyroxine, and cortisol, it can be used in conjunction with the labeled, naturally occurring antiligands. Alternatively, any haptenic or antigenic compound can be used in combination with an antibody.

The before-mentioned label can also be an enzyme or other protein present in a cell whose adhesion is to be inhibited. The amount of that enzyme can thereby be used as a label to determine the amount of binding. Myeloperoxidase is one such protein present in HL-60 cells that is useful as a label in the binding inhibition studies discussed hereinafter.

The $SLe^x$ molecules can also be conjugated directly to signal generating compounds, e.g., by conjugation with an enzyme or fluorophore. Enzymes of interest as labels are primarily hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various signal producing systems which may be used, see, U.S. Pat. No. 4,391,904, which is incorporated herein by reference.

D. Pharmaceutical Compositions

A pharmaceutical composition containing a contemplated $SLe^x$ analogue compound dissolved or dispersed in a pharmaceutically acceptable carrier or diluent is also contemplated. Such a composition contains a cell adhesion-inhibiting amount of a before-discussed, contemplated $SLe^x$ analogue compound.

As will be seen from the following disclosure, a cellular adhesion-inhibiting amount can vary widely. That amount is, however, sufficient to inhibit binding of cells that express sialyl Le X on their cell surfaces to selectin, particularly E-selectin (ELAM-1) preferably by about one-half or more. An exemplary cellular adhesion-inhibiting amount is about 5 to about 60 mg/kg.

A contemplated pharmaceutical composition can be used to block or inhibit cellular adhesion associated with a number of disorders. For instance, a number of inflammatory disorders are associated with selectins expressed on vascular endothelial cells and platelets. The term "inflammation" is used here to refer to reactions of both the specific and non-specific defense systems. A specific defense system reaction is a specific immune system reaction to an antigen. Exemplary of specific defense system reactions include antibody response to antigens, such as viruses, and delayed-type hypersensitivity. A non-specific defense system reaction is an inflammatory response mediated by leukocytes generally incapable of immunological memory. Such cells include macrophages, eosinophils and neutrophils. Examples of non-specific reactions include the immediate swelling after a bee sting, and the collection of peripheral mononuclear (PMN) leukocytes at sites of bacterial infection (e.g., pulmonary infiltrates in bacterial pneumonia and pus formation in abscesses).

Other treatable disorders include, e.g., rheumatoid arthritis, post-ischemic leukocyte-mediated tissue damage (reperfusion injury), frost-bite injury or shock, acute leukocyte-mediated lung injury (e.g., adult respiratory distress syndrome), asthma, traumatic shock, septic shock, nephritis, and acute and chronic inflammation, including atopic dermatitis, psoriasis, and inflammatory bowel disease. Various platelet-mediated pathologies such as atherosclerosis and clotting can also be treated. In addition, tumor metastasis can be inhibited or prevented by inhibiting the adhesion of circulating cancer cells. Examples include carcinoma of the colon and melanoma.

By way of example, reperfusion injury is particularly amenable to treatment by a contemplated pharmaceutical composition. A composition that inhibits a P-selectin-ligand interaction can be particularly useful for treating or preventing reperfusion injury.

A contemplated pharmaceutical composition can be used prophylactically prior to heart surgery to enhance postsurgical recovery.

Because P-selectin is stored in Weibel-Palade bodies of platelets and endothelial cells and is released upon activation by thrombin to mediate adhesion of neutrophils and monocytes, inhibitors of the P-selectin-ligand interaction can be especially useful in minimizing tissue damage that often accompanies thrombotic disorders. For instance, such inhibitors can be of therapeutic value in patients who have recently experienced stroke, myocardial infarctions, deep vein thrombosis, pulmonary embolism, etc. The compounds are especially useful in pre-thrombolytic therapy.

A contemplated composition finds particular use in treating the secondary effects of septic shock or disseminated intravascular coagulation (DIC). Leukocyte emigration into tissues during septic shock or DIC often results in pathological tissue destruction. Furthermore, these patients can have widespread microcirculatory thrombi and diffuse inflammation. A therapeutic composition provided herein inhibits leukocyte emigration at these sites and mitigates tissue damage.

An inhibitor of a selectin-cellular $SLe^x$ ligand interaction is also useful in treating traumatic shock and acute tissue injury associated therewith. Because the selectins play a role in recruitment of leukocytes to the sites of injury, particularly E-selectin (ELAM-1) in cases of acute injury and inflammation, inhibitors thereof can be administered locally or systemically to control tissue damage associated with such injuries. Moreover, because of the specificity of such inhibitors for sites of inflammation, e.g., where ELAM-1 receptors are expressed, these compositions can be more effective and less likely to cause complications when compared to traditional anti-inflammatory agents.

Thus, the present invention also provides a pharmaceutical composition that can be used in treating the aforementioned conditions. A contemplated pharmaceutical composition is comprised of a before-described $SLe^x$ analogue compound that inhibits the interaction between a cellular $SLe^x$ ligand and a selectin receptor, which compound is dissolved or dispersed in a pharmaceutically acceptable diluent. A contemplated pharmaceutical composition is suitable for use in a variety of drug delivery systems. For a brief review of present methods for drug delivery, see, Langer, *Science*, 249:1527–1533 (1990).

In light of the complexity of the inflammatory response in mammals, one of skill will readily recognize that a contemplated pharmaceutical composition can further include other compounds known to interfere with the function of other cellular adhesion molecules. For instance, members of the integrin family of adhesion molecules are thought to play a role in the extravasation of leukocytes at points of infection. For a review of intercellular adhesion receptors, including selectin receptors, and their role immune function, see Springer, *Nature*, 346:425–434 (1990). In addition, successful treatment using a contemplated pharmaceutical composition can also be determined by the state of development of the condition to be treated. Because different adhesion molecules can be up or down regulated in response to a variety of factors during the course of the disease or condition, one of skill will recognize that different pharmaceutical compositions can be required for treatment of different inflammatory states.

In another embodiment, a before-described $SLe^x$ analogue compound of the pharmaceutical composition can be used to target conventional anti-inflammatory drugs or other agents to specific sites of tissue injury. By using such a compound to target a drug to a selectin receptor on, e.g., a vascular endothelial cell, such drugs can achieve higher concentrations at sites of injury. Side effects from the conventional anti-inflammatory chemotherapeutic agents can be substantially alleviated by the lower dosages, the localization of the agent at the injury sites and/or the encapsulation of the agent prior to delivery.

The targeting component, i.e., the $SLe^x$ analogue compound that binds to a selectin, can be directly or indirectly coupled to the chemotherapeutic agent. The coupling, which can be performed by means, generally known in the art, should not substantially inhibit the ability of the ligand to bind the receptor nor should it substantially reduce the activity of the chemotherapeutic agent. A variety of chemotherapeutics can be coupled for targeting. For example, anti-inflammatory agents that can be coupled include immunomodulators, platelet activating factor (PAF) antagonists, cyclooxygenase inhibitors, lipoxygenase inhibitors, and leukotriene antagonists. Some preferred moieties include cyclosporin A, indomethacin, naproxen, FK-506, mycophenolic acid, etc. Similarly, antioxidants, e.g., superoxide dismutase, are useful in treating reperfusion injury when targeted by a contemplated saccharide compound. Likewise, anticancer agents can be targeted by coupling the $SLe^x$ analogue compound to the chemotherapeutic agent. Examples of agents that can be coupled include daunomycin, doxorubicin, vinblastine, bleomycin, etc. Here, again, a $C_1$–$C_6$ alkyl $C_1$–$C_5$ alkylene ω-carboxylate $R^1$ group can be used for coupling.

The selectin receptor targeting can also be accomplished via amphipaths, or dual character molecules (polar:nonpolar) that exist as aggregates in aqueous solution. Amphipaths include nonpolar lipids, polar lipids, mono- and diglycerides, sulfatides, lysolecithin, phospholipids, sapchin, bile acids and salts. These molecules can exist as emulsions and foams, micelles, insoluble monolayers, liquid crystals, phospholipid dispersions and lamellar layers. These are generically referred to herein as liposomes. In these preparations the drug to be delivered is incorporated as part of a liposome in conjunction with a $SLe^x$ analogue compound that binds to the selectin receptor.

A contemplated $SLe^x$ analogue compound whose $R^2$ group is a $C_{12}$–$C_{18}$ hydrocarbyl group is particularly useful in such liposome preparations. Thus, liposomes filled with a desired chemotherapeutic agent can be directed to a site of tissue injury by the selectin-$SLe^x$ analogue compound interaction. When the liposomes are brought into proximity of the affected cells, they deliver the selected therapeutic compositions.

The liposomes of the present invention are formed from standard vesicle-forming lipids, which generally include neutral and negatively charged phospholipids and a sterol, such as cholesterol. The selection of lipids is generally guided by consideration of, e.g., liposome size and stability of the liposomes in the bloodstream.

Typically, the major lipid component in the liposomes is phosphatidylcholine, phosphatidylcholines having a variety of acyl chain groups of varying chain length and degree of saturation are available or may be isolated or synthesized by well-known techniques. In general, less saturated phosphatidylcholines are more easily sized, particularly when the liposomes must be sized below about 0.3 microns, for purposes of filter sterilization. Methods used in sizing and filter-sterilizing liposomes are discussed below. The acyl chain composition of phospholipid can also affect the stability of liposomes in the blood. One preferred phosphatidylcholine is partially hydrogenated egg phosphatidylcholine.

Targeting of liposomes using a variety of targeting agents (e.g., ligands, receptors and monoclonal antibodies) is well known in the art. (See, e.g., U.S. Pat. Nos. 4,957,773 and 4,603,044, both of which are incorporated herein by reference). Glycoproteins and glycolipids of a variety of molecular weights can be used as targeting agents. Typically, glycoproteins having a molecular weight less than about 300,000 daltons, preferably between about 40,000 and about 250,000 are used, more preferably between about 75,000 and about 150,000. Glycolipids of molecular weight of less than about 10,000 daltons, preferably between about 600 and about 4,000 are used.

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid derivatized bleomycin, in addition to using a $SLe^x$ analogue compound for such coupling.

Targeting mechanisms generally require that the targeting agents be positioned on the surface of the liposome in such a manner that the target agents are available for interaction with the selectin receptor. The liposome is typically fashioned in such a way that a connector portion is first incorporated into the membrane at the time of forming the membrane. The connector portion has a lipophilic portion that is firmly embedded and anchored in the membrane. It also has a hydrophilic portion that is chemically available on the aqueous surface of the liposome. The hydrophilic portion is selected so that it is chemically suitable to form a stable chemical bond with the targeting agent which is added later. Therefore, the connector molecule has both a lipophilic anchor and a hydrophilic reactive group suitable for reacting with the target agent and holding the target agent in its correct position, extended out from the liposome's surface. In some cases one can attach the target agent to the connector molecule directly, but in most instances it is more suitable to use a third molecule to act as a chemical bridge, thus linking the connector molecule which is in the membrane with the target agent which is extended, three dimensionally, off the vesicle surface.

Liposome charge is an important determinant in liposome clearance from the blood, with negatively charged liposomes being taken up more rapidly by the reticuloendothelial system [Juliano, *Biochem. Biophys. Res. Commun.*, 63:651 (1975)] and thus having shorter half-lives in the bloodstream. Liposomes with prolonged circulation half-lives are typically desirable for therapeutic and diagnostic uses. Liposomes that can be maintained from 8, 12, or up to 24 hours in the bloodstream provide sustained release of the selectinligand inhibitors of the invention, or can facilitate targeting of the inhibitors (which can be labeled to provide for in vivo diagnostic imaging) to a desired site before being removed by the reticuloendothelial system.

Typically, the liposomes are prepared with about 5–15 mole percent negatively charged phospholipids, such as phosphatidylglycerol, phosphatidylserine or phosphatidylinositol. Added negatively charged phospholipids, such as phosphatidylglycerol, also serves to prevent spontaneous liposome aggregating, and thus minimize the risk of undersized liposomal aggregate formation. Membrane-rigidifying agents, such as sphingomyelin or a saturated neutral phospholipid, at a concentration of at least about 50 mole percent, and 5–15 mole percent of monosialylganglioside, can provide increased circulation of the liposome preparation in the bloodstream, as generally described in U.S. Pat. No. 4,837,028, incorporated herein by reference.

Additionally, the liposome suspension can include lipid-protective agents that protect lipids and drug components against free-radical and lipid-peroxidative damages on storage. Lipophilic free-radical quenchers, such as alphatocopherol and water-soluble iron-specific chelators, such as ferrioxianine, are preferred.

Several methods are available for preparing liposomes, as described in, e.g., Szoka et al., *Ann. Rev. Biophys. Bioeng.*, 9:467 (1980), U.S. Pat. Nos. 4,235,871, 4,501,728 and 4,837,028, incorporated herein by reference. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film can be redissolved in a suitable solvent, such as tertiary butanol, and then lyophilized to form a more homogeneous lipid mixture that is in a more easily hydrated powder-like form. This film is covered with an aqueous solution of the targeted drug and the targeting component and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents such as deoxycholate.

The hydration medium contains the targeted drug at a concentration that is desired in the interior volume of the liposomes in the final liposome suspension. Typically the drug solution contains between 10–100 mg/mL in a buffered saline. The concentration of the targeting $SLe^x$ analogue compound which binds a selectin is generally between about 0.1–20 mg/mL.

Following liposome preparation, the liposomes can be sized to achieve a desired size range and relatively narrow distribution of liposome sizes. One preferred size range is about 0.2–0.4 microns, which allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method that relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes can be extruded through successively smaller-pore membranes, to achieve a gradual reduction in liposome size.

Even under the most efficient encapsulation methods, the initial sized liposome suspension can contain up to 50 percent or more drug and targeting agent in free (non-encapsulated) form. Therefore, to maximize the advantages of liposomal-targeted drug, it is important to remove free drug and targeting agent from the final injectable suspension.

Several methods are available for removing non-entrapped compound from a liposome suspension. In one method, the liposomes in the suspension are pelleted by high-speed centrifugation leaving free compound and very small liposomes in the supernatant. Another method involves concentrating the suspension by ultrafiltration, then resuspending the concentrated liposomes in a drug-free replacement medium. Alternatively, gel filtration can be used to separate large liposome particles from solute molecules.

Following treatment to remove free drug and/or targeting agent, the liposome suspension is brought to a desired concentration for use in intravenous administration. This can involve resuspending the liposomes in a suitable volume of injection medium, where the liposomes have been concentrated, for example by centrifugation or ultrafiltration, or concentrating the suspension, where the drug removal step has increased total suspension volume. The suspension is then sterilized by filtration as described above. The liposome-ligand preparation may be administered parenterally or locally in a dose which varies according to, e.g., the manner of administration, the drug being delivered, the particular disease being treated, etc.

For a pharmaceutical composition that comprises a $SLe^x$ analogue compound that binds to selectin receptors and inhibits binding thereto by $SLe^x$ ligand-containing cells, the dose of the compound varies according to, e.g., the particular compound, the manner of administration, the particular disease being treated and its severity, the overall health and condition of the patient, and the judgment of the prescribing physician. For example, for the treatment of reperfusion injury, the dose of a contemplated $SLe^x$ analogue compound is in the range of about 50 µg to 10,000 mg/day for a 70 kg patient. Ideally, therapeutic administration should begin as soon as possible after the myocardial infarction or other injury. A pharmaceutical composition is intended for parenteral, topical, oral or local administration, such as by aerosol or transdermally, for prophylactic and/or therapeutic treatment. A pharmaceutical composition can be administered in a variety of unit dosage forms depending upon the method of administration. For example, unit dosage forms suitable for oral administration include powder, tablets, pills, capsules and dragees.

Preferably, a pharmaceutical composition is administered intravenously. Thus, this invention provides a composition for intravenous administration that comprises a solution of a contemplated $SLe^x$ analogue compound dissolved or dispersed in a pharmaceutically acceptable diluent (carrier), preferably an aqueous carrier. A variety of aqueous carriers can be used, e.g., water, buffered water, 0.4 percent saline, and the like. These con,positions can be sterilized by conventional, well known sterilization techniques, or can be sterile filtered. The resulting aqueous solutions can be packaged for use as is, or lyophilized, the lyophilized preparation being combined with a sterile aqueous solution prior to administration. A composition can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of $SLe^x$ analogue compound utilized is usually at or at least about 1 percent to as much as 10 to 30 percent by weight and is selected primarily by fluid volumes, viscosities, etc., in accordance with the particular mode of administration selected. As described above, the composition components can be delivered via liposome preparations.

Thus, a typical pharmaceutical composition for intravenous infusion can be made up to contain 250 ml of sterile Ringer's solution, and 25 mg of the $SLe^x$ analogue compound. Actual methods for preparing parenterally administrable compounds are known or apparent to those skilled in the art and are described in more detail in for example, *Remington's Pharmaceutical Sciences*, 17th ed., Mack Publishing Company, Easton, Pa. (1985), which is incorporated herein by reference.

For solid compositions, conventional nontoxic solid diluents (carriers) may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95 percent of active ingredient, that is, a before-described $SLe^x$ analogue compound, preferably about 20 percent (see, *Remington's*, supra).

For aerosol administration, a contemplated $SLe^x$ analogue compound is preferably supplied in finely divided form along with a surfactant and propellant. Typical percentages of a $SLe^x$ analogue compound are about 0.5 to about 30 percent by weight, and preferably about 1 to about 10 percent. The surfactant must of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides can be employed. The surfactant can constitute about 0.1 to about 20 percent by weight of the composition, and preferably about 0.25 to about 5 percent. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the finely divided compounds and surfactant. The ingredients are thus maintained at an elevated pressure until released by action of the valve.

A pharmaceutical composition containing a $SLe^x$ analogue compound can be administered for prophylactic and/or therapeutic treatments. In therapeutic applications, a composition is administered to a patient already suffering from a disease, as described above, in an amount sufficient to inhibit binding between cells expressing a selectin and neutrophils or HL-60 cells; i.e., cure or at least partially arrest the symptoms of the disease and its complications. An amount adequate to accomplish this is defined as "therapeutically effective dose" or "a cell adhesion-inhibiting amount". Amounts effective for this use depend on the severity of the disease and the weight and general state of the patient, but generally range from about 0.5 mg to about 10,000 mg of SLe$^x$ analogue compound per day for a 70 kg patient, with dosages of from about 5 mg to about 2,000 mg of a compound per day being more commonly used.

In prophylactic applications, a composition containing a contemplated compound is administered to a patient susceptible to or otherwise at risk of a particular disease. Such an amount is defined to be a "prophylactically effective dose" and is also an amount sufficient to inhibit adhesion (binding) of SLe$^x$-containing cells to selectin. In this use, the precise amounts again depend on the patient's state of health and weight, but generally range from about 0.5 mg to about 5,000 mg per 70 kilogram patient, more commonly from about 5 mg to about 2,000 mg per 70 kg of body weight.

Another way to assess an adhesion-inhibiting amount of a contemplated SLe$^x$ analogue compound is to compare binding inhibition exhibited by the SLe$^x$ analogue compound to that provided by SLe$^x$ itself. One convenient way to make that comparison is by use of IC$_{50}$ (the concentration needed to inhibit binding by one-half) of the two compared materials, and base the amount used on the amount of SLe$^x$ and an amount of the SLe$^x$ analogue compound that is a multiple of the IC$_{50}$ value for that compound.

Typically, a compound whose IC$_{50}$ value is about one-tenth that of SLe$^x$ itself, when used at ten times the molar amount of SLe$^x$ is a useful cell adhesion-inhibiting amount. More preferably, the amount is about four times the amount of SLe$^x$. More preferably still, the amount is equal to that of SLe$^x$. Most preferably, as is the case with most of the SLe$^x$ analogue compounds described herein, the amount used is less than the amount of SLe$^x$ used such as about one-half to about one-tenth the molar amount of SLe$^x$ itself.

Single or multiple administrations of a composition can be carried out with dose levels and pattern being selected by the treating physician. In any event, the pharmaceutical formulations should provide a quantity of a SLe$^x$ analogue compound sufficient to effectively treat the patient.

The compounds can also find use as diagnostic reagents. For example, labeled compounds can be used to locate areas of inflammation or tumor metastasis in a patient suspected of having an inflammation. For this use, the compounds can be labeled with $^{125}$I, $^{14}$C, or tritium.

EXAMPLE 1

Lactulose N-Benzyl Glycoside (Compound 1)

A 500 mL 3-neck round bottom flask was immersed in an ice bath and charged with lactulose (23.9 gm, 69.8 mmol) and benzylamine (109 mL, 526 mmol, 7.5 equivalent). The flask was then capped and stirred using a magnetic stirbar. The ice bath was permitted to melt and the reaction was permitted to slowly warm to room temperature. Dissolution of the solid material occurred over several hours and the reaction became yellow in color. TLC in 60:50:15 CHCl$_3$:MeOH:15 mM CaCl$_2$ can be used to monitor the progress of the reaction (lactulose R$_f$=0.45, product R$_f$=0.75, orcinol visualization).

The reaction was quite slow and appeared to reach completion in 5–7 days. At the time the reaction was judged to be complete, the stirbar was removed from the reaction, the flask was fitted with an overhead mechanical stirrer, and the apparatus was immersed in an ice bath. Hexane (250 mL) was then added to the flask and the mixture was stirred vigorously for approximately 0 seconds. Stirring was then discontinued and the mixture was permitted to separate into two distinct layers (this separation takes from 15 minutes to one hour). At this time, the upper hexane/benzylamine layer was removed through a tube by suction. Extraction of benzylamine was repeated twice more using hexane (250 mL portions) and then was done three more times using 250 mL portions of diethyl ether (all extractions were done on ice).

After these extractions were performed a viscous pale yellow residue was left. This material was dissolved in ethanol (300 mL) and was transferred to a 2 liter single neck round bottom flask. The yellow solution was concentrated by rotary evaporation to a thick syrup. Reagent grade acetone (1000 mL) was then rapidly stirred with a magnetic stirbar at zero degrees C, and the solution was then slowly treated with the ethanolic syrup. As the syrup was slowly added, a milky white precipitate began to form. After addition was complete, the flask was capped and stored in a −20° C. freezer overnight (about 18 hours). After removal from the freezer, a white solid cake was apparent at the bottom of the flask and the supernatant was clear yellow. The solution was then decanted off and the crude solid Compound 1 was pulled under high vacuum to remove residual acetone. The product (Compound 1) is a very unstable solid and was used immediately in the next reaction.

EXAMPLE 2

N-benzyl Lactosamine Acetate Salt (Compound 2)

The crude product (Compound 1) from above (30.1 gm, 69.8 mmol, theoretical) was dissolved in 1000 mL of reagent grade methanol and was stirred at room temperature. Glacial acetic acid (4 mL, 70 mmol) was then added and the flask was capped. The pale yellow reaction mixture was permitted to stir at room temperature and was monitored by TLC in the same solvent system as described above. The product Compound 2 appeared at R$_f$=0.65 (residual lactulose is noticeable by TLC from the beginning of this reaction but its amount does not seem to increase substantially as the reaction progresses). When Compound 1 appeared to have been completely consumed by TLC (24–48 hours), 100 µL was withdrawn from the reaction mixture and was evaporated under a stream of argon. The yellow residue was then dissolved in CD$_3$OD and evaporated again to a yellow residue. This material was then dissolved in D$_2$O and was analyzed by $^1$H-NMR.

This crude solution of Compound 2 was then used in the next reaction. For yield calculation purposes, a small aliquot of known volume can be removed from the reaction mixture, concentrated to dryness, dissolved in H$_2$O, brought to pH >10, and chromatographed using reverse phase silica gel flash chromatography first eluting with H$_2$O and then with 2:1 H$_2$O:MeOH. Typical yields from lactulose were 50–55 percent. $^1$H-NMR (300 MHz, δ in ppm relative to HOD) 7.44 (m, 5H), 5.49 (d, J=3 Hz, 1H), 5.05 (d, J=8 Hz, 1H), 4.39 (d, J=7 Hz, 1H), 4.38 (d, J=8 Hz, 2H), 4.35 (d, J=7 Hz, 1H), 4.10–3.5 (m, 11H), 3.24 (dd, J=3 Hz, J=10 Hz, 1H), 3.00 (dd, J=8 Hz, J=10 Hz, 1H), 2.87 (s, 3H).

EXAMPLE 3

Lactosamine Acetate Salt (Compound 3)

The 2 liter flask containing the crude acidic methanolic solution of Compound 2 from the previous reaction was equipped with a three-way stopcock and was put through an argon/vacuum/purge cycle three times using a balloon of argon and a house vacuum line. The flask was opened and 10 percent palladium on carbon was added (7.4 gm, 6.98 mmol). The flask was then re-equipped with a three-way stopcock and put through a vacuum/purge cycle three times using hydrogen gas. The reaction was then held under a hydrogen atmosphere using a balloon.

The reaction was monitored closely by TLC (product $R_f$=0.2). When starting material was consumed, a 100 μL aliquot was withdrawn, placed in an eppendorf tube, spun in a microfuge, and the clear supernatant was removed and was used to prepare an NMR sample as in the previous reaction. Once the NMR showed complete loss of Compound 2, the slurry was filtered through a plug of celite on a medium porosity sintered glass funnel using methanol. The clear yellow solution was then concentrated by rotary evaporation to 140 mL in a 500 mL round bottom flask and used crude in the following reaction. Compound 3: $^1$H-NMR (300 MHz, δ in ppm relative to HOD) 5.40 (d, J=3 Hz, 1H), 4.90 (d, J=8 Hz, 1H), 4.41 (d, J=8 Hz, 1H), 4.00-3.5 (m, 11H), 3.28 (dd, J=3 Hz, J=8 Hz, 1H), 2.98 (dd, J=7 Hz, J=8 Hz, 1H).

EXAMPLE 4

2-Deoxy-2-(2'-carboxy)-benzamido-4-O-β-D-galactopyranosyl)-β-D-glucopyranoside (Compound 4) and
1,3,6-Tri-O-acetyl-2-deoxy-2-phthalimido-4-O-(2,3,4,6-tetra-O-acetyl-β-D-galactopyranosyl)-β-D-glucopyranoside (Compound 5)

The crude acidic methanolic solution of Compound 3 was diluted with 14 mL of $H_2O$ and treated with sodium carbonate (29.7 gm, 280 mmol) followed by phthalic anhydride (20.7 gm, 140 mmol). The reaction was watched carefully because some foaming occurs initially. After four hours, the reaction was complete, and the slurry was filtered through a sintered glass funnel to remove residual sodium carbonate and phthalate-based material. The filtrate was then concentrated to a paste first by rotary evaporation and then under high vacuum to provide Compound 4. Removing as much of the trace methanol and $H_2O$ left in the material is essential to avoid side reaction with acetic anhydride in the following acetylation.

When the material was judged to be dry enough, pyridine (212 mL) was added followed by acetic anhydride (106 mL, 1.12 mol). The mixture was shaken manually at first to promote dissolution, but once an initial exotherm began to occur, dissolution proceeded and magnetic stirring was then used. After stirring overnight (about 18 hours), TLC in 20:1 $CHCl_3$:MeOH indicated preponderance of one major UV active spot which cospotted with authentic Compound 5. The solution was cooled to zero degrees C, treated with 32 mL of $H_2O$, and stirred for 15 minutes to hydrolyze excess acetic anhydride. The solution was then diluted to 1000 mL with dichloromethane and washed (3×1000 mL) with 2N HCl, (3×1000 mL) with saturated $NaHCO_3$, and (1×1000 mL) with saturated NaCl. The organic solution was then dried (MgSO$_4$), filtered, and concentrated to a crude product. $^1$H-NMR was then run in CDCl$_3$ and indicated an approximately 1:1 mixture of α- and β-anomers. This crude product was dissolved in a minimum amount of methanol (about 30 mL) and crystallization ensued within a matter of minutes. After remaining at room temperature for several hours, the solid was collected by filtration and rinsed with ice cold methanol. After air drying the product, pure Compound 5 was collected (5.6 gm, 10.4 percent) as a white powder. $^1$H-NMR (300 MHz, δ in ppm relative to CHCl$_3$) 7.90–7.70 (m, 4H), 6.50 (d, J=8 Hz, 1H), 5.83 (dd, J=10.5 Hz, J=8 Hz, 1H), 5.36 (d, J=3.5 Hz, 1H), 5.15 (dd, J=8 Hz, J=10.5 Hz, 1H), 4.97 (dd, J=10 Hz, J=3.5 Hz, 1H), 4.56–3.83 (m, 9H), 2.20–1.90 (7s, 21H).

EXAMPLE 5

Conversion of
1,3,6-tri-O-acetyl-2-deoxy-2-phthalimido-4-O-(2,3,4,6-tetra-O-acetyl-β-D-galactopyranosyl)-β-D-glucopyranoside to Compound 5

The a-acetate-containing mother liquor from the crystallization of Compound 5 discussed above was concentrated to a foam and dissolved in DMF (110 mL). This solution was stirred under argon at 55° C. Hydrazinium acetate (9.5 gm, 104 mmol) was then added. After 15 minutes, TLC in 20:1 $CHCl_3$:MeOH indicated complete loss of starting material and appearance of a slightly lower $R_f$ spot. The reaction was cooled to room temperature and diluted to 1000 mL with ethyl acetate. The solution was then washed (2×1000 mL) with $H_2O$ and (2×1000 mL) with saturated NaCl. The organics were dried (MgSO$_4$), filtered and concentrated.

The crude concentrated product was dissolved in pyridine 50 mL and treated with acetic anhydride (25 mL). After stirring overnight (about 18 hours), TLC in 20:1 $CHCl_3$:MeOH indicated preponderance of one major UV active spot that cospotted with authentic Compound 5. The solution was cooled to zero degrees C., treated with 7.5 mL of $H_2O$, and stirred for 15 minutes to hydrolyze excess acetic anhydride. The solution was diluted to 250 mL with dichloromethane and washed (3×250 mL) with 2N HCl, (3×250 mL) with saturated $NaHCO_3$, and (1×250 mL) with saturated NaCl. The organic solution was dried (MgSO$_4$), filtered, and concentrated to a crude product. The crude product was then dissolved in a minimum of methanol and once again crystallization occurred. After several hours, the solid Compound 5 was isolated as before to provide another crop of product (4.4 gm, 8.3 percent) as a white powder. Overall yield of Compound 5 for two crops, 18.7 percent, 10 gm.

EXAMPLE 5A

Alternative Preparation of Compound 5 from Lactulose

A. Lactulose aminoglycoside (Compound 1A)

A 300 mL stainless steel autoclave containing a stirbar, lactulose (17.1 g, 50 mmol), and ammonium acetate (3.85 g, 50 mmol) was cooled to −78 ° C. and charged with 80 mL of liquid ammonia. The autoclave was sealed and allowed to warm to room temperature with stirring. Once the autoclave had reached room temperature, it was placed in an oil bath and heated to 35° C. for 24 hours. The autoclave was then cooled to room temperature and carefully vented to the atmosphere. Once all of the ammonia had dissipated, approximately two hours, the entire autoclave was placed in a vacuum desiccator containing phosphorous pentoxide and carefully put under high vacuum. After being held under high vacuum overnight, the contents of the autoclave had become a pale yellow foam. The compound was quite hygroscopic and was quickly removed from the autoclave and placed in a sealed jar. This material was used crude in the following reaction.

B. Lactosamine acetate (Compound 2A)

Lactulose aminoglycoside (Compound 10) (3.41 gm, 10 mmol) was dissolved in 100 mL of anhydrous methanol and stirred at room temperature under argon. Glacial acetic acid (572 μL, 10 mmol) was then added. After 24 hours, the yellow solution was concentrated to a foam that appeared to contain lactosamine acetate salt as a 1:1 mixture of α and β anomers. Two other products were apparent which are thought to be the a and b anomers of galactopyranosyl mannosamine. This product was used crude in the following reaction.

Compound 5 was then prepared from Compound 2A by using the crude material obtained in step B., above, with the procedures of Example 4 at about 1/7–1/10 scale. Acetone constituted about one-third of the solvent utilized to form the phthalamide half-acid. The ultimately produced peracetyl phthalimide (Compound 5) was prepared in 3.8 percent yield based on lactulose, with no second crop of crystals being sought.

EXAMPLE 6

1-Chloro-3,6-di-O-acetyl-2-deoxy-2-phthalimido-4-O-(2,3, 4,6-tetra-O-acetyl-β-D-galactopyranosyl)-β-D-glycopyranoside (Compound 6)

The anomeric acetate (Compound 5) (3.3 gm, 4.3 mmol) was stirred in 43 mL of dry $CH_2Cl_2$ under argon at room temperature. Aluminum trichloride (2.9 gm, 21.5 mmol) was then added as a solid. After 40 minutes, the mixture was rinsed into a separatory funnel to a volume of 400 mL in 1:1 $CH_2Cl_2:H_2O$. The mixture was shaken, the aqueous phase removed, and the organic solution was washed 2×200 mL with $H_2O$ and 3×200 mL with saturated $NaHCO_3$ solution. The clear pale yellow solution was then dried ($MgSO_4$), filtered and concentrated to a pale yellow powder (3.2 gm, 10096). This material was then used for the condensation in Example 7.

EXAMPLE 7

Ethyl β-D galactopyranoside (Compound 7)

A solution of 2,3,4,6,-tetra-O-acetylgalactosyl bromide (2.5 kg) in dichloromethane (4 L) was added at a rate of 20–25 mL/minute to a reactor charged with silver carbonate (3.13 kg, 11.4 mol), 4 Å molecular sieves (2.37 kg), dichloromethane (16 L), and anhydrous ethanol (4.0 L). Agitation was maintained to provide vigorous mixing of the reagents. Two hours after complete addition of the bromide solution was achieved, TLC on silica gel developed with hexane:ethyl acetate 1:1 showed no bromide present. At that time the reaction mixture was filtered through a celite pad (1 kg), and the filtrate was evaporated at 30°–35° C. under vacuum to give a brown oil (1.95 kg). This oil was dried under vacuum for 17 hours. $^1$H-NMR (CDCL$_3$) δ: 5.36(1H, d, $J_{3,4}$=3.7 Hz, H-4), 5.17(1H, dd, $J_{2,3}$=11.0 Hz, H-2), 4.99(1H, dd, H-3), 4.46(1H, d, $J_{1,2}$=8.3 Hz, H-1), 2.15, 2.05, 2.04, 1.95(12H, 4s, OAc), 1.21(3H, t, OCH$_2$CH$_3$).

The crude ethyl tetraacetyl galactopyranoside (1.95 kg) was dissolved in anhydrous methanol (11.7 L) and a 25 percent sodium methoxide in methanol solution (90 mL) was added dropwise. The solution was stirred for one hour at which time TLC on silica gel developed with ethyl acetate:methanol 2:1 showed no starting material to be present. The product had an $R_f$=0.6. The solution was neutralized by the addition of Amberlite IR-120(H$^+$) resin (0.6 kg) and stirring. When the solution pH=6–7, the resin was removed by filtration and the filtrate was evaporated under vacuum to afford a pale yellow solid. This solid was dissolved in boiling ethanol (11 L). The resulting solution was permitted to cool to 25° C. and then cooled to zero degrees C. to give a white precipitate. Filtration of this solid gave ethyl β-D-galactopyranoside, Compound 7, (0.851 kg). $^1$H-NMR (D$_2$O) δ: 4.38(1H, d, $J_{1,2}$=8.0 Hz, H-1), 3.89(1H, bd, $J_{3,4}$=3.7HZ, H-4), 1.2(3H, t, OCH$_2$CH$_3$).

EXAMPLE 8

Ethyl 4,6-O-benzylidene-β-D-galactopyranoside (Compound 8)

Ethyl β-D-galactopyranoside, Compound 7, (0.851 kg, 4.09 mol) was charged into a 20 L rotovap flask with toluene sulfonic acid (1.5 g, 7.9 mmol). The evaporator flask was fixed to the evaporator and benzaldehyde dimethyl acetal (1.23 L, 8.18 mol) was added by aspiration. The mixture was tumbled for four hours. Between thirty and forty minutes after addition of the acetal, near complete solution was obtained followed rapidly by the appearance of a heavy precipitate. Rotation was continued for four hours at which time triethylamine (1.5 mL) was added to neutralize the reaction mixture. A vacuum was applied and the solvent was removed to give a solid mass. Hexane (6 L) was charged into the flask and the mixture tumbled for 0.5 hours. The resulting solid was filtered and washed on the filter with hexane:ethyl ether 1:1 (2 L). The white solid so obtained was dried under vacuum for 17 hours to give pure ethyl 4,6-O-benzylidene-β-D-galactopyranoside Compound 8, (1.0 kg,3.38 mol) in 83 percent yield. $^1$H-NMR (CDCl$_3$) δ: 7.53(2H, m, aromatics), 7.37(3H, m, aromatics), 5.57(1H, s, CHPh), 4.29(1H, d, $J_{1,2}$=7.0 Hz, H-1), 4.21(1H, d, $J_{3,4}$=3.27 Hz, H-4), 1.29 (3H, t, OCH$_2$CH$_3$).

EXAMPLE 9

Ethyl 2-O-benzoyl-4,6-O-benzylidene-β-D-galactopyranoside (Compound 9)

Ethyl 4,6-O-benzylidene-β-D-galactopyranoside, Compound 8, (0.924 kg, 3.12 mol) was put into a 20 liter reactor equipped with an air drive, a pressure equalizing addition funnel with gas inlet, cooling bath, and a gas outlet. Before sealing the flask, dichloromethane (9.3 L) and pyridine (2 L) were added, which gave a homogeneous solution. The addition funnel was charged with chloroacetyl chloride (0.388 kg, 3.43 mol, 273 mL) as a 60 percent solution in dichloromethane. The flask was sealed and a low flow of dry nitrogen was begun. The bath was cooled to −65°±5° C. and the reaction mixture was stirred for 30 minutes. At that time dropwise addition of the acyl chloride solution was begun at a rate of 3–4 mL per minute. After complete addition of this solution, the reaction mixture was maintained at −65°±5° C. for an additional one hour. At that time benzoyl chloride (0.614 kg, 4.37 mol, 0.507 L) was added to the reaction mixture at a rate of 8–12 mL per minute. The reaction mixture was permitted to warm to room temperature and left for 17 hours. The reaction mixture was filtered to remove precipitated salts, and the filtrate was concentrated in vacuo to remove most of the dichloromethane. A small sample was set aside for $^1$H-NMR. $^1$H-NMR (CDCl$_3$) δ: 5.75(1H, dd, $J_{2,3}$=10.6 Hz, H-2), 5.56(1H, s, CHPh), 5.25(1H, dd, $J_{3,4}$=3.44 Hz, H-3), 4.69(1H, d, $J_{1,2}$=8.48 Hz, H-1), 4.48(1H, bd, H-4), 1.15(3H, t, OCH$_2$H$_3$).

Water (180 mL) was added to the concentrate and the resulting mixture was agitated for two hours at 40° C. At that time, the reaction mixture was further concentrated to give a yellow residue that was dissolved in dichloromethane (11 L) and transferred to a 50 liter extractor. The organic solution was successively extracted with ice cold aqueous 0.5N HCl (11 L), aqueous saturated sodium hydrogen carbonate (11 L), and cold water (11 L). The organic layer was dried over anhydrous sodium sulfate (1.0 kg), filtered, and the filtrate was evaporated to give a yellow solid that was dried under high vacuum. This reaction was monitored by TLC on silica gel developed with hexane:ethyl acetate 1:1.

This solid was dissolved in hot ethanol (9.5 L) that, after cooling and filtration, gave ethyl 2-O-benzoyl-4,6-O-benzylidene-β-D-galactopyranoside, Compound 9, (0.737 kg, 1.85 mol) in 59 percent yield. $^1$H-NMR (CDCl$_3$) δ: 5.59(1H, s, CHPh), 5.36(1H, dd, J$_{2,3}$=10.07 Hz, H-2), 4.64 (1H, d, J$_{1,2}$=8.21 Hz, H-1), 1.15 (3H, t, OCH$_2$CH$_3$).

To confirm that the benzoate was at the C-2 and that C-3 carried a free hydroxyl group, a drop of trichloroacetyl isocyanate was added to the nmr sample and the spectrum was reacquired. This spectrum contained a low field doublet of doublets at δ=5.27 typical of H-3 of galactose which is esterified at C-3. The original filtrate obtained from the reaction mixture contained additional quantities of product.

EXAMPLE 10

Ethyl (β-D-Galactopyranosyl)-(1-4)-O-(2-N-allyloxycarbonyl-2-deoxy-β-D-glucopyranosyl)-(1-3)-O-β-D-galactopyranoside Compound 10)

To a mixture of ethyl 2-O-benzoyl-4,6-O-benzylidene-β-D-galactopyranoside, Compound 9, (0.76 g, 1.9 mmol), 4 Å molecular sieves (2 g), dichloromethane (10 mL), collidine (0.278 mL, 2.1 mmol), and silver trifluoromethanesulfonate (0.522 g, 2 mmol) cooled to −25° C. was added dropwise a solution of 4-O-(2,3,4,6-tetra-O-acetyl-β-D-galactopyranosyl)-3,4,6-tri-O-acetyl-2-deoxy-2-phthalimido-β-D-glucopyranosyl chloride (Compound 6; 1.484 g, 2 mmol) dissolved in dichloromethane (5 mL). The resulting mixture was stirred and warmed to ambient temperature after complete addition of the chloride. After two hours, the mixture was diluted with dichloromethane and filtered. The filtrate was washed successively with aqueous sodium bisulfite, aqueous hydrochloric acid, aqueous sodium hydrogen carbonate, and finally water. The organic layer was dried over anhydrous sodium sulfate, filtered and evaporated to give a solid mass that was recrystallized from dichloromethane-:hexane.

The resulting fully blocked trisaccharide (0.66 g) was treated with 80 percent aqueous acetic acid (5 mL) at 80° C. for two hours at which time the solvent was removed by evaporation. The residue was coevaporated with toluene-ethyl acetate two times to give a residue that was dissolved in ethanol (10 mL). Hydrazine hydrate (0.3 mL) was added and the resulting mixture was refluxed for 17 hours to give a precipitate that was filtered to give a solid (0.45 g) after drying. This solid was dissolved in methanol:water 5:1 and treated with diallylpyrocarbonate (0.166 mL) for one hour. The resulting mixture was evaporated and partitioned between dichloromethane and water. The aqueous layer was separated and concentrated to provide Compound 10 as a residue that solidified upon trituration with ethyl acetate:acetone 2:1.

This provided the title trisaccharide (Compound 10) which was enzymatically sialylated to give ethyl [sodium (5-acetamido-3,5-dideoxy-α-D-glycero-D-galacto-nonulopyranosylonate)]-(2-3)-O-(β-D-galactopyranosyl)-(1-4)-O-(2-N-allyloxycarbonyl-2-deoxy-β-D-glucopyranosyl)-(1-3)-O-β-D-galactopyranoside (Compound 11) which was identical to that produced in the following procedure.

EXAMPLE 11

Ethyl [sodium (5-acetamido-3,5-dideoxy-α-D-glycero-D-galactononulopyranosylonate)]-(2-3)-O-(β-D-galactopyranosyl)-(1-4)-O-(2-N-allyloxycarbonyl-2-deoxy-β-D-glucopyranosyl)-(1-3)-O-β-D-galactopyranoside (Compound 11)

The following describes the enzymatic conversion of a disaccharide (Compound 9) to produce the title compound (Compound 11) using galactosyl transferase and sialyl transferase.

To water (12L), N-[2-hydroxyethyl]piperazine-N'[2-ethanesulfonic acid] 0.410 Kg was added and the pH of the resulting solution was adjusted to 7.5. Bovine serum albumin (17 g) was added and the mixture stirred until a complete solution was obtained. Ethyl 3-O-(2-N-allyloxycarbonyl-2-amino-2-deoxy-β-D-glucopyranosyl)-β-D-galactopyranoside (Compound 9) (0.3 kg), glucose-1-phosphate (0.271 kg), phosphoenolpyruvate (0.177 kg), potassium chloride (0.087 kg), sodium azide (8.4 g), and uridine-5'-diphosphate (8.76 g) were added and the resulting mixture stirred until all of the solids are dissolved. Manganese chloride (1M, 506 mL) and magnesium chloride (1M, 168 mL) were then added. Pyruvate kinase (42,000 U), uridine-5'-diphosphateglycose pyrophosphorylase (2,000 U), inorganic pyrophosphatase (8,400 U), uridine-5'-diphosphategalactose epimerase (9 1,000 U), and uridine-5'-diphosphate-galactosyl transferase (8,850 U) were then added. The final volume of the reaction mixture was adjusted to 17 L with water. After 48 hours magnesium chloride (1M, 340 mL) was added. The reaction was monitored by TLC on silica gel developed with isopropanol:1M ammonium acetate 4:1. After 8–9 days TLC indicated that the reaction had proceeded to >95 percent at which time the following solution was prepared.

A solution of N-[2-hydroxyethyl]piperazine-N'-[2-ethanesulfonic acid] (0.528 kg) was prepared in water (15 L) and the pH of the resulting solution was adjusted to 7.5. Bovine serum albumin (22 g), sodium azide (11.5 g), sialic acid (0.242 kg), phosphoenolpyruvate (0.395 kg), cytidine-5'-monophosphate (25 g), adenosine-5'-triphosphate (4.7 g), manganese chloride (1M, 780 mL) are added. To this solution was added pyruvate kinase (207,000 U), myokinase (125,000 U), cytidine-5'-monophosphate-N-acetylneuraminic acid synthetase (3245 U), inorganic pyrophosphatase (9400 U), and α-2,3-sialyltransferase (1640 U). The volume of this mixture was adjusted to 22 L and this solution was added to the galactosyl transferase reaction. The reaction was monitored by TLC on silica gel developed with isopropanol:1M ammonium acetate 4:1. After 10–12 days, TLC indicated that the reaction had proceeded to give >95 percent of the title compound, Compound 11.

EXAMPLE 12

Ethyl [methyl (5-acetamido-3,5-dideoxy-4,7,8,9-tetra-O-acetyl-α-D-glycero-D-glycero-D-galacto-nonulopyranosylonate)]-(2-3)-O-(2,4,6-tri-O-acetyl-β-D-galactopyranosyl)-(1-4)-O-(3,6-di-O-acetyl-2-N-allyloxycarbonyl-2-deox-β-D-glucopyranosyl)-(1-3)-O-2,4,6-tri-O-acetyl-β-D-galactopyranoside
(Compound 12)

A solution (40 L) of ethyl [sodium (5-acetamido-3,5-dideoxy-α-D-glycero-D-galactononulopyranosylonate)]-(2-3)-O-(β-D-galactopyranosyl)-(1-4)-O-(2-N-allyloxycarbonyl-2-deoxy-β-D-glucopyranosyl)-β-D-galactopyranoside (Compound 11) was filtered through paper. The filtrate was evaporated to a thick syrup in a 50 L rotavapor. The syrup was coevaporated twice with pyridine (2×2 L), then kept under vacuum for 20 hours. The evaporation flask was charged with a solution of N,N-dimethylaminopyridine (20 g) in pyridine (12 L). The rotavapor bath was charged with ice-water mixture, and rotation was continued while acetic anhydride (6 L) was added during a period of one hour. Two hours after complete addition, more acetic anhydride (2 L) was added and the resulting mixture was left for 20 hours rotating slowly at room temperature. To ensure compete acetylation, more acetic anhydride (1 L) was added and the mixture was rotated for an additional 24 hours. The reaction was checked by TLC (ethyl acetate:hexane:ethanol, 10:10:3).

Upon complete reaction vacuum was applied and 14 L of distillate were collected. To the resulting residue, methanol (15 L) was added over a period of one hour and the mixture was rotated at room temperature for 20 hours. At this time, TLC on silica gel (ethyl acetate:hexane:ethanol, 10:10:3 and dichloromethane:acetone 3:2) showed complete conversion of the lactone to a slower-moving spot that was the methyl ester monohydroxy compound. The mixture was then concentrated (18 L evaporated) and the mixture was cooled in ice water while acetic anhydride (3 L) was added over a period of 30 minutes. The mixture was left for 20 hours. TLC on silica gel (dichloromethane:acetone 3:2) showed complete acetylation with the product running slightly faster.

Methanol (1 L) was added to destroy excess acetic anhydride during which a slight exotherm was noticed. After one hour, the mixture was concentrated to a syrup, which was transferred to a 50 L extractor with the aid of ethyl acetate-water mixture (13/13 L). The mixture was agitated vigorously. After phase separation, the lower aqueous layer was drawn off, and the remaining organic layer was filtered through paper. The filtrate was washed with 5 percent aqueous hydrochloric acid (15 L, the aqueous layer should still be strongly acidic to pH-paper after washing), and aqueous 1M sodium bicarbonate (15 L, the aqueous layer should still be alkaline to pH paper after washing). The organic layer was then transferred to a 20 L container, dried over anhydrous sodium sulfate and filtered.

The filtrate was concentrated to a semi-solid residue. This residue was dissolved in dichloromethane (3 L), and applied to a silica gel column (10 kg), packed in dichloromethane. Elution first with dichloromethane (25 L), then with 3:1 dichloromethane:acetone (25 L), and finally with 1:1 dichloromethane:acetone (50 L) gave fractions containing product. Base-line separation was achieved from the disaccharide material, but very little separation was achieved from the traces of slightly faster moving material. The fractions containing product were evaporated, and redissolved in dichloromethane (1.5 L). This solution was slowly added to a vigorously stirred mixture of ethyl ether (7.5 L) and hexane (10 L). The resulting precipitate was filtered and washed with 2:1 ether:hexane, air-dried overnight, then dried in high vacuum for 48 hours. The precipitate was shown to be the title Compound 12 by $^1$H-NMR, and contained a small amount of residual solvent (1–5 percent, weight/weight). $^1$H-NMR (CDCl$_3$) δ: 4.67(d, 1H, H-1"), 4.49(d, 1H, H-1'), 4.33 (d, 1H, H-1).

EXAMPLE 13

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-(2-amino-2-deoxy-3,6-di-O-acetyl-β-D-glucopyranosyl)-(1,3)-O-2,4,6-tri-O-acetyl-β-D-galactopyranoside (Compound To a stirred solution of ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-(2-allyloxycarbonylamido-2-deoxy-3,6-di-O-acetyl-β-D-glucopyranosyl)-(1,3)-O-2,4,6-tri-O-acetyl-β-D-galactopyranoside (Compound 12) (5.10 gm, 3.80 mmol) anhydrous THF under argon at room temperature was added polymethylhydrosiloxane (420 μL). The reaction mixture was put through a vacuum/purge cycle three times with argon to degas the solution. The flask was wrapped in aluminum foil to protect the solution from light, and the solution was treated with palladium tetrakistriphenylphosphine [Pd(PPh$_3$)$_4$; 158 mg, 0.14 mmol]. After stirring for 18 hours at room temperature, TLC in 10:1 CHCl$_3$:MeOH indicated complete consumption of Compound 12 and the presence of a single lower rf product. The reaction mixture was diluted with 600 mL of EtOAc and washed 1×200 mL with H$_2$O and 1'200 mL with saturated NaCl solution. The organic solution was dried (MgSO$_4$), filtered, concentrated by rotary evaporation, and flash chromatographed on a 65 mm×10" column of silica gel using 3:1 EtOAc:acetone as eluant. The product-containing fractions (as judged by TLC) were pooled and concentrated to provide Compound 13 (4.42 gm, 87 percent) as a tan solid. $^1$H-NMR (300 MHz, δ in ppm relative to CHCl$_3$) 5.50 (m, 1H), 5.44 (dd, J=6 Hz, J=2 Hz, 1H), 5.35–5.01 (m), 4.89 (m, 2H), 4.63 (d, J=6 Hz, 1H), 4.59-4.35 (m), 4.22–3.38 (m), 3.81 (s, 3H), 2.69 (m, 1H), 2.57 (dd, J=3 Hz, J=10 Hz, 1H), 2.27–1.85 (12s, 36H), 1.77 (dd, J=10 Hz, J=10 Hz, 1H), 1.21 (t, J=5 Hz, 3H).

EXAMPLE 14

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-(2-amino-2-deoxy-6-O-acetyl-β-D-glucopyranosyl)-(1,3)-O-2,4,6-tri-O-acetyl-β-D-galactopyranoside (Compound 14)

To a stirred solution of Compound 13 (4.42 gm, 3.29 mmol) in 366 mL of 4:1MeOH:H$_2$O at room temperature in a capped flask was added glacial acetic acid (188 μL, 3.29 mmol). The pale yellow solution was then heated to 50° C. After 48 hours, TLC in 10:1 CHCl$_3$:MeOH indicated nearly complete disappearance of Compound 13 and appearance of a predominant, slightly higher R$_f$ product. The reaction was cooled to room temperature, concentrated by rotary evaporation to an oil, and flash chromatographed on a 65mm×10" column of silica gel using 10:10:4 EtOAc:hexane:MeOH as eluant. The product-containing fractions (as judged by TLC) were pooled and concentrated to give Compound 14 (2.78 gm, 65 percent) as a foam. $^1$H-NMR (300 MHz, δ in ppm relative to CHCl$_3$) 5.50 (m, 1H), 5.40 (d, J=2 Hz, 1H), 5.25 (d, J=7 Hz, 1H), 5.17 (dd, J=6 Hz, J=7 Hz, 1H), 5.04 (dd, J=6 Hz, J=7 Hz, 1H), 4.89 (d, J=3 Hz, 1H), 4.63 (d, J=6 Hz, 1H), 4.59 (dd, J=3 Hz, J=7 Hz, 1H), 4.42–3.40 (m), 3.81 (s, 3H), 2.69 (m, 1H), 2.57 (dd, J=3 Hz, J=10 Hz, 1H), 2.27– 1.85 (12S, 36H), 1.77 (dd, J=10 Hz, J=10 Hz, 1H), 1.21 (t, J=5 Hz, 3H).

EXAMPLE 15

Ethyl [methyl (5-acetamido-3,5-dideoxy-4,7,8,9-tetra-O-acetyl -α-D-glycero-D-galacto-2-nonulopyranosylonate]-(2,3)-O-(2,4,6-tri-O-acetyl-β-D-galactopyranosyl)-(1,4)-O-(2-benzamido-2-deoxy-6-O-acetyl-β-D-glucopyranosyl)-(1,3)-O-2,4,6-tri-O-acetyl-β-D-galactopyranoside (Compound 15)

To a stirred solution of Compound 14 (150 mg, 0.12 mmol) in 2 mL of dichloromethane at room temperature under an argon atmosphere was added anhydrous NaHCO$_3$ (40 mg, 0.48 mmol), and benzoyl chloride (34 mg, 0.24 mmol, 28 μL). After stirring for 24 hours, TLC in 80:20 EtOAc:acetone indicated complete consumption of starting material and the appearance of a slightly higher R$_f$ material.

The reaction mixture was diluted with 150 mL of ethyl acetate and washed 1×50 mL with H$_2$O. The organic solution was dried (MgSO$_4$), filtered, concentrated, and flash chromatographed on a column of silica gel using 90:10 EtOAc:acetone as eluant. The product-containing fractions (as judged by TLC) were pooled and concentrated by rotary evaporation and then by high vacuum to a cream waxy solid, Compound 15: (140 mg, 83 percent). $^1$H-NMR (300 MHz, δ in ppm relative to CHCl$_3$) 7.75 (d, J=7 Hz, 2H), 7.45 (d, J=7 Hz, 1H), 7.39 (dd, J=7 Hz, J=7 Hz, 2H), 6.45 (d, J=5 Hz, 1H), 5.50 (m, 1H), 5.40 (d, J=2 Hz, 1H), 5.37 (d, J=2 Hz, 1H), 5.27 (m, 1H), 5.09 (m, 1H), 4.82 (d, J=3 Hz, 1H), 4.63 (d, J=6 Hz, 1H), 4.59 (dd, J=3 Hz, J=7 Hz, 1H), 4.39–3.40 (m), 3.81 (s, 3H), 3.19 (m, 1H), 2.57 (dd, J=3 Hz, J=10 Hz, 1H), 2.27–1.85 (12s, 36H), 1.77 (dd, J=10 Hz, J=10 Hz, 1H), 1.15 (t, J=5 Hz, 3H).

EXAMPLE 16

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-[(2,3,4-tri-O-benzyl-α-L-fucopyranosyl)-(1,3)]-O-(2-benzamido-2-deoxy-3,6-di-O-acetyl-β-D-glucopyranosyl)-(1,3)-O-2,4,6-tri-O-acetyl-β-D-galactopyranoside (Compound 16)

To a stirred solution of Compound 15 (140 mg, 0.1 mmol) in 1 mL of dichloroethane at room temperature under an argon atmosphere were added powdered, flame-dried 4 Å molecular sieves (100 mg), tetramethylurea (120 uL, 1 mmol), and tri-O-benzyl fucosyl fluoride (218 mg, 0.5 mmol). After stirring for one hour at room temperature, the reaction was cooled to −20° C. and treated with SnCl$_2$ (95 mg, 0.5 mmol) and AgClO$_4$ (126 mg, 0.5 mmol). The reaction was then allowed to slowly warm to room temperature. After stirring for 24 hours, TLC in 10:1 CHCl$_3$:MeOH indicated near complete consumption of starting material and the appearance of a slightly lower R$_f$ material.

The reaction mixture was filtered through a plug of celite with 50 mL of dichloromethane, and the filtrate was washed 2×50 mL with H$_2$O. The organic solution was dried (MgSO$_4$), filtered, concentrated, and flash chromatographed on a 20mm×6" column of silica gel using 10:10:3 EtOAc:hexane:MeOH as eluant. The product-containing fractions (as judged by TLC) were pooled and concentrated by rotary evaporation and then by high vacuum to a white film, Compound 16 (140 mg, 77 percent). $^1$H-NMR (300 MHz, a in ppm relative to CHCl$_3$) 7.46 (d, J=7 Hz, 2H), 7.35–7.12 (m, 18H), 6.45 (d, J=6 Hz, 1H), 3.82 (s, 3H), 3.20 (m, 1H), 2.55 (dd, J=4 Hz, J=12 Hz, 1H), 1.18 (d, J=6 Hz, 3H), 1.10 (t, J=6 Hz, 3H).

EXAMPLE 17

Ethyl (5-acetamido-3,5-dideoxy-α-D-glycero-D-galacto-2-nonulopyranosylonate)-(2,3)-O-(β-D-galactopyranosyl)-(1,4)-O-[(α-L-fucopyranosyl)-(1,3)]-O-(2-benzamido-2-deoxy-β-D-glucopyranosyl)-(1,3)-O-β-D-galactopyranoside (Compound 17)

To a stirred solution of Compound 16 (140 mg, 77 μmol) in 4 mL of methanol was added palladium hydroxide on carbon (140 mg, 20 percent by weight palladium). The slurry was then put through a vacuum/purge cycle three times with hydrogen gas and then held under hydrogen at one atmosphere pressure at room temperature. After one hour, TLC in 5:1 EtOAc:MeOH indicated complete disappearance of Compound 16 and the appearance of a single lower R$_f$ material. The slurry was filtered through a plug of celite with 50 mL of methanol and concentrated by rotary evaporation to an oil.

This oil was dissolved in 5 mL of 4:1MeOH:H$_2$O and stirred at room temperature in a capped flask. Sodium methoxide powder (140 mg, 2.6 mmol) was added to the stirred solution. After 16 hours, TLC in 60:50:15 CHCl$_3$:MeOH:15 mM CaCl$_2$ indicated complete disappearance of starting material and the appearance of a single lower R$_f$ product.

The mixture was treated with 1 gram of Dowex 50×8-400 cation exchange resin (hydrogen form, freshly methanol washed) and stirred for one minute. The mixture was filtered through a fritted funnel and the filtrate concentrated by rotary evaporation to an oil. This material was chromatographed on a 40 mm×8" column of Bio-Rad Bio-Gel P2 gel filtration media (mesh size: fine) using 0.1M ammonium bicarbonate as eluant. The product-containing fractions (as judged by TLC) were pooled and lyophilized to a white powder for Compound 17 (60 mg, 72 percent). $^1$H-NMR (300 MHz, δ in ppm relative to HOD) 7.70 (d, J=7 Hz, 2H), 7.55 (d, J=7 Hz, 1H), 7.47 (dd, J=7 Hz, J=7 Hz, 2H), 5.08 (d, J=4 Hz, 1H), 4.50 (d, J=8 Hz, 1H), 4.27 (d, J=8 Hz, 1H), 4.10 (d, J=3 Hz, 1H), 4.05–3.40 (m), 2.70 (dd, J=4.6 Hz, J=12.4 Hz, 1H), 1.97 (s, 3H), 1.74 (dd, J=12.4 Hz, J=12.4 Hz, 1H), 1.10 (t, J=7 Hz, 3H), 1.07 (d, J=7 Hz, 3H).

EXAMPLE 18

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-[(α-L-fucopyranosyl)-(1,3)]-O-(2-2'-napthamido-2-deoxy-3,6-di-O-acetyl-β-D-glucopyranosyl)-(1,3)-O-2,4,6-tri-O-acetyl-β-D-galactopyranoside (Compound 29)

To a stirred solution of Compound 25 (prepared analogously to Compound 16; 90 mg, 48 μmol) in 5 mL of methanol was added palladium hydroxide on carbon (40 mg, 40 percent by weight palladium). The slurry was put through a vacuum/purge cycle three times with hydrogen gas and held under hydrogen at one atmosphere pressure at room temperature. After 24 hours, TLC in 90:10 CH$_2$C$_{12}$:MeOH indicated complete disappearance of Compound 25 and the appearance of a single lower R$_f$ material. The slurry was filtered through a plug of celite with 50 mL of methanol and concentrated by rotary evaporation to a cream waxy solid. The product was treated by flash column chromatography on a column of silica gel using 90:10 CH$_2$Cl$_2$:MeOH as eluant. The product containing fractions (as judged by TLC) were then pooled and concentrated to give Compound 29 (55 mg, 72%) as a white waxy solid. $^1$H-NMR (300 MHz, δ in ppm relative to CHCl$_3$) 8.39 (s, 1H), 7.94 (d, J=7 Hz, 1H), 7.82 (m, 2H), 7.57 (m, 2H), 7.37 (m, 1H), 5.57-5.41 (m, 3H), 5.22 (d, J=7 Hz, 1H), 5.15 (m, 1H), 4.97-4.39 (m), 4.35 (d, J=4 Hz, 2H), 4.19-3.42 (m), 3.81 (s, 3H), 3.23 (m, 1H), 2.75 (bs, 1H), 2.57 (dd, J=3 Hz, J=10 Hz, 1H), 2.27–1.85 (12s, 36H), 1.77 (dd, J=10 Hz, J=10 Hz, 1H), 1.23 (d, J=5 Hz, 3H, 1.05 (t, J=5 Hz, 3H).

Following procedures substantially similar to those discussed above and as to Scheme 3 for the conversion of Compound 14 into Compounds 15, 16 and 17, Compounds of 18–38 were also prepared. Tables 1, 2 and 3, below show the generalized structures for groups of compounds corresponding to Compounds 15, 16 or 17, and provides other pertinent data for each of those compounds. Table 1 shows the acylating agent used to prepare each R$^1$ group. Tables 1–3 are followed by NMR and added data for several of those compounds, and inhibitor Compounds 30–38, including last step yields.

TABLE 1

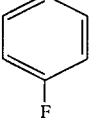

| Compound # | R[1] Group Acylating agent | Yield | $R_f$ (solvent) |
|---|---|---|---|
| 18 | COCl — C6H4 — F (4-fluorobenzoyl chloride) | 148 mg, 87% | 0.4 (90:10 EtOAc:acetone) |
| 19 | COCl — C6H4 — NO2 (4-nitrobenzoyl chloride) | 136 mg, 78% | 0.43 (90:10 EtOAc:acetone) |
| 20 | COCl — CH=CH — C6H4 — NO2 (4-nitrocinnamoyl chloride) | 133 mg, 78% | 0.40 (90:10 EtOAc:acetone) |
| 21 | 2-naphthoyl chloride | 143 mg, 82% | 0.45 (90:10 EtOAc:acetone) |

TABLE 2

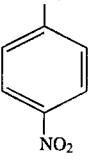

| Compound # | Glycosyl acceptor | Yield | $R_f$ (solvent) |
|---|---|---|---|
| 22 | 18 | 135 mg, 74% | 0.35 (92:8 EtOAc:acetone) |
| 23 | 19 | 100 mg, 58% | 0.39 (92:8 EtOAc:acetone) |
| 24 | 20 | 105 mg, 65% | 0.37 (92:8 EtOAc:acetone) |
| 25 | 21 | 100 mg, 58% | 0.37 (92:8 EtOAc:acetone) |

TABLE 3

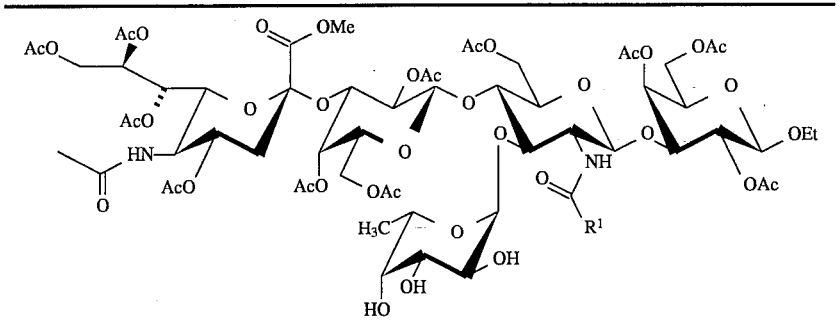

| Compound # | Benzylated pentasaccharide | Yield | $R_f$ (solvent) |
|---|---|---|---|
| 26 | 22 | 62 mg, 60% | 0.32 (90:10 $CH_2Cl_2$:MeOH) |
| 27 | 23 | 35 mg, 50% | 0.39 (90:10 $CH_2Cl_2$:MeOH) |
| 28 | 24 | 73 mg, 65% | 0.31 (90:10 $CH_2Cl_2$:MeOH) |

EXAMPLE 19

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-(2-benzyloxycarbonylamido-2-deoxy-6-O-acetyl-β-D-glucopyranosyl)-(1,3)-O-2,4,6-tri-O-acetyl-β-D-galactopyranoside (Compound 39)

A solution of benzyloxycarbonyl chloride (CBZ-$C_1$) (1.2 ml, 8.4 mmol) in $CH_2Cl_2$ (2.0 ml) was added dropwise to a mixture of Compound 14a (10.8 g, 8.3 mmol) and NaCHO₃ (1.4 g, 16.6 mmol) in $CH_2Cl_2$ (100 ml), and the reaction mixture was stirred overnight (about 18 hours). To this mixture were added NaHCO₃ (1.4 g, 16.6 mmol) and CBZ-Cl (1.2 ml, 8.4 mmol), and the resulting mixture was stirred an additional four hours. The resulting mixture was diluted with AcOEt, washed with $H_2O$, dried over $MgSO_4$, filtered, and concentrated. The residue was chromatographed on silica gel to provide Compound 39 (7.75 g, 65 percent yield) as a white solid.

EXAMPLE 20

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-[(2,3,4-tri-O-benzyl-β-L-fucopyranosyl)-(1,3)]-O-(2-benzyloxycarbonylamido-2-deoxy-3,6-di-O-acetyl-β-D-glucopyranosyl)-(1,3)-O-2,4,6-tri-O-acetyl-β-D-galactopyranoside (Compound 40)

To a stirred solution of Compound 39 (3.90 g, 2.72 mmol) in 100 ml of $ClCH_2CH_2Cl$ were added powdered molecular sieves (MS4A) (12 g), tetramethyl urea (TMU) (3.25 ml, 27.2 mmol) and 2,3,4-tri-O-benzyl-L-fucosyl fluoride (CMH-048, 5.94 g, 13.6 mmol). After stirring for 90 minutes at room temperature, the mixture was shielded from light, cooled to −20° C. and treated with $SnCl_2$ (2.59 g, 13.6 mmol) and $AgClO_4$ (98 percent, 2.88 g, 13.6 mmol). The reaction mixture was permitted to warm to room temperature over a 90 minute time period, and stirred for 24 hours. In order to complete the reaction, TMU (1.95 ml, 16.3 mmol), CMH-048 (3.56 g, 8.16 mmol), $SnCl_2$ (1.55 g, 8.17 mmol) and $AgClO_4$ (1.73 g, 8.17 mmol) were added again to the mixture at zero degrees C., which was then permitted to slowly warm to room temperature. After 48 hours, the resulting mixture was filtered through a pad of Celite and the filtrate was washed with $H_2O$. The organic phase was dried over $Na_2SO_4$, filtered, concentrated, and chromatographed on silica gel (Hexane/AcOEt/MeOH=10/10/2) to provide Compound 40 (3.65 g, 73 percent yield) and recovered starting material, Compound 39, (672 mg, 17 percent yield).

EXAMPLE 21

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-[(α-L-fucopyranosyl)-(1,3)]-O-(2-amino-2-deoxy-3,6-di-O-acetyl-β-D-glucopyranosyl)-(1,3)-O-2,4,6-tri-O-acetyl-β-D-galactopyranoside (Compound 41)

The mixture of Compound 40 (3.06 g, 1.66 mmol), HCOONH₄ (1.05 g, 16.6 mmol) and 10 percent Pd-C (wet, 3.0 g) in EtOH (80 ml) was refluxed with stirring for 9.5 hours. To this mixture were added more HCOONH₄ (1.05 g, 16.6 mmol) and 10 percent Pd-C (3.0 g), and the resulting mixture was refluxed an additional 11 hours. That resulting mixture was filtered through a pad of Celite and concentrated to provide Compound 41 (2.30 g, 96 percent yield) as a white solid.

EXAMPLE 22

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-[(α-L-fucopyranosyl)-(1,3)]-O-[2-(3,5-dichlorobenzoylamido)-2-deoxy-3,6-di-O-acetyl-β-D-glucopyranosyl]-(1,3)-O-2,4,6-tri-O-acetyl-B-D-galactopyranoside (Compound 42)

To a stirred solution of Compound 41 (40 mg, 0.028 mmol) in $CH_2Cl_2$ (8.9 ml) were added NaHCO₃ (46 mg, 0.54 mmol) and 3,5-dichlorobenzoyl chloride (58.6 mg, 0.28 mmol). After 12 hours at room temperature, the reaction mixture was diluted with EtOAc and washed with $H_2O$. The organic phase was dried over $MgSO_4$, filtered, and evaporated to afford crude Compound 42 (98.4 mg) as a pale yellow oil.

EXAMPLE 23

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-[(α-L-fucopyranosyl)-(1,3)]-O-[2-(3,5-dichlorobenzamido)-2-deoxy-3,6-di-O-acetyl-β-D-glucopyranosyl]-(1,3)-O-2,4,6-tri-O-acetyl-β-D-galactopyranoside (Compound 43)

To a stirred solution of crude Compound 42 (98.4 mg) in MeOH (8.9 ml) was added 28 percent NaOMeMeOH (300 µl). After 48 hours at room temperature, the mixture was neutralized with DOWEX 50W-X8 (H$^+$-form) and filtered. The filtrate was concentrated, diluted with EtOAc, and extracted with H$_2$O. The aqueous phase was evaporated to give the corresponding ester. The ester was treated with 1N-NaOH (200 µl) in H$_2$O (5.0 ml). The mixture was stirred for 12 hours at room temperature, neutralized with DOWEX 50W-X8 (H$^+$-form) and filtered. The filtrate was concentrated, purified by Gel (p-2) filtration (H$_2$O as eluent), and lyophilized to afford Compound 43 (31.6 mg, quantitative yield) as a white powder.

$^1$H-NMR (270 MHz, δ in ppm relative to H$_2$O) 7.61 (s, 3H), 5.00 (d, J=3.96 Hz, 1H), 4.47 (d, J=7.59 Hz, 1H), 4.26 (d, J=7.92 Hz, 1H), 4.09 (d, J=2.97 Hz, 1H), 4.04–3.30 (m), 2.67 (m, 1H), 1.94 (s, 3H), 1.72 (t, J=11.88 Hz, 1H), 1.09 (m, 6H).

NMR data of Compounds 18–28

Ethyl[methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-(2-p-fluorobenzamido-2-deoxy-6-O-acetyl-β-D-glucopyranosyl)-(1,3)-O-2,4,6-tri-O-acetyl-β-D-galactopyranoside (Compound 18)

$^1$H-NMR (300 MHz, δ in ppm relative to CHCl$_3$) 7.79 (m, 2H), 7.15 (m, 2H), 6.41 (d, J=5 Hz, 1H), 5.53 (m, 1H), 5.42 (m, 1H), 5.23 (d, J=7 Hz, 1H), 5.17 (m, 2H), 4.89 (d, J=3 Hz, 1H), 4.63 (d, J=6 Hz, 1H), 4.59 (dd, J=3 Hz, J=7 Hz, 1H), 4.42–3.40 (m), 3.81 (s, 3H), 3.19 (m, mH), 2.57 (dd, J=3 Hz, J=10 Hz, 1H), 2.27–1.85 (128 s, 36H), 1.77 (dd, J=10 Hz, J=10 Hz, 1H), 1.15 (t, J=5 Hz, 3H).

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-(2-p-nitrobenzamido-2-deoxy-6-O-acetyl-β-D-glucopyranosyl)-(1,3)-O-2,4,6-tri-O-acetyl-β-D-galactopyranoside (Compound 19)

$^1$H-NMR (300 MHz, δ in ppm relative to CHCl$_3$) 8.22 (d, J=8 Hz, 2H), 7.95 (d, J=8 Hz, 2H), 6.81 (d, J=5 Hz, 1H), 5.59–5.37 (m, 2H), 5.21 (d, J=4 Hz, 1H), 5.11 (m, 2H), 4.89 (d, J=2 Hz, 1H), 4.63 (d, J=5 Hz, 1H), 4.59 (dd, J=1 Hz, J=7 Hz, 1H), 4.42–3.40 (m), 3.79 (s, 3H), 3.19 (m, 1H), 2.57 (dd, J=3 Hz, J=10 Hz, 1H), 2.27–1.85 (128, 36H), 1.77 (dd, J=10 Hz, J=10 Hz, 1H), 1.15 (t, J=5 Hz, 3H).

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-[2-(E-1-oxo-3-phenylprop-2-ene)amino-2-deoxy-6-O-acetyl-β-D-glucopyranosyl]-(1,3)-O-2,4,6-tri-O-acetyl-β-D-galactopyranoside (Compound 20)

$^1$H-NMR (300 MHz, δ in ppm relative to CHCl$_3$) 7.57 (d, J=11 Hz, 1H), 7.45–7.25 (m, 5H), 6.39 (d, J=11 Hz, 1H), 5.87 (d, J=4 Hz, 1H), 5.45 (m, 1H), 5.39 (m, 2H), 5.21 (t, J=7 Hz, 1H), 5.17–4.97 (m, 2H), 4.89 (d, J=2 Hz, 1H), 4.63 (d, J=5 Hz, 1H), 4.59 (dd, J=1 Hz, J=7 Hz, 1H), 4.42–3.40 (m), 3.79 (s, 3H), 3.05 (m, 1H), 2.57 (dd, J=3 Hz, J=10 Hz, 1H), 2.27–1.85 (128, 36H), 1.77 (dd, J=10 Hz, J=10 Hz, 1H), 1.15 (t, J=5 Hz, 3H).

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-(2-2'-napthamido-2-deoxy-6-O-acetyl-β-D-glucopyranosyl)-(1,3)-O-2,4,6-tri-O-acetyl-β-D-galactopyranoside (Compound 21)

$^1$H-NMR (300 MHz, δ in ppm relative to CHCl$_3$) 8.25 (s, 1H), 7.95–7.42 (m, 6H), 6.58 (d, J=5 Hz, 1H), 5.53 (m, 1H), 5.44 (d, J=2 Hz, 1H), 5.41–5.23 (m), 5.17–5.01 (m), 4.89 (d, J=3 Hz, 1H), 4.63 (d, J=6 Hz, 1H), 4.59 (dd, J=3 Hz, J=7 Hz, 1H), 4.42–3.40 (m), 3.81 (s, 3H), 3.27 (m, 1H), 2.57 (dd, J=3 Hz, J=10 Hz, 1H), 2.27–1.85 (128, 36H), 1.77 (dd, J=10 Hz, J=10 Hz, 1H), 1.15 (t, J=5 Hz, 3H).

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-[(2,3,4-tri-O-benzyl-α-L-fucopyranosyl)-(1,3)]-O-(2-p-fluorobenzamido-2-deoxy-3,6-di-O-acetyl-β-D-glucopyranosyl)-(1,3)-O-2,4,6-tri-O-acetyl-b-D-galactopyranoside (Compound 22)

$^1$H-NMR (300 MHz, δ in ppm relative to CHCl$_3$) 7.42 (m, 2H), 7.39–7.17 (m, 15H), 6.95 (t, J=7 Hz, 2H), 6.45 (d, J=5 Hz, 1H), 5.57–5.37 (m, 3H), 5.27 (d, J=7 Hz,1H), 5.17–4.45 (m), 4.39 (d, J=7 Hz, 1H), 4.25–3.41 (m), 3.81 (s, 3H), 3.21 (m, 1H), 2.57 (dd, J=3 Hz, J=10 Hz, 1H), 2.27–1.85 (12s, 36H), 1.77 (dd, J=10 Hz, J=10 Hz, 1H), 1.19 (d, J=5 Hz, 3H), 1.15 (t, J=5 Hz, 3H).

Ethyl [methyl (5-acetamido-3,5-dideoxy-4,7,8,9-tetra-O-acetyl-β-D-glycero-D-galacto-2-nonulopyranosylonate]-(2,3)-O-(2,4,6-tri-O-acetyl-β-D-galactopyranosyl)-(1,4)-O-[(2,3,4-tri-O-benzyl-α-L-fucopyranosyl)-(1,3)]-O-(2-p-nitrobenzamido-2-deoxy-3,6-di-O-acetyl-β-D-glucopyranosyl)-(1,3)-O-2,4,6-tri-O-acetyl-β-D-galactopyranoside (Compound 23)

$^1$H-NMR (300 MHz, δ in ppm relative to CHCl$_3$) 8.15 (d, J=8 Hz, 2H), 7.55 (d, J=8 Hz, 2H), 7.41–7.15 (m, 15H), 6.63 (d, J=5 Hz, 1H), 5.48 (m, 1H), 5.43 (dd, J=6 Hz, J=2 Hz, 1H), 5.37 (d, J=6 Hz,1H), 5.19 (d, J=8 Hz, 1H), 5.15–4.45 (m), 4.42 (t, J=4 Hz, 1H), 4.25 (m, 2H), 4.18–3.40 (m), 3.82 (s, 3H), 3.25 (m, 1H), 2.59 (dd, J=3 Hz, J=10 Hz, 1H), 2.27–1.85 (12s, 36H), 1.77 (dd, J=10 Hz, J=10 Hz, 1H), 1.19 (d, J=5 Hz, 3H), 1.15 (t, J=5 Hz, 3H).

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-[(2,3,4-tri-O-benzyl-α-L-fucopyranosyl)-(1,3)]-O-[2(E-1-oxo-3-phenylprop-2-ene)amino-2-deoxy-3,6-di-O-acetyl-β-D-glucopyranosyl]-(1,3)-O-2,4,6-tri-O-acetyl-β-D-galactopyranoside (Compound 24)

$^1$H-NMR (300 MHz, δ in ppm relative to CHCl$_3$) 7.42 (d, J=11 Hz, 1H), 7.39–7.15 (m, 20H), 5.94 (d, J=11 Hz, 1H), 5.85 (d, J=4 Hz, 1H), 5.55–5.29 (m, 4H), 5.17–4.42 (m), 4.25 (m, 2H), 4.17–3.40 (m), 3.79 (s, 3H), 3.05 (m, 1H), 2.57 (dd, J=3 Hz, J=10 Hz, 1H), 2.27–1.85 (128, 36H), 1.77 (dd, J=10 Hz, J=10 Hz, 1H), 1.19 (d, J=5 Hz, 3H), 1.15 (t, J=5 Hz, 3H).

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-[(2,3,4-tri-O-benzyl-α-L-fucopyranosyl)-(1,3)]-O-(2-2'-napthamido-2-deoxy-3,6-di-O-acetyl-β-D-glucopyranosyl)-(1,3)-O-2,4,6-tri-O-acetyl-β-D-galactopyranoside (Compound 25)

$^1$H-NMR (300 MHz, δ in ppm relative to CHCl$_3$) 8.13 (s, 1H), 7.84 (d, J=7 Hz, 1H), 7.78 (d, J=7 Hz, 1H , 7.57 (m, 2H), 7.37–7.11 (m, 16H), 6.98 (d, J=7 Hz, 1H, 6.65 (d, J=5 Hz, 1H), 5.57–5.35 (m, 2H), 5.22 (d, J=7 Hz, 1H), 5.15–5.01 (m, 3H), 4.97–4.45 (m), 4.25 (m, 2H, 4.19–3.42 (m), 3.81 (s, 3H), 3.23 (m, 1H), 2.57 (dd, J=3 Hz, J=10 Hz, 1H), 2.27–1.85 (12s, 36H), 1.77 (dd, J=10 Hz, J=10 Hz, 1H), 1.19 (d, J=5 Hz, 3H), 1.05 (t, J=5 Hz, 3H).

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-[(α-L-fucopyranosyl)-(1,3)]-O-(2-p-fluorobenzamido-2-deoxy-3,6-di-O-acetyl-β-D-glucopyranosyl)-(1,3)-O-2,4,6-tri-O-acetyl-β-D-galactopyranoside (Compound 26)

$^1$H-NMR (300 MHz, δ in ppm relative to CHCl$_3$) 7.83 (m, 2H), 7.17 (m, 2H), 5.45 (m, 1H), 6.40 (m, 2H), 5.23 (d, J=5 Hz, 1H), 5.17–4.75 (m,3H), 4.77–4.45 (m, 4H), 4.36 (m, 2H), 4.19–3.41 (m), 3.81 (s, 3H), 3.09 (bs, 1H), 2.62 (m, 1H), 2.57 (dd, J=3 Hz, J=10 Hz, 1H), 2.27–1.85 (12s, 36H), 1.77 (dd, J=10 Hz, J=10 Hz, 1H), 1.24 (d, J=5 Hz, 3H), 1.15 (t, J=5 Hz, 3H).

Ethyl [methyl (5-acetamido-3,5-dideoxy-4,7,8,9-tetra-O-acetyl-α-D-glycero-D-galacto-2-nonulopyranosylonate]-(2,3)-O-(2,4,6-tri-O-acetyl-β-D-galactopyranosyl)-(1,4)-O-[(α-L-fucopyranosyl)-(1,3)]-O-(2-p-aminobenzamido-2-deoxy-3,6-di-O-acetyl-β-D-glucopyranosyl)-(1,3)-O-2,4,6-tri-O-acetyl-β-D-galactopyranoside (Compound 27)

$^1$H-NMR (300 MHz, δ in ppm relative to CHCl$_3$)) 7.61 (d, J=8 Hz, 2H), 2H), 6.75 (d, J=5 Hz, 1H), 6.57 (d,J=8 Hz, 2H), 5.57 (m, 1H), 5.43 (dd, J=6 Hz, J=2 Hz, 1H), 5.2 7 (d, J=2 Hz, 1H), 5.19 (d, J=8 Hz, 1H), 5.09 (m, 1H), 4.9 5 (m, 2H), 4.77–4.63 (m), 4.55 (dd, J=7 Hz, J=1 Hz, 1H), 4.42 (t, J=4 Hz, 1H), 4.35 (m, 2H), 4.21–3.38 (m), 3.8 2 (s, 3H), 3.17 (m, 1H), 2.95 (bs, 1H), 2.59 (dd, J=3 Hz, J=10 Hz, 1H), 2.42 (bs, 1H), 2.27–1.85 (12s, 36H), 1.77 (dd, J=10 Hz, J=10 Hz, 1H), 1.22 (d, J=5 Hz, 3H), 1.15 (t, J=5 Hz, 3H).

Ethyl [methyl (5-acetamido 3 5-dideoxy-4,7,8,9tetra-O-acetyl-α-D-glycero-D-galacto-2-nonulopyranosylonate]-(2,3)-O-(2,4,6-tri-O-acetyl -β-D-galactopyranosyl)-(1,4)-O-[(α-L-fucopyranosyl)-(1,3)]-O-[2-(3'-phenyl)-propionamido-2-deoxy-3,6-di-O-acetyl-β-D-glucopyranosyl]-(1,3)-O-2,4,6-tri-O-acetyl-β-D-galactopyranoside (Compound 28)

$^1$H-NMR (300 MHz, δ in ppm relative to CHCl$_3$) 7.29(m, 5H), 6.39 (d, J=2 Hz, 1H), 5.85 (d, J=4 Hz, 1H), 5.55–5.19 (m, 5H), 5.11 (t, J=5 Hz, 1H), 4.95 (m, 4H), 4.71–4.35 (m), 4.17–3.22 (m), 3.79 (s, 3H), 2.95 (t, J=3H, 2H), 2.57 (dd, J=3 Hz, J=10 Hz, 1H), 2.47 (t, J=3 Hz, 2H), 2.27–1.85 (12s, 36H), 1.77 (dd, J=10 Hz, J=10 Hz, 1H), 1.24 (d, J=5 Hz, 3H), 1.15 (t, J=5 Hz, 3H).

Data for Compounds 30–38

Ethyl [(5-acetamido-3,5-dideoxy-α-D-glycero-D-galacto-2-nonulopyranosylonate]--(2,3)-O-(β-D-galactopyranosyl)-(1,4)-O-[(α-L-fucopyranosyl)-(1,3)]-O-(2-p-fluorobenzamido-2-deoxy-β-D-glucopyranosyl)-(1,3)-O-β-D-galactopyranoside (Compound 30)

$R_f$=0.62 (3:1 i-PrOH:NH$_4$OAc), white solid, 41 mg, 96 percent.

$^1$H-NMR (300 MHz, δ in ppm relative to H$_2$O) 7.83 (m, 2H, aromatic), 7.25 (m, 2H, aromatic), 5.18 (d, J=5 Hz, H-1 (fuc), 1H), 4.95 (m), 4.56 (d, J=8 Hz, 1H), 4.37 (d, J=8 Hz, 1H), 4.19 (d, J=3.5 Hz, 1H), 4.15–3.42 (m), 2.77 (dd, J=3 Hz, J=10 Hz, 1H), 2.05 (s, 3H, NAc), 1.79 (dd, J=10 Hz, J=10 Hz, 1H), 1.19 (m, 3H).

Ethyl [(5-acetamido-3,5-dideoxy-α-D-glycero-D-galacto-2-nonulopyranosylonate]-(2,3)-O-(β-D-galactopyranosyl)-(1,4)-O-[(α-L-fucopyranosyl)-(1,3)]-O-(2-p-aminobenza-mido-2-deoxy-β-D-glucopyranosyl)-(1,3)-O-β-D-galactopyranoside (Compound 31)

$R_f$=0.52 (3:1 i-PrOH:NH$_4$OAc), white solid, 26 mg, 96 percent.

$^1$H-NMR (300 MHZ, δ in ppm relative to H$_2$O) 7.65 (d, J=9 Hz, 2H, aromatic), 6.82 (d, J=9 Hz, 2H), 5.19 (d, J=3 Hz, H-1-fuc, 1H), 4.95 (m), 4.59 (d, J=8 Hz, 1H), 4.38 (d, J=8 Hz, 1H), 4.19 (d, J=2 Hz, 1H), 4.15–3.42 (m), 3.19 (q, J=6 Hz, 2H, CH$_2$CH$_3$), 2.79 (dd, J=3 Hz, J=11 Hz, H$_{eq}$-3 (sialic acid), 1H), 2.05 (s, 3H, NAc), 1.77 (dd, J=10 Hz, J=10 Hz, H$_{ax}$-3 (sialic acid), 1H), 1.19 (d, J=6 Hz, 3H, H-6-fuc), 1.17 (t, J=6 Hz, 3H).

Ethyl [(5-acetamido-3,5-dideoxy-α-D-glycero-D-galacto-2-nonulopyranosylonate]-(2,3)-O-(β-D-galactopyranosyl)-(1,4)-O-[(α-L-fucopyranosyl)-(1,3)]-O-[(2-(3'-phenyl)-propionamido-2-deoxy-β-D-glucopyranosyl)-(1,3)-O-β-D-galactopyranoside (Compound 32)

$R_f$=0.62 (3:1 i-PrOH:NH$_4$OAc), white solid, 47 mg, 98 percent.

$^1$H-NMR (300 MHZ, δ in ppm relative to H$_2$O) 7.42–7.25 (m, 5H), 5.19 (d, J=4 Hz, H-1-fuc, 1H), 4.95 (m), 4.57 (d, J=8 Hz, 1H), 4.38 (d, J=8 Hz, 1H), 4.13 (d, J=2 Hz, mH), 4.11–3.42 (m), 2.95 (t, J=5 Hz,2H, a–CH$_2$), 2.75 (dd, J=3 Hz, J=10 Hz, H$_{eq}$-3 (sialic acid), 1H), 2.63 (t, J=5 Hz, 2H, CH$_2$Ph), 2.05 (s, 3H, NAc), 1.80 (dd, J=10 Hz, J=10 Hz, H$_{ax}$-3 (sialic acid), 1H), 1.24 (t, J=5 Hz, 3H), 1.18 (d, J=5 Hz, 3H).

Ethyl (5-acetamido-3,5-dideoxy-α-D-glycero-D-galacto-2-nonulopyranosylonate)-(2,3)-O-(β-D-galactopyranosyl)-(1,4)-O-[(α-L-fucopyranosyl)-(1,3)]-O-(2,2'-napthamido-2-deoxy-β-D-glucopyranosyl)-(1,3)-O-β-D-galactopyranoside (Compound 33)

$R_f$=0.52 (3:1 i-PrOH:NH$_4$OAc), white solid, 35 mg, 96 percent.

$^1$H-NMR (300 MHz, δ in ppm relative to H$_2$O) 8.39 (s, 1H), 8.02 (m, aromatic, 2H), 7.82 (d, J=7 Hz, aromatic, 1H), 7.63 (m, aromatic, 3H),5.19 (d, J=4 Hz, H-1(fuc), 1H), 4.95 (m), 4.57 (d, J=8 Hz, 1 H), 4.35 (d, J=8 Hz, 1H), 4.19 (d, J=2 Hz, 1H), 4.15–3.42 (m), 2.77 (dd, J=3 Hz, J=11 Hz, H$_{eq}$-3 (sialic acid), 1H), 2.05 (s, 3H, NAc), 1.77 (dd, J=10 Hz, J=10 Hz, H$_{ax}$-3 (sialic acid), 1H), 1.19 (d, J=6 Hz, 3H, H-6-fuc), 1.05 (t, J=6 Hz, 3H).

Ethyl [(5-acetamido-3,5-dideoxy-α-D-glycero-D-galacto-2-nonulopyranosylonate]-(2,3)-O-(β-D-galactopyranosyl)-(1,4)-O-[(α-L-fucopyranosyl)]-(1,3)-O-(2,2'-phenylaceta-mido-2-deoxy-β-D-glucopyranosyl)-(1,3)-O-β-D-galactopyranoside (Compound 34)

$R_f$=0.62 (4.5:1 i-PrOH:NH$_4$OAc), white solid, 24 mg, 68 percent.

$^1$H-NMR (300 MHz, δ in ppm relative to H$_2$O) 7.45–7.27 (m, 5H), 4.85 (d, J=3 Hz, H-1-fuc, 1H), 4.75 (m), 4.55 (d, J=8 Hz, 1H), 4.38 (d, J=8 Hz, 1H), 4.13 (d,J=2 Hz, 1H), 4.09–3.42 (m), 2.78 (dd, J=3 Hz, J=10 Hz, H$_{eq}$-3 (sialic acid), 1H), 2.05 (2s, 5H, NAc, PhCH$_2$), 1.80 (dd, J=10 Hz, J=10 Hz, H$_{ax}$-3 (sialic acid), 1H), 1.24 (t, J=5 Hz, 3H), 1.18 (d, J=5 Hz, 3H).

Ethyl [(5-acetamido-3,5-dideoxy-α-D-glycero-D-galacto-2-nonulopyranosylonate]-(2,3)-O-(β-D-galactopyranosyl)-(1,4)-O-[(α-L-fucopyranosyl)-(1,3)]-O-(2-p-methoxybenza-mido-2-deoxy-β-D-glucopyranosyl)-(1,3)-O-β-D-galactopyranoside (Compound 35)

$R_f$=0.52 (3:1 i-PrOH:NH$_4$OAc), white solid, 46 mg, 90 percent.

$^1$H-NMR (300 MHz, δ in ppm relative to H$_2$O) 7.75 (d, J=9 Hz, 2H, aromatic), 7.05 (d, J=9 Hz, 2H), 5.11 (d, J=3 Hz, H-1-fuc, 1H), 4.95 (m), 4.52 (d, J=8 Hz, 1H), 4.25 (d, J=8 Hz, 1H), 4.19 (d, J=2 Hz, 1H), 4.15–3.39 (m), 3.82 (s, 3H, OCH$_3$), 2.75 (dd, J=3 Hz, J=11 Hz, H$_{eq}$-3 (sialic acid), 1H), 1.99 (s, 3H, NAc), 1.77 (dd, J=10 Hz, J=10 Hz, H$_{ax}$-3 (sialic acid), 1H), 1.17 (m, 5H, H-6-fuc, CH$_2$CH$_3$).

Ethyl [(5-acetamido-3,5-dideoxy-α-D-glycero-D-galacto-2-nonulopyranosylonate]-(2,3)-O-(β-D-galactopyranosyl)-(1,4)-O-[(α-L-fucopyranosyl)-(1,3)]-O-(2-p-tert-butylbenzamido-2-deoxy-β-D-glucopyranosyl)-(1,3)-O-β-D-galactopyranoside (Compound 36)

R$_f$=0.52 (3:1 i-PrOH:NH$_4$OAc), white solid, 46 mg, 90 percent.

$^1$H-NMR (300 MHz, δ in ppm relative to H$_2$O) 7.65 (d, J=9 Hz, 2H, aromatic), 7.58 (d, J=9 Hz, 2H), 5.19 (d, J=4 Hz, H-1 (fuc), 1H), 4.95 (m), 4.57 (d, J=8 Hz, 1H), 4.38 (d, J=8 Hz, 1H), 4.19 (d, J=2 Hz, 1H), 4.15–3.39 (m), 2.73 (dd, J=3 Hz, J=11 Hz, H$_{eq}$-3 (sialic acid), 1H), 2.05 (s, 3H, NAc), 1.77 (dd, J=10 Hz, J=10 Hz, H$_{ax}$-3 (sialic acid), 1H), 1.24 (s, 9H, '-Bu), 1.17 (m, 5H, H-6-fuc, CH$_2$CH$_3$).

(5-Acetamido-3,5-dideoxy-α-D-glycero-D-galacto-2-nonulopyranosylonate)-(2,3)-O-(β-D-galactopyranosyl)-(1,4)-O-[(α-L-fucopyranosyl)-(1,3)]-O-(2-benzamido-2-deoxy-β-D-glucopyranosyl)-(1,3)-O-β-D-galactopyranoside (Compound 37)

$^1$H-NMR, (300 MHz, δ in ppm relative to H$_2$O) 1.15 (3H, d, J=6.5 Hz, CH$_3$of Fuc), 1.81 (1H, t, J=10.4 Hz, H-3"a of NANA), 2.02 (3H, s, CH$_3$CONH), 2.78 (1H, dd, J=10.4 Hz, 3.2 Hz, H-3"e of NANA), 3.5–4.2 (m), 4.4–4.8 (m), 5.09, 5.16 (d, d, H-1 of FUC, α,β), 5.2 (d, J=3.4 Hz, H-1 α), 7.5–7.8 (5H, Aromatic).

Benzyl (5-acetamido-3,5-dideoxy-α-D-glycero-D-galacto-2-nonulopyranosylonate)-(2,3)-O-(β-D-galactopyranosyl)-(1,4)-O-[α-L-fucopyranosyl-(1,3)]-O-(2-benzamido-2-deoxy-β-D-glucopyranosyl)-(1,3)-O-β-D-galactopyranoside (Compound 38)

$^1$H NMR, (300 MHz, δ in ppm relative to H$_2$O) 1.08 (3H, d, J=6.4 Hz, CH$_3$ of Fuc), 1.76 (1H, t, J=10.4 Hz, H-3"a of NANA), 1.97 (3H, s, CH$_3$CONH), 2.7 (1H, dd, J=10.4 Hz, 3.2 Hz, H-3"e of NANA), 3.4–0.42 (m), 4.5 (1H, d, J=7.7 Hz), 4.6 (1H, d, J=8.0 Hz), 5.02 (d, J=3.8 Hz, H-1 of FUC), 7.1–7.8 (10H, Aromatic).

NMR data of Compounds 44–49

Ethyl (5-acetamido-3,5-dideoxy-α-D-glycero-D-galacto-2-nonulopyranosylonate)-(2,3)-O-(β-D-galactopyranosyl)-(1,4)-O-[(α-L-fucopyranosyl)-(1,3)]-O-[2-(3,4-dichlorobenzamido)-2-deoxy-β-D-glucopyranosyl]-(1,3)-O-β-D-galactopyranoside (Compound 44)

$^1$H-NMR (270 MHz, δ in ppm relative to H$_2$O) 7.82 (s, 1H), 7.56 (m, 2H), 5.99 (d, J=3.96 Hz, 1H), 4.47 (d, J=7.59 HZ, 1H), 4.25 (d, J=7.91 Hz, 1H), 4.15–3.22 (m), 2.66 (dd, J=12.54 Hz, J=3.96 Hz, 1H), 1.94 (s, 3H), 1.76 (t, J=12.54 Hz, 1H), 1.10 (m, 6H).

Ethyl [(5-acetamido-3,5-dideoxy-α-D-glycero-D-galacto-2-nonulopyranosylonate]-(2,3)-O-(β-D-galactopyranosyl)-(1,4)-O-[(α-L-fucopyranosyl)]-(1,3)-O-(2-furanamido-2-deoxy-β-D-glucopyranosyl)-(1,3)-O-β-D-galactopyranoside (Compound 45)

$^1$H-NMR (270 MHz, δ in ppm relative to H$_2$O) 7.59 (d, J=1.98 Hz, 1H), 7.10 (d, J=3.63 Hz, 1H), 6.54 (dd, J=3.36 Hz, J=1.98 Hz, 1H), 5.05 (d, J=4.29 Hz, 1H), 4.46 (d, J=7.59 Hz, 1H), 4.23 (d, J=7.92 Hz, 1H), 4.06 (d, J=2.97 Hz, 1H), 4.02–3.32 (m), 2.68 (dd, J=12.87 Hz, J=3.96 Hz, 1H), 1.95 (s, 3H), 1.77 (t, J=12.87 Hz, 1H), 1.08 (m, 6H).

Ethyl (5-acetamido-3,5-dideoxy-α-D-glycero-D-galacto-2-nonulopyranosylonate)-(2,3)-O-(β-D-galactopyranosyl)-(1,4)-O-[(α-L-fucopyranosyl)-(1,3)]-O-(2-thiophenamido-2-deoxy-β-D-glucopyranosyl)-(1,3)-O-β-D-galactopyranoside (Compound 46)

$^1$H-NMR (270 MHz, δ in ppm relative to H$_2$O) 7.63 (m, 2H), 7.10 (m, 1H), 5.06 (d, J=3.63 Hz, 1H), 4.46 (d, J=7.92 Hz, 1H), 4.23 (d, J=7.92 Hz, 1H), 4.06 (d, J=3.30 Hz, 1H), 4.04–3.30 (m), 2.67 (dd, J=12.21 Hz, J=3.96 Hz, 1H), 1.94 (s, 3H), 1.73 (t, J=12.21 Hz, 1H), 1.07 (m, 6H).

Ethyl [(5-acetamido-3,5-dideoxy-α-D-glycero-D-galacto-2-nonulopyranosylonate]-(2,3)-O-(β-D-galactopyranosyl)-(1,4)-O-[(α-L-fucopyranosyl)]-(1,3)-O-[2-(2-thiomethyl)nicotinamido-2-deoxy-β-D-glucopyranosyl]-(1,3)-O-β-D-galactopyranoside (Compound 48)

$^1$H-NMR (270 MHz, δ in ppm relative to H$_2$O) 7.62 (m, 2H), 7.06 (m, 1H), 5.04 (d, J=3.96 Hz, 1H), 4.43 (d, J=7.59 Hz, 1H), 4.23 (d, J=7.92 Hz, 1H), 4.10–3.20 (m), 2.68 (m, 1H), 2.14 (s, 3H), 2.09 (s, 3H), 1.70 (m, 1H), 1.05 (m, 6H).

Ethyl (5-acetamido-3,5-dideoxy-α-D-glycero-D-galacto-2-nonulopyranosylonate)-(2,3)-O-(β-D-galactopyranosyl)-(1,4)-O-[(α-L-fucopyranosyl)-(1,3)]-O-[2-(6-dodecyloxy-2-naphthamido)-2-deoxy-β-D-glucopyranosyl]-(1,3)-O-β-D-galactopyranoside (Compound 47)

$^1$H-NMR (270 MHZ, δ in ppm relative to CH$_3$OH) 8.32 (s, 1H), 7.90–7.78 (m, 3H), 7.26–7.16 (m, 2H), 5.17–5.13 (m, 1H), 4.48–4.40 (m, 1H), 4.22–3.32 (m), 2.88–2.82 (m, 1H), 2.01 (s, 3H), 1.85–1.19 (m), 0.91–0.85 (m, 3H).

Ethyl [(5-acetamido-3,5-dideoxy-α-D-glycero-D-galacto-2-nonulopyranosylonate]-(2,3)-O-(β-D-galactopyranosyl)-(1,4)-O-[(α-L-fucopyranosyl)]-(1,3)-O-(2-m-butyloxybenzamido-2-deoxy-β-D-glucopyranosyl)-(1,3)-O-β-D-galactopyranoside (Compound 49)

$^1$H-NMR (270 MHz, δ in ppm relative to H$_2$O) 7.39–7.22 (m, 3H), 7.13–7.09 (m, 1H), 5.03 (d, J=3.96 Hz, 1H), 4.46 (d, J=7.92 Hz, 1H), 4.23 (d, J=7.92 Hz, 1H), 4.07–3.34 (m), 2.68–2.64 (m, 1H), 1.93 (s, 3H), 1.74–1.62 (m, 3H), 1.30–1.44 (m, 2H), 1.07 (t, J=7.25 Hz, 3H), 1.06 (d, J=5.60 Hz, 3H), 0.84 (t, J=7.58 Hz, 3H).

Data for Compounds 50 and 51

Ethyl [(5-acetamido-3,5-dideoxy-α-D-glycero-D-galacto-2-nonulopyranosylonate]-(2,3)-O-(β-D-galactopyranosyl)-(1,4)-O-[(α-L-fucopyranosyl)]-(1,3)-O-(2-nicotinamido-2-deoxy-β-D-glucopyranosyl)-(1,3)-O-β-D-galactopyranoside (Compound 50)

R$_f$=0.22 (silica, iso-propanol/1M NH$_4$OAc); $^1$H NMR (300 MHz, D$_2$O): δ1.13 (d, 3H, J=6.6 Hz, CH$_3$ Fuc), 1.15 (t, 3H, J=6.7 Hz, OCH$_2$CH$_3$), 1.78 (t, 1H, J=11.9 Hz, H-3a NANA), 2.01 (s, 3H, COCH$_3$), 2.74 (dd, 1H, J=4.4, 11.9, H-3e NANA), 3.41–4.33 (multiple peaks, 34H), 4.31 (d, 1H, J=8.1 Hz, β-anomer Gal), 4.53 (d, 1H, J=8.0 Hz, β-anomer Gal), 5.10 (d, 1H, J=3.7 Hz, α-anomer Fuc), 7.56 (m, 1H, H-5 pyridyl), 8.16 (dd, 1H, J=1.3, 8.1 Hz, H-4 pyridyl), 8.68 (m, 1H, H-6 pyridyl), 8.85 (s, 1H, H-2 pyridyl).

Ethyl [Sodium (5-acetamido-3,5-dideoxy-α-D-glycero-D-galacto-2-nonulopyranosylonate)]-(2,3)-O-(β-D-galactopyranosyl)-(1,4)-O-[α-L-fucopyranosyl-(1,3)-O-]-(2-benzenesulfonamido-2-deoxy-β-D-glucopyranoside)-β-D-galactopyranoside (Compound 51)

R$_f$=0.28 (silica, 20 percent 1M NH$_4$OAc/isopropanol). $^1$H NMR (300 MHz, D$_2$O, ppm relative to H$_2$O): δ7.92 (d, J=7.4 Hz, 2H), 7.69 (d, J=7.2 Hz, 1H), 7.60 (t, J=7.2 Hz, 2H), 5.47 (d, J=4.0 Hz, 1H), 4.62 (d, J=8.1 Hz, 1H), 4.51 (d, J=7.6 Hz, 1H), 4.24 (d, J=8.0 Hz, 1H), 4.07 (dd, J=3.1, 9.6 Hz, 1H), 3.99 (d, J=3.1 Hz, 1H), 3.96=3.46 (m, 29H), 2.75 (dd, J=4.6, 12.5 Hz, 1H), 2.68 (dd, J=8.1, 8.1 Hz, 1H), 2.02 (s, 3H), 1.78 (t, J=12.1 Hz, 1H), 1.20 (t, 3H), 1.16 (d, J=6.5 Hz, 3H).

Cellular Binding Assays

A modified recombinant soluble E-selectin/HL-60 cell adhesion assay was developed to provide a simple and highly reproducible method with which to compare the E-selectin blocking potential of oligosaccharide analogs of sialyl Lewis X. In this assay, recombinant soluble E-selectin (rELAM) is bound to the plastic surface of a 96 well ELISA plate. Dilutions of SLe$^x$ analogue compounds to be assayed are added to the wells followed by HL-60 cells which bear the ligand for E-selectin. The cells are allowed to adhere to the E-selectin coated assay plate and the nonadherent cells are removed by washing the plate with an automated plate washer. Bound cells are quantitated by measuring the cellular enzyme myeloperoxidase. The concentration of assayed oligosaccharide required to achieve 50 percent inhibition of control adhesion is used to compare analogs for potency. The efficacy of using a similar bound recombinant soluble portion of ELAM-1 as a substrate for binding HL-60 and other cells that bind to cells containing the ELAM-1 (E-selectin) receptor has been demonstrated by Lobb et al., *J. Immunol.*, 147:124–129 (1991).

MATERIALS AND METHODS:
Materials

ELISA plate, Immulon 2 (Dynatec Laboratories) (Fisher 14-245-61)

0.2 m filter units (Nalgene #150-0020)

rELAM (recombinant modified ELAM-1) affinity purified, prepared as follows below. Each batch of rELAM was tested functionally to determine the appropriate concentration for use in the assay. A batch was titrated over a range of 1–5 μg/mL using inhibition by Compound Z (described hereinafter) as the standard. Small aliquots were then prepared, quick frozen in a dry-ice acetone bath and stored at −70° C. Each aliquot was opened only one time and then discarded or saved for use in other types of assays.

The soluble form of E-selectin (rELAM or sol-E-selectin) used here was engineered by deleting the transmembrane domain from the cDNA. This recombinant cDNA was cloned into a mammalian expression vector pCDNA1 [a derivative of pCDM8; Seed, Nature, 329:840 (1987)] that contains the chimeric cytomegalovirus/human immunodeficiency virus promoter. When introduced into the adenovirus-transformed human kidney cell line 293, expression of the CMV promoter is efficiently activated by the E1 gene products by a mechanism that has not been fully delineated. The pCDNA1-sol-E-selectin construction was introduced, via calcium phosphate-mediated gene transfer, into 293 cells and a stable cell line expressing high levels of sol-E-selectin was generated. The sol-E-selectin produced by these cells was purified by immunoaffinity chromatograph on an anti-E-selectin monoclonal antibody Protein-A Sepharose column.

More specifically, the adenovirus transformed human kidney cell line 293 was obtained from the ATCC (CRL-1573). 293 Cells were grown as adherent cultures in DMEM, obtained from Whittaker Bioproducts (Walkersville, Md.), supplemented with 10 percent fetal bovine serum (FBS), obtained from JRH Biochemical (Lenexa, Kans.).

The plasmid pCDNA1, a derivative of pCDM8 [Seed, *Nature*, 339:840 (1987)], was obtained from Invitrogen (San Diego, Calif.). The plasmid pBluescript II was obtained from Stratagene (San Diego, Calif.). The plasmid pSV2-neo [Southern et al., *J. Mol. Appl. Gen.*, 1:327 (1982)] contains the *E. coli* gene encoding the aminoglycoside 3'-phosphotransferase gene. When pSV2neo is introduced into mammalian cells, the transfected cells exhibit resistance to the antibiotic G418.

A 1.67 Kbp DNA fragment encoding a truncated structural gene for E-selectin was isolated by polymerase chain reaction (PCR) amplification of cDNA derived from messenger RNA that was isolated from IL-1-activated human endothelial cells. The 5'-amplimer inserted a unique Cla 1 restriction site 28 nucleotides upstream from the initiation codon of the E-selectin structural gene. The 3'-amplimer inserted the termination codon TGA after amino acid number 527 of the mature E-selectin, followed by a unique Xhol restriction site. The carboxy-terminus of sol-E-selectin is located at the carboxy terminus of the sixth consensus repeat element, thereby deleting the transmembrane domain. The 1.67 Kbp PCR fragment was codigested with Cla 1 and Xho 1 restriction endonucleases and sub-cloned into the Cla 1 and Xho restriction sites of the cloning vector pBluescript II, providing vector pBSII-sol-E-selectin. Soluble-E-selectin is 527 amino acids in length and contains 11 potential N-glycosylation sites.

A 1.67 Kbp DNA fragment containing the sol-E-selectin cDNA was isolated from pBSII-sol-E-selectin and sub-cloned into the Eco RV and Xho 1 sites of the expression vector pCDNA1, thereby providing vector pCDNA1-sol-E-selectin.

pCDNA1-sol-E-selectin was cotransfected with pSV2-neo, via the calcium phosphate technique [Kriegler, *Gene Transfer and Expression: A Laboratory Manual*, W. H. Freeman, New York, N.Y. (1991)] into 293 cells. Forty-eight hours post-transfection, the transfected 293 cells were trypsinized and plated into DMEM, 10 percent FBS, and 600 mg/ml of G418 (Geneticin, Sigma). The selection medium was changed every three days until a stable G418resistant population was established.

Single clones of G418-resistant cells were isolated by cloning cylinders. Isolated clones were screened for the synthesis of sol-E-selectin by enzyme-linked immunosorbent assay (ELISA) utilizing the anti-E-selectin monoclonal antibody designated CY1787 as the primary antibody. Positive clones were plated at $10^6$ cells/100 mm dish. They were metabolically labeled 24 hours later with [$^{35}$S]-methionine for five hours. Labeled sol-E-selectin was immunoprecipitated from the medium with the anti-E-selectin monoclonal antibody and electrophoresed through a 10 percent PAGE gel, the gel dried and subjected to autoradiograph. Clone 293#3 was selected as the stable cell line that produced the greatest amount of the 110-Kd sol-E-selectin protein/cell.

A 10-chambered Nuc Cell Factory (6250 cm$^2$ total surface area, Nunc) was seeded with 2.78×10$^8$ cells (clone 293#3) in 850 ml in DMEM supplemented with five percent FBS and incubated at 37° C. for 72 hours. The medium was harvested and replaced with 850 ml of DMEM five percent FBS. After the cell factory was incubated at 37° C. for 48 hours, the medium was harvested a second time and replaced with 850 ml DMEM five percent FBS. After the cell factory was incubated at 37° C. for 48 hours, the medium was harvested a third (and final) time.

After each harvest, 0.02 percent sodium azide was added to the medium. The medium was clarified by centrifugation (5000× g), passed through a 0.2 mm filter and stored at 4° C. until further purification.

Monoclonal antibody CY1787 was conjugated to protein-A Sepharose essentially as described by Schneider et al., *J. Biol. Chem.*, 257:10766 (1982). Briefly, 28 mg of monoclonal CY1787 (5 mg/ml) in PBS was mixed with 5 ml of protein-A Sepharose for 30 minutes at room temperature. The beads were then washed four times by centrifugation with 25 ml of 0.2M borate buffer, pH 8.2, followed by two washes with 10 ml of 0.2M triethanolamine, pH 8.2. The resin was then suspended in 40 ml of 0.2M triethanolamine buffer, pH 8.2, containing 0.02M dimethylpimelimidate. After reacting for 45 minutes at room temperature on a rotator, the resin was washed twice with 0.02M ethanolamine, pH 8.2, followed with three washes with 10 ml of 0.2M borate buffer, pH 8.2. Unbound antibody was removed by elution with 0.1M sodium acetate buffer, pH 4.5. Of the antibody applied, 89 percent was conjugated to the protein-A Sepharose.

Tissue culture supernatant (2550 ml) was passed through a 0.7 cm×1.5 cm pre-column of protein-A Sepharose connected in series to a 1.5 cm×3 cm affinity column of CY1787-protein-A Sepharose at a flow rate of 20 ml/hr. The columns were then disconnected and the CY1787-containing affinity column was washed with 20 mM Tris buffer, pH 7.5, containing 150 mM NaCl and 2 mM $CaCl_2$ until the absorbance at 280 nm of the eluate approached zero. Bound E-selectin was eluted with 0.1M sodium acetate buffer, pH 3.5, containing 1 mM $CaCl_2$ using gravity flow. Fractions (1 mL) were collected into 300 ml of 2M Tris, pH 10. Protein-containing fractions were pooled and dialyzed against DPBS. Following concentration of an Amicon Centriprep 30 until the protein concentration was approximately 1 mg/ml, the purified E-selectin was aliquoted and stored at −80° C. Purity was greater than 90 percent by SDS-PAGE. A total of 10 mg of E-selectin was purified from 2550 ml of cell culture medium.

Dulbecco's PBS (DPBS) (Whittaker, 17-513B)

HL-60 (ATCC, CCL 240) A large batch of HL-60 cells was grown up, tested for function in the assay and verified mycoplasma free. The cells were frozen at −180° C. in 10 percent DMSO, 10 percent Fetal Calf Serum, 80 percent RPMI 1640 (Whittaker) at $15×10^6$ cells per vial in 2 ml cryovials. Freezing was performed using a controlled rate freezer.

Compound Z Standard $SLe^x$ pentasaccharide-OEt: NeuAcα2→3Galβ1→4[Fucα1→3]GlcNAcβ1→3GalβOEt The Compound Z Standard was prepared as a 10 mM solution in DPBS. The solution was stored at −20° C.

Neutrophil wash buffer (NWB):

| 10X HBSS (Gibco, 310–4065) | 20 mL |
| 1M HEPES ( Gibco, 380–5630) | 2 mL |
| Super Q $H_2O$ | 178 mL |
| D-Glucose (Sigma, G 7021) | 0.4 g |
| | 200 mL |

Made fresh daily or stored sterilized solution at 4° C. pH to 7.2–7.4, filter sterilized (0.2μ).

100 mM $CaCl_2$ stock:

| Calcium chloride, anhydrous (Baker, 1308) | 1.11 g |
| Super Q $H_2O$ | 100 mL |
| Filter sterilized (0.2 m) | 100 mL |

Neutrophil wash buffer +1 mM $CaCl_2$+0.1 percent BSA (NWB/Ca/BSA):

| Bovine serum albumin (Sigma, A-6918) | 10 g |
| 100 mM $CaCl_2$ stock | 100 mL |
| NWB to | 1000 mL | pH to 7.2 to 7.4. Filter sterilized (0.2μ), store stock at 4° C.

Blocking Buffer:

| DPBS (Whittaker, 17-513B | 100 mL |
| Bovine Serum Albumin (Sigma, A-6918) | 1 g |
| | 100 mL | pH to 7.2 to 7.4. Filter sterilized (0.2μ), stock stored at 4° C.

Citric Acid Solution, 0.1M:

| Citric acid, anhydrous, free acid (Sigma, C-0759) | 10.5 g |
| Super Q $H_2O$ | bring to 500 mL |

Prepare in volumetric or graduated cylinder. Stored at room temperature.

Sodium Phosphate Solution, 0.2M:
Sodium phosphate, dibasic, anhydrous ($Na_2HPO_4$)

| Sodium phosphate, dibasic, anhydrous ($Na_2HPO_4$) (Sigma, S-0876) | 14.2 g |
| Super Q $H_2O$ | bring to 500 mL |

Prepared in volumetric or graduated cylinder. Stored at room temperature.

| Citrate/Phosphate buffer: | |
| Citric acid solution (0.1M) | 24.3 mL |
| Sodium phosphate solution (0.2M) | 25.7 mL |
| Super Q $H_2O$ | 50 mL |
| | 100 mL |

Stored at room temperature.

Cell Lysis Buffer:

| Nonidet P 40 (NP-40) (Sigma, N-6507 | 0.1 g |
| 0.1M Citrate | 24.3 mL |
| 0.2M Sodium phosphate, dibasic | 25.7 mL |
| Super Q $H_2O$ | 50.0 mL |
| | 100.0 mL |

Stored at room temperature.

| OPDA (o-phenylenediamine): | |
| Citrate-phosphate buffer | 10 mL |
| o-Phenylenediamine dihydrochloride (Sigma, P 8287) | 10 mg |
| $H_2O_2$ (Sigma, H 1009) | 10 μL |
| | 10 mL |

Made immediately before use. Hydrogen peroxide was stored in the dark at 10° C.

$H_2SO_4$ Stop buffer, 4N

| Sulfuric acid, 18M (Fisher, A300s-212) | 111 mL |
| Super Q $H_2O$ | to 500 mL |

Method

1. The rELAM (sol-E-selectin) was diluted to the appropriate concentration for the current batch. For these assays, rELAM was used at 2.5 μg/ml in DPBS. Using a multichannel pipette, 50 μl per well were added to the following wells of one ELISA plate: E1-E6, F1-F6, and G1-G6. DPBS (50 μl)

was added to wells H1, H2, and H3 for use as controls. This plate is referred to as the pretest plate.

One additional assay plate was coated for every three unknown samples to be assayed. Again, using a multichannel pipette, 50 μL of the diluted rELAM was added to the following wells of the plates: B1-B12, C1-C12, D1-D12, E1-E12, F1-F12, G1-G12. DPBS (50 μl) to wells H1, H2, and H3 for use as controls. These plates are known as the sample plates. These plates were covered with foil and incubated three hours at room temperature.

2. The plates were washed three times with 200 μL blocking buffer. The wells were refilled with 200 μL blocking buffer, covered with foil and incubated at room temperature for one hour.

3. Three vials of frozen HL-60 cells were thawed for every two sample plates prepared. The vials were quick-thawed in a 37° C. water bath. The cells were pipetted into a 15 mL centrifuge tube containing 10 ml of ice cold NWB 1 percent BSA. The cells were centrifuged for seven minutes at 1200 rpm in a centrifuge, and washed two more times in NWB/BSA. The cells were counted using a hemocytometer and resuspended to 10$^7$/mL in NWB +1 percent BSA +1 mM CaCl$_2$.

4. While the cells were being washed, the standard and assay compound solutions were prepared. The oligosaccharide compound to be assayed were weighed into 1.5 mL eppendorf tubes and enough DPBS was added to make each sample a 10 mM solution according to its molecular weight. A 6 μL aliquot of each sample was removed and 2 μL were dotted on each square of a of a pH test strip. If the sample was not pH 7-7.4, the pH value was adjusted to that range or the compound was not assayed. The assay requires 180 μL of a 10 mM solution of each compound solution to be used and 180 μL of a 10 mM solution of the standard Compound Z for each plate to be run including the test plate.

5. The blocked ELISA plates were inverted and flicked, and blotted by tapping vigorously on paper towels to remove all liquid from the wells. To each well were then added 40 μL of NWB +1 percent BSA +1 mM Ca$^{+2}$ using a multi-channel pipette.

6. All of the liquid was removed from wells E6 and G6 of the pretest plate. An aliquot of 40 μL of 10 mM stock of Compound Z was added to each of the empty wells, as well as to wells E5 and G5. The solution in well E5 was mixed by pipetting up and down 10 times with a p 200 pipetteman set at 40 μL. A 40 μl aliquot of solution was removed from the well and diluted serially across the plate in well E4 then E3 and then E2, each time mixing 10 times. A 40 μl aliquot was removed and discarded from the last well. This procedure was repeated for rows G4 to G2.

7. HL-60 cells (2×10$^5$) were added to each well (except H1) in 20 μl using a multichannel pipette. The plate was placed on a plate shaker for five seconds, and let stand 15 minutes at room temperature.

8. The plate was washed using a Molecular Devices Microplate washer adjusted for slow liquid delivery and set on 3 washes per well, with NWB +1 percent BSA+1 mM CaCl$_2$ as the wash solution.

Cell Lysis Buffer (50 μL per well) was added and the plate placed on plate shaker for five minutes at room temperature.

9. A 50 μL aliquot per well of OPDA solution was added, and the plate was placed on the plate shaker for ten minutes at room temperature.

11. The color-forming reaction was stopped by the addition of 40 μL per well of H$_2$SO$_4$ Stop buffer, and the optical density (O.D.) for the wells of the plate was read at 492 nm, subtracting well Hi as the blank.

12. The negative control was determined by taking the mean of the O.D. values for wells H2 and H3. This is the "no-E-selectin negative binding control". The "positive binding control" was calculated for the standard curve as the mean of wells E1, F1, F2, F3, F4, F5, F6, and G1. If the "no-E-selectin negative binding control" was greater than 10 percent of the mean "positive binding control", the assay was not continued. If that value was less than or equal to 10 percent of the mean "positive binding control", sample duplicates (E6, G6), (E5, G5), (E4, G4), (E3, G3) and (E2, G2) were averaged. Each duplicate average was divided by the mean "positive binding control" value to give percentage of positive binding for each concentration of assayed compound. The "positive binding control" percent was plotted vs log concentration of inhibitor. The 50 percent inhibition point was determined from the graph. This point should lie between 0.5 and 1.5 mM, and if not, the assay did not continue.

13. If the pretest plate standard curve was within the acceptable limits, the remainder of the assay proceeded. The standard Compound Z was diluted on each sample plate as in step 6. Assayed compounds were diluted similarly. Assay SLe$^x$ analogue compounds were placed on the plate according to the following template:

| Conc. | | Assay #1 | Assay #2 | Assay #3 |
|---|---|---|---|---|
| 6.6 mM or | Dil. 1 | B6, D6 | B7, D7 | E7, G7 |
| 3.3 mM | Dil. 2 | B5, D5 | B8, D8 | E8, G8 |
| 1.65 mM | Dil. 3 | B4, D4 | B9, D9 | E9, G9 |
| 0.82 mM | Dil. 4 | B3, D3 | B10, D10 | E10, G10 |
| 0.412 mM | Dil. 5 | B2, D2 | B11, D11 | E11, G11 |

14. When all assay samples were diluted on the plate, HL-60 cells were added as in step 7 above and the procedure followed through step 11 as above.

15. The mean "positive binding control" was calculated for assay #1 from wells B2, C1-6 and D2; for assay #2 from wells B12, C7-12 and D12; and for assay #3 from wells E12, F7-12 and G12. The percent of positive binding for each dilution of each assay was graphed and the 50 percent inhibition point determined from the graph. Activity for each assayed SLe$^x$ analogue compound was recorded as a ratio of the 50 percent binding value for the standard Compound Z divided by the 50 percent binding value for the assayed SLe$^x$ sample. The value for SLe$^x$ itself was similarly determined.

Ratios for SLe$^x$ itself and several contemplated SLe$^x$ analogue compounds are provided in Table 4, below.

TABLE 4

E-Selection Cell Adhesion Assay

| Compound | Compound No. | Ratio $\left( \dfrac{\text{Compound Z IC}_{50}}{\text{Compound IC}_{50}} \right)$ |
|---|---|---|
| [structure] | SLe$^x$ | 0.76 |
| [structure] | 17 | 5.0 |
| [structure] | 30 | 3.2 |
| [structure] | 31 | 4.3 |

TABLE 4-continued

E-Selection Cell Adhesion Assay

| Compound | Compound No. | Ratio $\left(\dfrac{\text{Compound Z IC}_{50}}{\text{Compound IC}_{50}}\right)$ |
|---|---|---|
| [structure] | 32 | 0.53 |
| [structure] | 33 | 9.3<br>10.0<br>11.2 |
| [structure] | 34 | 0.2 |
| [structure] | 35 | 4.7 |

TABLE 4-continued
E-Selection Cell Adhesion Assay
| Compound | Compound No. | Ratio $\left(\dfrac{\text{Compound Z IC}_{50}}{\text{Compound IC}_{50}}\right)$ |
|---|---|---|
| 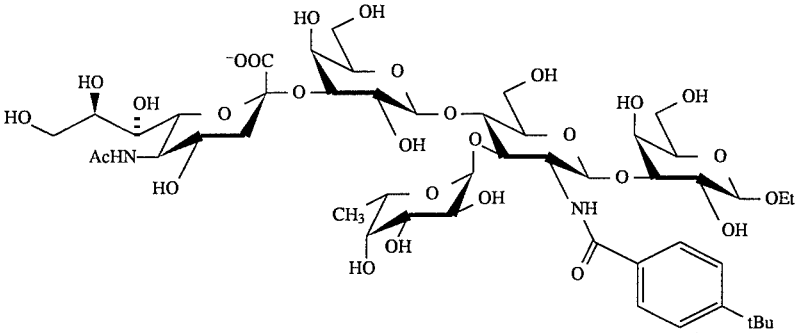 | 36 | 5.7<br>8.9 |
| 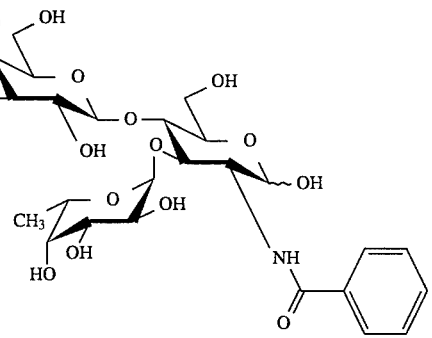 | 37 | 4.0 |
| 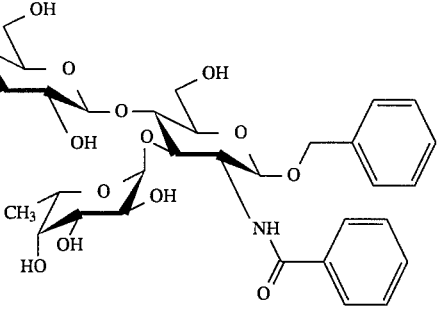 | 38 | 10.0 |
| 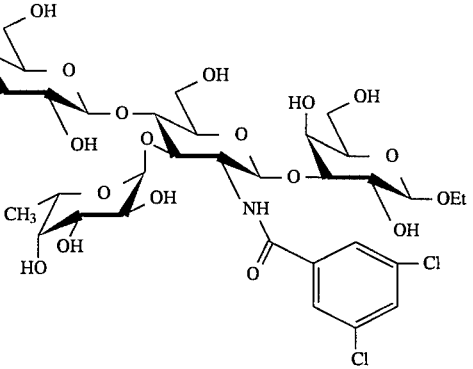 | 43 | 2.3 |

TABLE 4-continued

E-Selection Cell Adhesion Assay

| Compound | Compound No. | Ratio $\left(\dfrac{\text{Compound Z IC}_{50}}{\text{Compound IC}_{50}}\right)$ |
|---|---|---|
| (structure) | 45 | 6.0 |
| (structure) | 46 | 6.0 |
| (structure) | 48 | 0.3 |
| (structure) | 50 | 3.0 |

TABLE 4-continued

E-Selection Cell Adhesion Assay

| Compound | Compound No. | Ratio $\left(\dfrac{\text{Compound Z IC}_{50}}{\text{Compound IC}_{50}}\right)$ |
|---|---|---|
| | 51 | 3.0 |

The foregoing is intended as illustrative of the present invention but not limiting. Numerous variations and modifications may be effected without departing from the true spirit and scope of the novel concepts of the invention.

We claim:

1. A compound of the formula

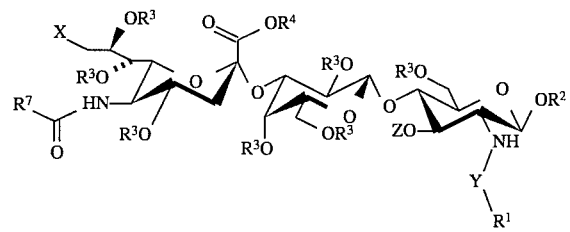

wherein

Z is hydrogen, $C_1$–$C_6$ acyl or

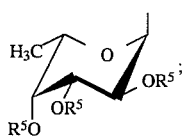

Y is selected from the group consisting of C(O), $SO_2$, HNC(O), OC(O) and SC(O);

$R^1$ is selected from the group consisting of an aryl, a substituted aryl and a phenyl $C_1$–$C_3$ alkylene group, wherein said aryl substituent is selected from the group consisting of a halo, trifluoromethyl, nitro, $C_1$–$C_{18}$ alkyl, $C_1$–$C_{18}$ alkoxy, amino mono-$C_1$–$C_{18}$ alkylamino, di-$C_1$–$C_{18}$ alkylamino, benzylamino, $C_1$–$C_{18}$ alkylbenzylamino, $C_1$–$C_{18}$ thioalkyl and $C_1$–$C_{18}$ alkyl carboxamido groups, or $R^1Y$ is allyloxycarbonyl or chloroacetyl;

$R^2$ is selected from the group consisting of monosaccharide, disaccharide, hydrogen, $C_1$–$C_{18}$ straight chain, branched chain or cyclic hydrocarbyl, $C_1$–$C_6$ alkyl $C_1$–$C_5$ alkylene ω-carboxylate, ω-trisubstituted silyl $C_2$–$C_4$ alkylene wherein said ω-trisubstituted silyl is a silyl group having three substituents independently selected from the group consisting of $C_1$–$C_4$ alkyl and phenyl, or $OR^2$ together form a $C_1$–$C_{18}$ straight chain, branched chain or cyclic hydrocarbyl carbamate;

$R^3$ is hydrogen or $C_1$–$C_6$ acyl;

$R^4$ is hydrogen, $C_1$–$C_6$ alkyl or benzyl;

$R^5$ is selected from the group consisting of hydrogen, benzyl, methoxybenzyl, dimethoxybenzyl and $C_1$–$C_6$ acyl;

$R^7$ is methyl or hydroxymethyl; and

X is selected from the group consisting of $C_1$–$C_6$ acyloxy, $C_2$–$C_6$ hydroxylacyloxy, hydroxy, halo and azido.

2. The compound according to claim 1 wherein $R^2$ is monosaccharide.

3. The compound according to claim 1 wherein X is hydroxy.

4. The compound according to claim 1 wherein Z is hydrogen.

5. The compound according to claim 1 wherein Z is

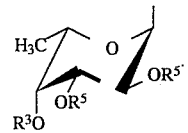

6. A compound of the formula

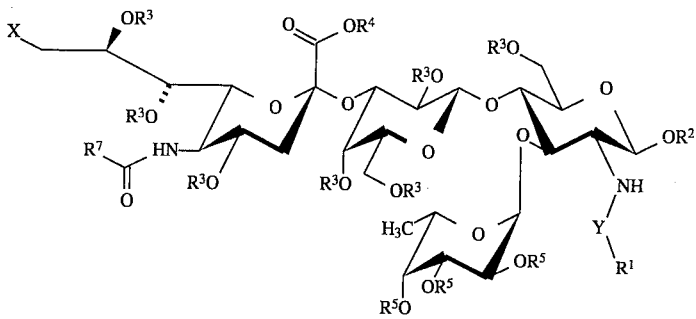

Y is selected from the group consisting of C(O), SO$_2$, HNC(O), OC(O) and SO(O);

R$^1$ is selected from the group consisting of an aryl, a substituted aryl and a phenyl C$_1$–C$_3$ alkylene group, wherein said aryl substituent is selected from the group consisting of a halo, trifluoromethyl, nitro, C$_1$–C$_{12}$ alkyl, C$_1$–C$_{12}$ alkoxy, amino, mono-C$_1$–C$_{12}$ alkylamino, di-C$_1$–C$_{12}$ alkylamino, benzylamino, C$_1$–C$_{12}$ alkylbenzylamino, C$_1$–C$_{12}$ thioalkyl and C$_1$—C$_{12}$ alkyl carboxamido groups, or R$^2$ is selected from the group consisting of monosaccharide, disaccharide, hydrogen, C$_1$–C$_{18}$ straight chain, branched chain or cyclic hydrocarbyl, C$_1$–C$_6$ alkyl C$_1$–C$_5$ alkylene ω-carboxylate, ω-trisubstituted silyl C$_2$–C$_4$ alkylene wherein said ω-trisubstituted silyl is a silyl group having three substituents independently selected from the group consisting of C$_1$–C$_4$ alkyl and phenyl, or OR$^2$ together form a C$_1$–C$_{18}$ straight chain, branched chain or cyclic hydrocarbyl carbamate;

R$^3$ is hydrogen or C$_1$–C$_6$ acyl;

R$^4$ is hydrogen, C$_1$–C$_6$ alkyl or benzyl;

R$^5$ is selected from the group consisting of hydrogen, benzyl, methoxybenzyl dimethoxybenzyl and C$_1$–C$_6$ acyl;

R$^7$ is methyl or hydroxymethyl; and

X is selected from the group consisting of C$_1$–C$_6$ acyloxy, C$_2$–C$_6$ hydroxylacyloxy hydroxy, halo and azido.

7. The compound according to claim 6 wherein X is hydroxyl, R$^2$ selected from the group consisting of hydrogen, C$_1$–C$_{18}$ straight chain, branched chain or cyclic hydrocarbyl, C$_1$–C$_6$ alkyl C$_1$–C$_5$ alkylene ω-carboxylate, and ω-trisubstituted silyl C$_2$–C$_4$ alkylene wherein said ω-trisubstituted silyl is a silyl group having three substituents independently selected from the group consisting of C$_1$–C$_4$ alkyl and phenyl, and R$^7$ is methyl.

8. The compound according to claim 7 wherein R$^3$=R$^4$=R$^5$=hydrogen.

9. The compound according to claim 8 wherein R$^1$ is phenyl.

10. The compound according to claim 6 wherein R$^2$ is a monosaccharide.

11. A compound of the formula

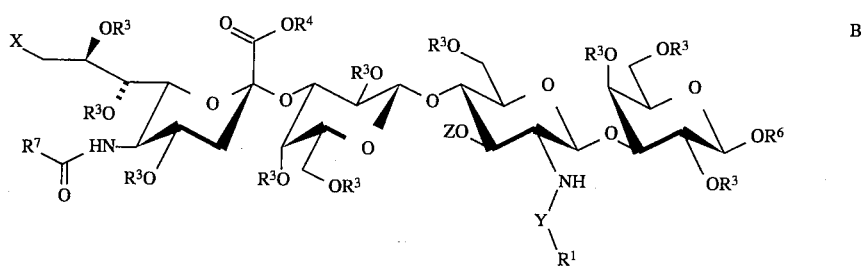

B wherein

Z is hydrogen, C$_1$–C$_6$ acyl or

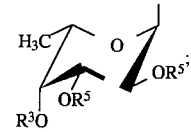

Y is selected from the group consisting of C(O), SO$_2$, HNC(O), OC(O) and SC(O);

R$^1$ is selected from the group consisting of an aryl, a substituted aryl and a phenyl C$_1$–C$_3$ alkylene group, wherein said aryl substituent is selected from the group consisting of a halo, trifluoromethyl, nitro, C$_1$–C$_{18}$ alkyl, C$_1$–C$_{18}$ alkoxy, amino, mono-C$_1$–C$_{18}$ alkylamino, di-C$_1$–C$_{18}$ alkylamino, benzylamino, C$_1$–C$_{18}$ alkylbenzylamino, C$_1$–C$_{18}$ thioalkyl and C$_1$–C$_{18}$ alkyl carboxamido groups, or R$^1$Y is allyloxycaxbonyl or chloroacetyl;

R$^3$ is hydrogen or C$_1$–C$_6$ acyl;

R$^4$ is hydrogen C$_1$–C$_6$ alkyl or benzyl;

R$^5$ is selected from the group consisting of hydrogen, benzyl, methoxybenzyl, dimethoxybenzyl and C$_1$–C$_6$ acyl;

R$^6$ is selected from the group consisting of hydrogen, C$_1$–C$_{18}$ straight chain, branched chain or cyclic hydrocarbyl, C$_1$–C$_6$ alkyl C$_1$–C$_5$ alkylene ω-carboxylate and ω-trisubstituted silyl C$_2$–C$_4$ alkylene wherein said ω-trisubstituted silyl is a silyl group having three substituents independently selected from the group consisting of C$_1$–C$_4$ alkyl and phenyl, or OR$^6$ together form a C$_1$–C$_{18}$ straight chain, branched chain or cyclic hydrocarbyl carbamate;

R$^7$ is methyl or hydroxymethyl; and

X is selected from the group consisting of $C_1$–$C_6$ acyloxy, $C_2$–$C_6$ hydroxylacyloxy, hydroxy, halo and azido.

12. The compound according to claim 11 wherein Y is carbonyl.

13. The compound according to claim 12 wherein Z is

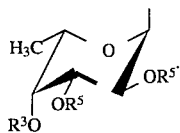

14. A compound of the formula

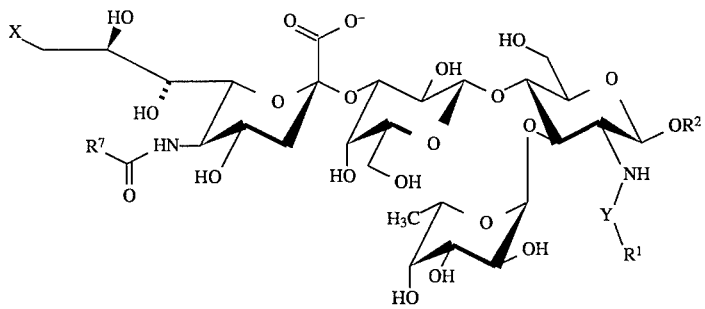

Y is selected from the group consisting of C(O), $SO_2$, HNC(O), OC(O) and SO(O);

$R^1$ is selected from the group consisting of an aryl, a substituted aryl and a phenyl $C_1$–$C_3$ alkylene group, said aryl substituent is selected from the group consisting of a halo, trifluoromethyl, nitro, $C_1$–$C_{18}$ alkyl, $C_1$–$C_{18}$ alkoxy, amino, mono-$C_1$–$C_{18}$ alkylamino, di-$C_1$–$C_{18}$ alkylamino, benzylamino, $C_1$–$C_{18}$ alkylbenzylamino, $C_1$–$C_{18}$ thioalkyl and $C_1$–$C_{18}$ alkyl carboxamido groups;

$R^2$ is selected from the group consisting of monosaccharide, disaccharide, hydrogen, $C_1$–$C_{18}$ straight chain, branched chain or cyclic hydrocarbyl, $C_1$–$C_6$ alkyl $C_1$–$C_5$ alkylene ω-carboxylate, ω-trisubstituted silyl $C_2$–$C_4$ alkylene wherein said ω-trisubstituted silyl is a silyl group having three substituents independently selected from the group consisting of $C_1$–$C_4$ alkyl and phenyl, or $OR^2$ together form a $C_1$–$C_{18}$ straight chain branched chain or cyclic hydrocarbyl carbamate;

$R^7$ is methyl or hydroxymethyl; and

X is selected from the group consisting of $C_1$–$C_6$ acyloxy $C_1$–$C_6$ hydroxylacyloxy hydroxy, halo and azido.

15. The compound according to claim 14 wherein X is hydroxyl.

16. The compound according to claim 14 wherein $R^2$ is selected from the group consisting of hydrogen, $C_1$–$C_{18}$ straight chain, branched chain or cyclic hydrocarbyl, $C_1$–$C_6$ alkyl $C_1$–$C_5$ alkylene ω-carboxylate, and ω-trisubstituted silyl $C_2$–$C_4$ alkylene wherein said ω-trisubstituted silyl is a silyl group having three substituents independently selected from the group consisting of $C_1$–$C_4$ alkyl and phenyl.

17. The compound according to claim 16 wherein Y is carbonyl.

18. The compound according to claim 17 having the formula

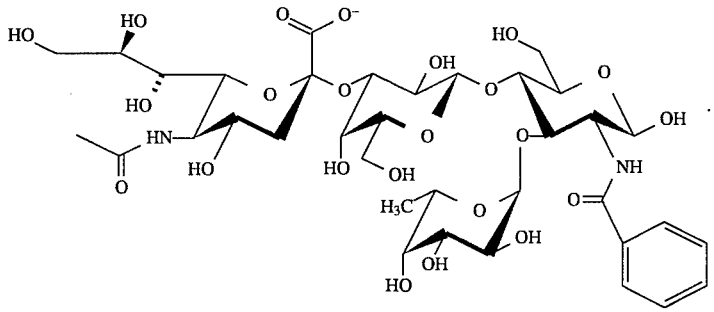

19. The compound according to claim 17 having the formula

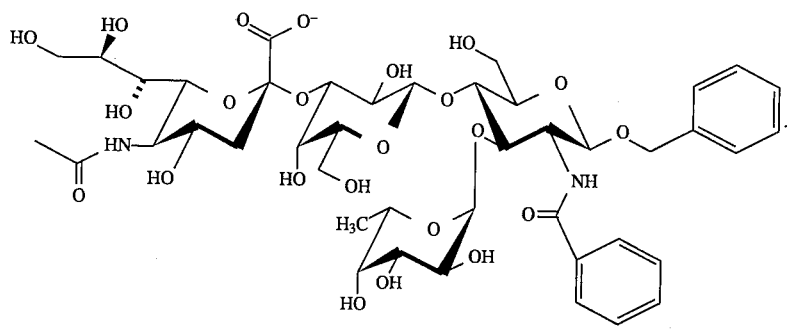
20. The compound according to claim 14 wherein $R^2$ is a monosaccharide.
21. The compound according to claim 20 wherein Y is carbonyl.
22. The compound according to claim 21 having the formula
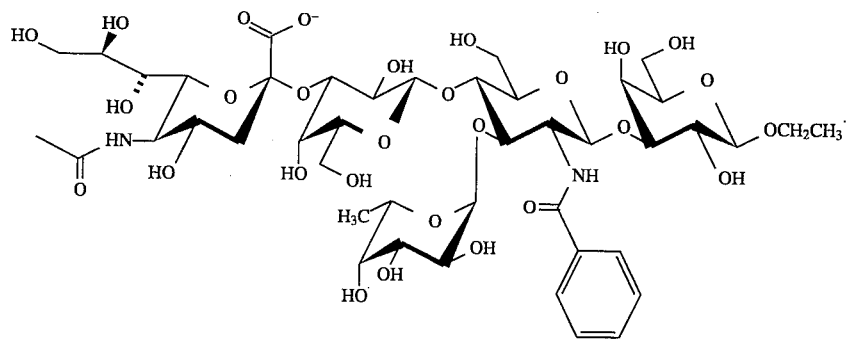
23. The compound according to claim 21 having the formula
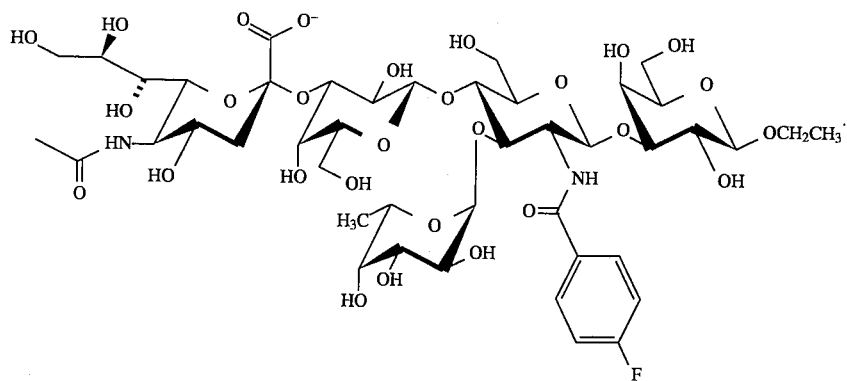
24. The compound according to claim 21 having the formula

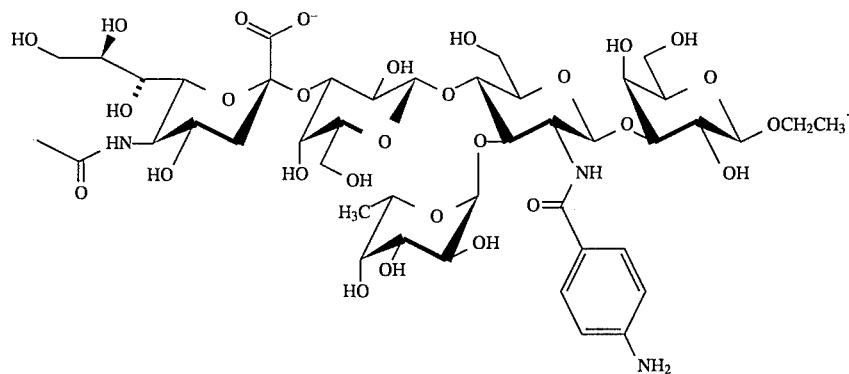
25. The compound according to claim 21 having the formula
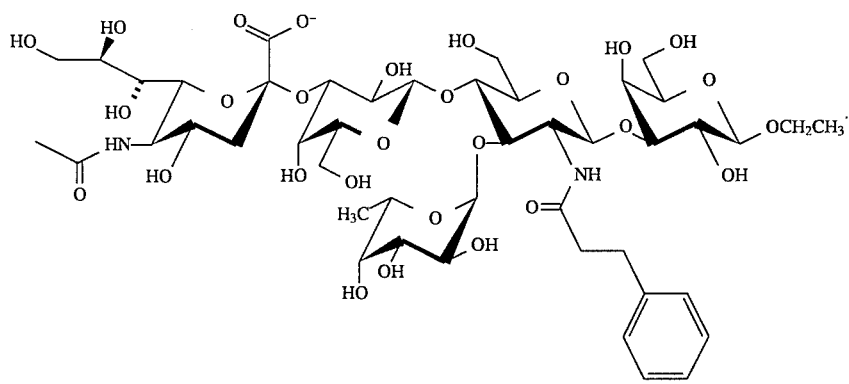
26. The compound according to claim 21 having the formula
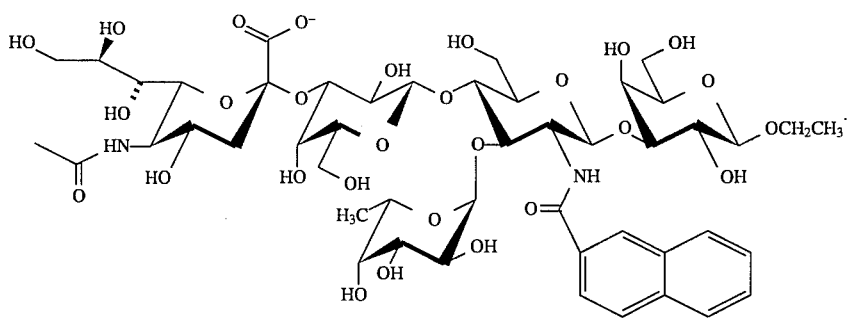
27. The compound according to claim 21 having the formula

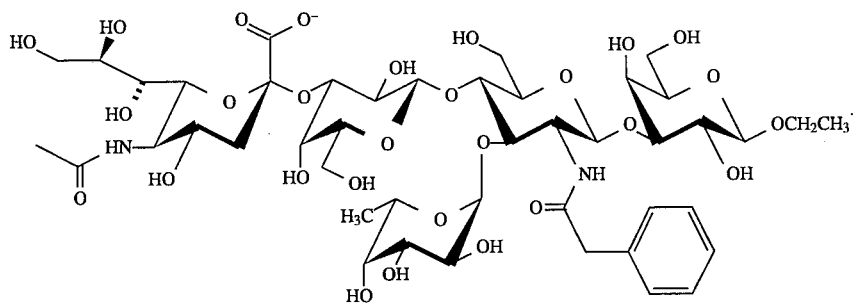
28. The compound according to claim 21 having the formula
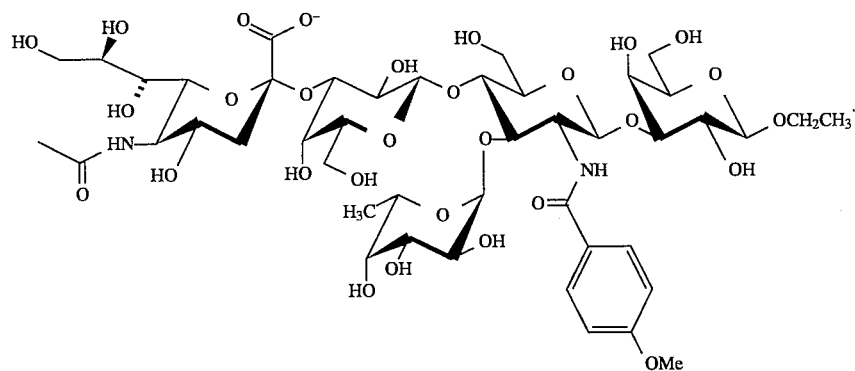
29. The compound according to claim 21 having the formula
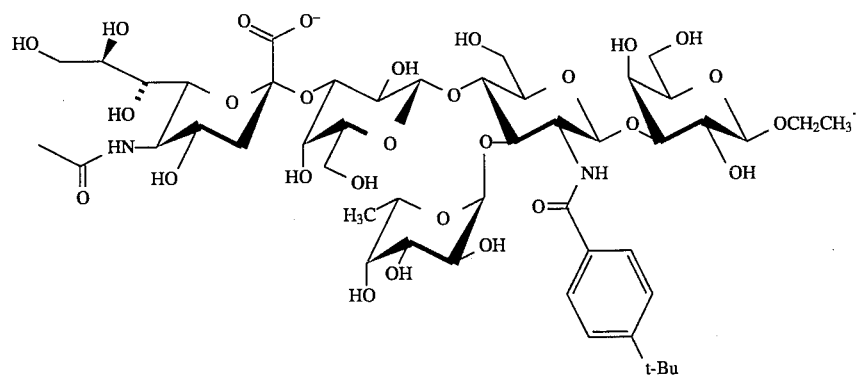
30. The compound according to claim 21 having the formula

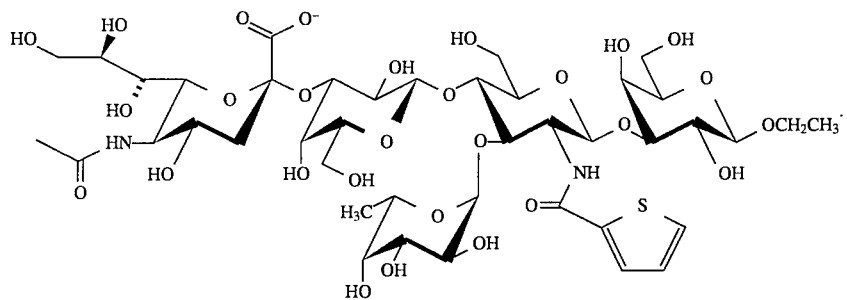
31. The compound according to claim 21 having the formula
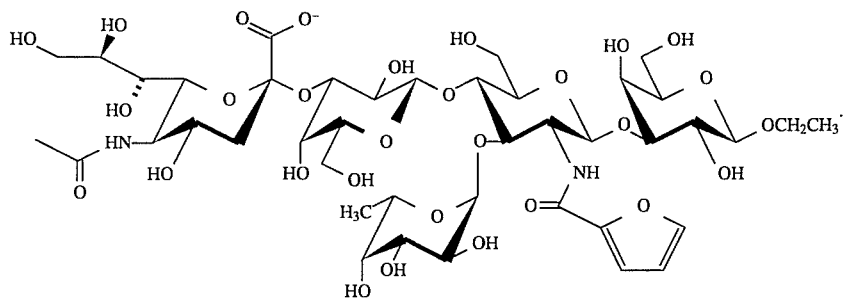
32. The compound according to claim 21 having the formula
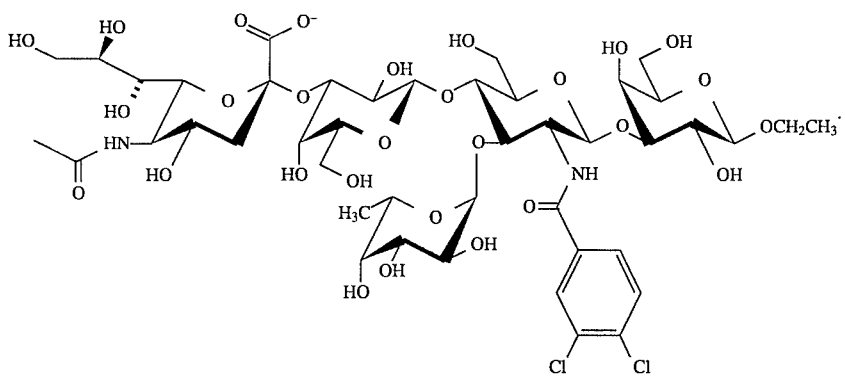
33. The compound according to claim 21 having the formula

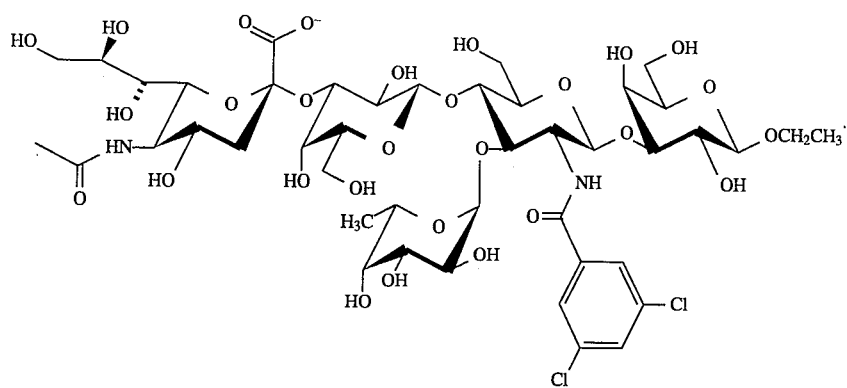
34. The compound according to claim 21 having the formula
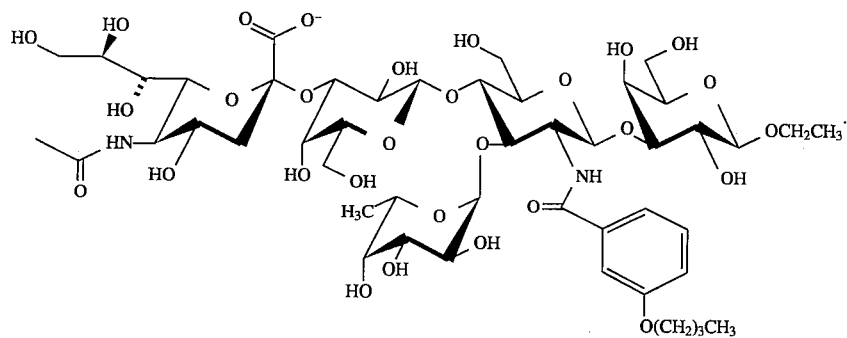
35. The compound according to claim 21 having the formula
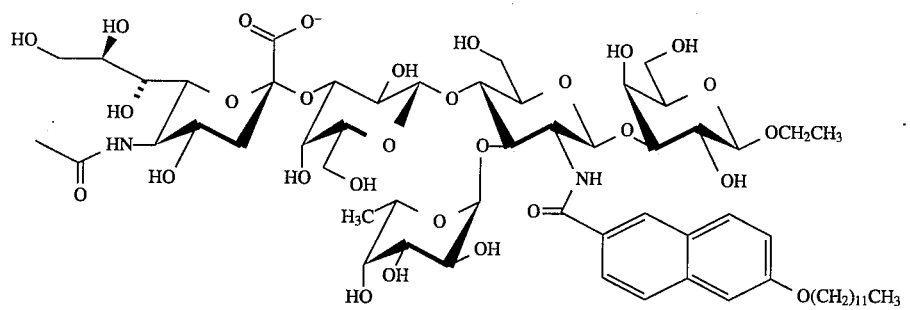
36. The compound according to claim 21 having the formula

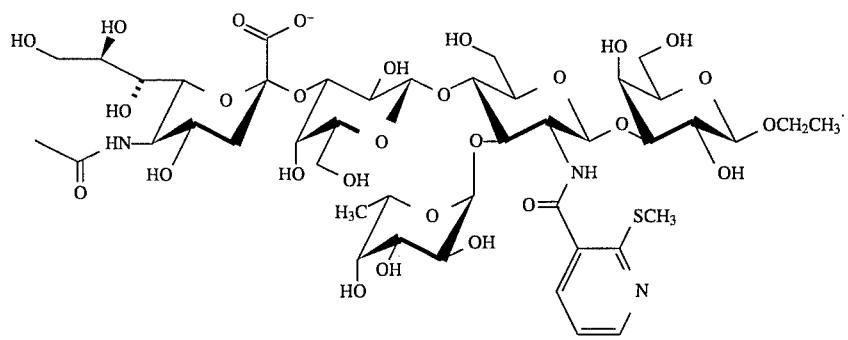
37. The compound according to claim 21 having the formula
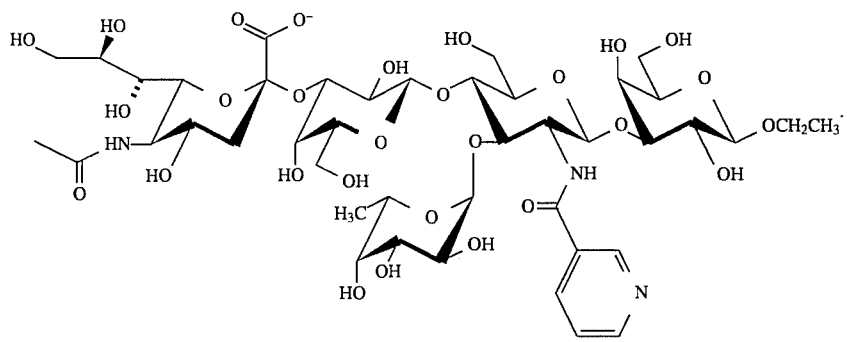
38. The compound according to claim 21 having the formula
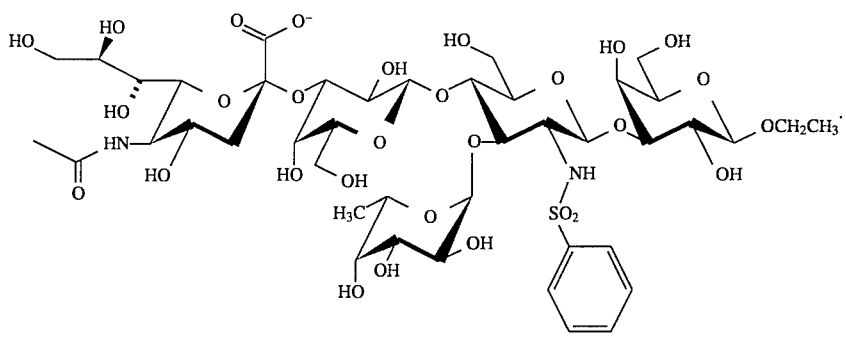
39. A pharmaceutical composition comprising a pharmaceutically acceptable diluent having dissolved or dispersed therein a cellular adhesion-inhibiting amount of a compound of the formula
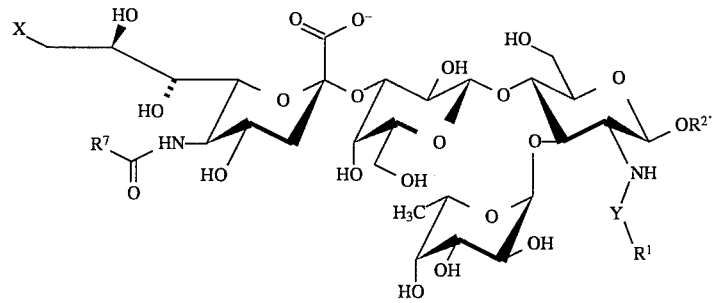

Y is selected from the group consisting of C(O), $SO_2$, HNC(O), OC(O) and SC(O);

$R^1$ is selected from the group consisting of an aryl, a substituted aryl and a phenyl $C_1$-$C_3$ alkylene group, wherein said aryl substituent is selected from the group consisting of a halo, trifluoromethyl, nitro, $C_1$-$C_{18}$ alkyl, $C_1$-$C_{18}$ alkoxy, amino, mono-$C_1$-$C_{18}$ alkylamino, di-$C_1$-$C_{18}$ alkylamino, benzylamino, $C_1$-$C_{18}$ alkylbenzylamino, $C_1$-$C_{18}$ thioalkyl and $C_1$-$C_{18}$ alkyl carboxamido groups;

$R^2$ is selected from the group consisting of monosaccharide, disaccharide, hydrogen, $C_1$-$C_{18}$ straight chain, branched chain or cyclic hydrocarbyl, $C_1$-$C_6$ alkyl $C_1$-$C_5$ alkylene ω-carboxylate, ω-trisubstituted silyl $C_2$-$C_4$ alkylene wherein said ω-trisubstituted silyl is a silyl group having three substituents independently selected from the group consisting of $C_1$-$C_4$ alkyl and phenyl, or $OR^2$ together form a $C_1$-$C_{18}$ straight chain, branched chain or cyclic hydrocarbyl carbamate;

$R^7$ is methyl or hydroxymethyl; and

X is selected from the group consisting of $C_1$-$C_6$ acyloxy, $C_2$-$C_6$ hydroxylacyloxy, hydroxy, halo and azido.

40. The pharmaceutical composition according to claim 39 wherein Y is carbonyl.

41. The pharmaceutical composition according to claim 40 wherein X is hydroxyl.

42. The pharmaceutical composition according to claim 41 wherein $R^2$ is a monosaccharide.

43. The pharmaceutical composition according to claim 42 wherein said monosaccharide is 3GalβOEt.

44. The pharmaceutical composition according to claim 41 wherein $R^2$ is benzyl.

* * * * *